(12) United States Patent
Fornaro et al.

(10) Patent No.: US 10,030,063 B2
(45) Date of Patent: Jul. 24, 2018

(54) PRODUCTION OF THERAPEUTIC PROTEINS IN GENETICALLY MODIFIED MAMMALIAN CELLS

(71) Applicants: Mara Fornaro, Basel (CH); David Jonathan Glass, Cambridge, MA (US); Thomas Jostock, Basel (CH); Holger Laux, Basel (CH); Sandrine Romand, Seyssinet-Pariset (FR)

(72) Inventors: Mara Fornaro, Basel (CH); David Jonathan Glass, Cambridge, MA (US); Thomas Jostock, Basel (CH); Holger Laux, Basel (CH); Sandrine Romand, Seyssinet-Pariset (FR)

(73) Assignee: Novartis AG, Basel (CH)

( * ) Notice: Subject to any disclaimer, the term of this patent is extended or adjusted under 35 U.S.C. 154(b) by 88 days.

(21) Appl. No.: 14/651,694

(22) PCT Filed: Dec. 16, 2013

(86) PCT No.: PCT/IB2013/060982
§ 371 (c)(1),
(2) Date: Jun. 12, 2015

(87) PCT Pub. No.: WO2014/097113
PCT Pub. Date: Jun. 26, 2014

(65) Prior Publication Data
US 2015/0322131 A1 Nov. 12, 2015

Related U.S. Application Data

(60) Provisional application No. 61/738,466, filed on Dec. 18, 2012.

(51) Int. Cl.
C07K 14/65 (2006.01)
C12N 15/113 (2010.01)
C12P 21/02 (2006.01)
C12N 15/11 (2006.01)

(52) U.S. Cl.
CPC ............ *C07K 14/65* (2013.01); *C12N 15/111* (2013.01); *C12N 15/113* (2013.01); *C12N 15/1138* (2013.01); *C12P 21/02* (2013.01); *C12N 2310/14* (2013.01); *C12N 2310/531* (2013.01)

(58) Field of Classification Search
CPC ..... C07K 14/65; C12N 15/113; C12N 15/111; C12N 15/1138; C12N 2310/14; C12N 2310/531; C12P 21/02
See application file for complete search history.

(56) References Cited

U.S. PATENT DOCUMENTS

2005/0255493 A1 11/2005 Macaulay et al.

FOREIGN PATENT DOCUMENTS

WO 06074390 A2 7/2006
WO 07141309 A2 12/2007

OTHER PUBLICATIONS

Kloeting et al., "Autocrine IGF-1 action in adipocytes controls systemic IGF-1 concentrations and growth", Diabetes, Aug. 2008 57(8):2074-2082.
Romero, Christopher J. et al., "Targeted Deletion of Somatotroph Insulin-Like Growth Factor-I-Signaling in a Cell-Specific Knockout Mouse Model", Molecular Endocrinology, May 2010, 24(5):1077-1089.
Gahete, Manuel D. et al., "Elevated GH/IGF-I, Due to Somatotrope-Specific Loss of Both IGF-1 and Insulin Receptors, Alters Glucose Homeostasis and Insulin Sensitivity in a Diet-Dependent Manner", Endocrinology.
Yoon, Diana M., "Effects of exogenous IGF-1 delivery on the early expression of IGF-1 signaling molecules by alignate embedded chondrocytes", Tissue Engineering Part A, Jul. 2008, 14(7):1263-1273.
Yavari, et al., "Knnockdown of IGF-IR by RNAi Inhibits SW480 Colon Cancer Cells Growth In Vitro", Archives of Medical Research, May 2009, 40(4):235-240.
Moschos, Marilita et al., "Expression of the insulin-like growth factor 1 (IGF-1) and type I IGF receptor mRNAs in human HLE-B3 lens epithelial cells", In Vivo (Athens/Greece), Mar. Apr. 2011, 25(2):179-184.
Sunstrom et al., "Recombinant insulin-like growth factor-I (IGF-I) production in Super-CHO results in the expression of IGF-I receptor and IGF binding protein 3", Cytotechnology, Nov. 1998, 28(1-3):91-99.
Stanley, CK Cheung et al., "Glucose lowering effect of transgenic human insulin-like growth factor-I from rice:in vitro and in vivo studies", BNC Biotechnology, Apr. 12, 2011, 11(1):37, abstract.
Zinovieva et al., "Stable production of human insulin-like growth factor 1 (IGF-1) in the milk of hemi-and homozygous transgenic rabbits over several generations", Transgenic Research, Nov. 1, 1998, 7(6):437-447.

(Continued)

*Primary Examiner* — Ruixiang Li
(74) *Attorney, Agent, or Firm* — Hong-Van M. Le

(57) ABSTRACT

The invention relates to methods for the production of therapeutic proteins in mammalian cells. In one embodiment, the method comprises producing a therapeutic protein such as IGF-1 in a mammalian cell endogenously expressing a cognate receptor of said recombinant therapeutic protein and wherein binding of said therapeutic protein to said cognate receptor results in a low titer of the therapeutic protein, the method comprising with a mammalian cell being deficient in the expression of the cognate receptor of said therapeutic protein and being transformed with an expression vector comprising a nucleic acid molecule encoding the therapeutic protein: a. Cultivating said cell under conditions allowing the expression of the therapeutic protein; and b. Harvesting the therapeutic protein from the mammalian cell cultivated in step a, wherein said mammalian cell produces at least 1.5 fold more therapeutic protein than a cell in which the expression of the cognate receptor has not been so modified.

13 Claims, 10 Drawing Sheets

(56) References Cited

OTHER PUBLICATIONS

Isoyama Sho, et al., "Establishment of phosphatidylinositol 3-kinase inhibitor-resistant cancer cell lined and therapeutic strategies for overcoming the resistance", Cancer Science 103:1955-1960. (Oct. 2012).

Xu, Xun et al., "The genomic sequence of the Chinese hamster ovary (CHO)-K1 cell line", Nat. Biotechnol., 29:735-741. (2011).

A)

B)

A)

B)

D= deletion; Ea= Ea peptide; fc domain= immunoglobulin Fc region

PRODUCTION OF THERAPEUTIC PROTEINS IN GENETICALLY MODIFIED MAMMALIAN CELLS

This application is a U.S. National Phase filing of International Application No. PCT/IB2013/060982 filed Dec. 16, 2013, which claims priority to U.S. application Ser. No. 61/738,466 filed Dec. 18, 2018, the contents of which are incorporated herein by reference in their entirety.

FIELD OF THE INVENTION

The present invention relates to methods for the production of a therapeutic protein, which may be a recombinant therapeutic protein in mammalian cell systems.

BACKGROUND OF THE INVENTION

There is a constantly growing need to produce proteins like enzymes, antibodies or hormones for use in therapeutic applications. Currently used state of the art heterologous protein production systems include prokaryotic and eukaryotic cell systems like *E. coli*, yeast, viruses, fungi and insect cells. In order to produce recombinant proteins which require post- or peri-translational modifications such as glycosylation (and where industrial scale production is needed) very often mammalian cell systems including cells from *Cricetulus griseus, Cercopithecus aethiops, Homo sapiens, Mesocricetus auratus, Mus musculus* and *Chlorocebus* species are used. Mammalian cell systems have become a routine production system for therapeutic proteins and antibodies. Said cells have been characterized extensively in the recent history, they can reach extremely high production levels, can be free of infectious or virus like particles, can grow to very high density in bioreactors and they can be genetically manipulated and transformed. For example, Chinese Hamster Ovary (CHO) cells can be engineered to resemble the human glycan profile by transfection of the appropriate glycosyl transferases. Recombinantly produced growth factors are already widely used in therapeutic applications or are promising candidates for the development of new therapies. However, expression of growth hormones in mammalian cells, for example CHO cell lines can result in cell growth inhibition and low titers.

In the near future more and more "non-antibody" protein formats will be part of the pipelines of pharmaceutical companies. However, expression of extracellular signaling molecules as growth factors, hormones, neurotransmitters and cytokines at large scale may not be possible in mammalian cell lines due to growth inhibition resulting in low titers. It is thus clearly desirable to have access to suitable methods for producing growth factors and other therapeutic proteins at industry scale.

SUMMARY OF THE INVENTION

A subject matter of the disclosure relates to:

A method of producing a therapeutic protein in a mammalian cell endogenously expressing a cognate receptor of said therapeutic protein, wherein binding of said therapeutic protein to said cognate receptor results in a low titer of the therapeutic protein, the method comprising with the steps of:
   a. Cultivating a mammalian cell comprising a nucleic acid encoding a therapeutic protein under conditions allowing expression of said therapeutic protein, wherein the cell is deficient in expression of a cognate receptor of said therapeutic protein; and
   b. Harvesting said therapeutic protein from said mammalian cell.

Another subject matter of the disclosure relates to a method of producing a therapeutic protein in a mammalian cell endogenously expressing a cognate receptor of said therapeutic protein and wherein binding of said therapeutic protein to said cognate receptor results in a low titer of the therapeutic protein, the method comprising with a mammalian cell being deficient in the expression of the cognate receptor of said therapeutic protein and being transformed with an expression vector comprising a nucleic acid molecule encoding the therapeutic protein:
   c. Cultivating said cell under conditions allowing the expression of the therapeutic protein; and
   d. Harvesting the therapeutic protein from the mammalian cell cultivated in step a.

In another embodiment of the disclosure, the method relates to heterologously producing a recombinant therapeutic protein in a mammalian cell endogenously expressing a cognate receptor of said recombinant therapeutic protein and wherein binding of said recombinant therapeutic protein to said cognate receptor results in a growth retardation of said mammalian cell and a low titer of the recombinant therapeutic protein, the method comprising with a mammalian cell being deficient in the expression of the cognate receptor of said recombinant therapeutic protein and being transformed with an expression vector comprising a nucleic acid molecule encoding the heterologous recombinant therapeutic protein under the control of a constitutive or inducible promoter:
   e. Cultivating said cell under conditions allowing the expression of the recombinant therapeutic protein; and
   f. Harvesting the recombinant therapeutic protein from the mammalian cell cultivated in step a.

In a particular embodiment, the mammalian cell being deficient in the expression of the cognate receptor of said therapeutic protein, which may be a recombinant therapeutic protein, as described above produces at least 1.5-fold, or 2-fold, or 3-fold, or 4-fold, or 5 fold, or 6-fold, or 7-fold, or 8-fold, or 9-fold, or 10-fold or more therapeutic protein than a cell of the same type in which the expression of the cognate receptor has not been so modified.

In another embodiment of the disclosure the therapeutic protein mentioned above, which may be a recombinant therapeutic protein, is a growth factor.

In yet another embodiment, the growth factor is the Insulin like growth factor 1 protein or a variant thereof and the disclosure relates to a method of producing Insulin like growth factor 1 protein or a variant thereof in a mammalian cell, wherein said mammalian cell being deficient in the expression of a functional Insulin like growth factor 1 receptor (IGF-1R), the method comprising
   a. Cultivating said cell under conditions allowing the expression of the IGF-1 or a variant thereof; and
   b. Harvesting the IGF-1 or a variant thereof from the mammalian cells cultivated in step a, wherein said mammalian cell produces at least 1.5-fold, or 2-fold, or 3-fold, or 4-fold, or 5 fold, or 6-fold, or 7-fold, or 8-fold, or 9-fold, or 10-fold or more IGF-1 or a variant thereof than a cell of the same type in which the expression of the IFG1R has not been so modified.

In another embodiment of the disclosure, the mammalian cells being deficient in the expression of the cognate receptor of said therapeutic protein, which may be a recombinant therapeutic protein, e.g. the Insulin like growth factor 1 receptor, have been genetically modified and the deficiency in the expression of said cognate receptor has been achieved by applying RNA-interference or targeted genetic recombination technologies.

In a particular embodiment of the disclosure, the cognate receptor of the therapeutic protein, which may be a recombinant therapeutic protein, is knocked out by the use of a zinc finger nuclease.

In another embodiment the disclosure relates to one of the above described methods, wherein the deficiency in the expression of the cognate receptor of the therapeutic protein, which may be a recombinant therapeutic protein, in the mammalian cell has been achieved by applying RNA-interference, the method comprising:
(a) introducing into said cell double-stranded ribonucleic acid (dsRNA) molecules, wherein the dsRNA comprises at least two sequences that are complementary to each other and wherein a sense strand comprises a first sequence and an antisense strand comprises a second sequence comprising a region of complementarity which is substantially complementary to at least a part of the mRNA encoding the cognate receptor of the therapeutic protein, and wherein said region of complementarity is less than 30 nucleotides in length and wherein said dsRNA upon introduction into said cell inhibits expression of the gene encoding the cognate receptor of the recombinant therapeutic protein by at least 10%; and
(b) maintaining the cell produced in step (a) for a time sufficient to obtain degradation of the mRNA transcript of the gene encoding the cognate receptor of the therapeutic protein, which may be a recombinant therapeutic protein, thereby inhibiting expression of said cognate receptor gene in the cell.

In a particular embodiment of the disclosure the cognate receptor of said therapeutic protein is the Insulin like growth factor 1 receptor and the method comprises:
(a) introducing into said cell a double-stranded ribonucleic acid (dsRNA), wherein the dsRNA comprises at least two sequences that are complementary to each other and wherein a sense strand comprises a first sequence and an antisense strand comprises a second sequence comprising a region of complementarity which is substantially complementary to at least a part of the mRNA encoding the IGF-1R of said mammalian cell, and wherein said region of complementarity is less than 30 nucleotides in length and wherein said dsRNA upon introduction into said cell inhibits expression of the IGF-1R gene by at least 40%; and
(b) maintaining the cell produced in step (a) for a time sufficient to obtain degradation of the mRNA transcript of the IGF-1R gene, thereby inhibiting expression of the IGF-1R gene in the cell.

In another particular embodiment of the above described method, which may be combined with any of the preceding embodiments of the disclosure, the RNA-interference is achieved by using a shRNA molecule, the method comprising:
(a) introducing into said cell a vector encoding shRNA which is substantially complementary to at least a part of the mRNA encoding the cognate receptor of the recombinant therapeutic protein, and wherein said shRNA upon introduction into said cell inhibits expression of said cognate receptor gene by at least 10%; and
(b) maintaining the cell produced in step (a) for a time sufficient to obtain degradation of the mRNA transcript of said cognate receptor gene.

In certain aspects the disclosure relates to the above described methods, wherein the mammalian cell is selected from the group consisting of *Cricetulus griseus*, *Cercopithecus aethiops*, *Homo sapiens*, *Mesocricetus auratus*, *Mus musculus* and *Chlorocebus* species cells. In another aspect the mammalian cell is selected from the group consisting of CHO, COS, Vero, Hela, BHK, HEK NS0, C127, hybridoma, PerC6®, CAP and Sp-2/0, cells. In a particular aspect, the mammalian cell used in the above disclosed method is a Chinese Hamster Ovary (CHO) cell, wherein said CHO cell can be a derivative of a CHO-K1 cell, a derivative of a CHO-DUXB11 cell, a CHO-DG44 cell, a CHO-SSF3 cell or a derivative of a CHO-S cell.

In an additional embodiment, the deficiency in the expression of the Insulin like growth factor 1 receptor in CHO-DUXB11 derived cells has been achieved by using small hairpin RNA (shRNA) molecules, wherein the sequence of said shRNA molecules is selected from the group consisting of SEQ ID NOs.: 5, 6, 7, 8, 9 and 10.

In an additional embodiment, the deficiency in the expression of the Insulin like growth factor 1 receptor as described above has been achieved by using double stranded short interference RNA (siRNA) molecules, wherein the sequence of the sense strand of said siRNAs comprises a sequence selected from the group consisting of SEQ ID NOs: 1 and 3.

The disclosure furthermore relates to dsRNA molecules comprising the sense strand of a siRNA selected from the group consisting of SEQ ID NOs: 1 and 3. In a further aspect the disclosure relates to shRNA molecules comprising a sequence selected from the group consisting of SEQ ID NOs.: 5, 6, 7, 8, 9 and 10.

In yet another embodiment, the deficiency in the expression of Insulin like growth factor 1 receptor has been achieved by producing knock out cells using targeted genetic recombination technologies.

Accordingly, the disclosure also relates to the above described method, wherein the cognate receptor is the IGF-1R and the therapeutic protein is the IGF-1 or a variant thereof and the deficiency in the expression of the IGF-1R has been achieved by using zinc finger nucleases.

In an additional embodiment the disclosure relates to the above described method, wherein the Insulin like growth factor 1 protein is the human Insulin like growth factor 1 protein (SEQ ID NO.: 16) or a variant thereof.

In another embodiment the methods disclosed above comprising the steps
a. Producing a mammalian cell being deficient in the expression of the cognate receptor of a therapeutic protein of interest that should be produced in said cell;
b. Transforming the cell of step a. with an expression vector comprising a nucleic acid molecule encoding the therapeutic protein of interest;
c. Selecting cell of step b. being transformed;
d. Cultivating the mammalian cell selected in step c. under conditions allowing the expression of said therapeutic protein of interest; and
e. Harvesting said therapeutic protein from the mammalian cells cultivated in step d, wherein alternatively the order of steps a. and b. can be reversed or both steps can be performed at the same time.

In a furthermore particular embodiment the method disclosed above relates to the production of an IGF-1, e.g. the human IGF-1 (SEQ ID NO.: 16) or a variant thereof (e.g. SEQ ID NOs.: 21-29) comprising the steps:
a. Producing a mammalian cell being deficient in the expression of the Insulin like growth factor 1 receptor;
b. Transforming the cell of step a. with an expression vector comprising a nucleic acid molecule encoding an IGF-1, e.g. a human IGF-1 or a variant thereof;

c. Selecting a cell of step b. being transformed;
d. Cultivating the mammalian cell of step c. under conditions allowing the expression of the IGF-1 protein; and
e. Harvesting said IGF-1 protein or the variant thereof from the mammalian cells cultivated in step d, wherein alternatively the order of steps a. and b. can be reversed or both steps can be performed at the same time and,
wherein said mammalian cell produces at least 1.5-fold, or 2-fold, or 3-fold, or 4-fold, or 5 fold, or 6-fold, or 7-fold, or 8-fold, or 9-fold, or 10-fold or more higher IGF-1 or a variant thereof than a cell of the same type in which the expression of the IGF-1R has not been so modified.

In another aspect, the disclosure relates to the above described methods, wherein the therapeutic protein, which can be a growth factor, particularly an IGF-1 protein or the human IGF-1 (SEQ ID NO.: 16) or a variant thereof (e.g. SEQ ID NOs.: 21-29) being produced at industrial manufacturing scale.

The disclosure furthermore provides for a mammalian cell which is genetically modified, so that the expression of an Insulin like growth factor 1 protein, e.g. the human IGF-1 (SEQ ID NO.:16) or a variant thereof (e.g. SEQ ID NOs.: 21-29) is at least 1.5-fold, or 2-fold, or 3-fold, or 4-fold, or 5 fold, or 6-fold, or 7-fold, or 8-fold, or 9-fold, or 10-fold or more higher compared to a cell of the same type which has not been so modified and wherein said genetic modification results in a deficient expression of the IGF-1 receptor.

In another aspect of the disclosure, which may be combined with any of the preceding embodiments of the disclosure, the mammalian cell described above is a *Cricetulus griseus* cell, *Cercopithecus aethiops* cell, *Homo sapiens* cell, *Mesocricetus auratus* cell, *Mus musculus* cell and *Chlorocebus* species cell.

In a certain embodiment the mammalian cell described above is a Chinese Hamster Ovary cell, particularly a derivative of a CHO-K1 cell, a derivative of a CHO-DUXB11 cell, a CHO-DG44 cell, a CHO-SSF3 cell or a derivative of a CHO-S cell and the deficiency in the expression of the IGF-1 receptor in said cells has been achieved by applying RNA-interference or targeted genetic recombination technologies.

In another aspect the disclosure relates to the use of a mammalian cell for the production of a therapeutic protein, which may be a recombinant therapeutic protein, wherein said cell is deficient in the expression of an endogenous cognate receptor of said therapeutic protein and wherein binding of said therapeutic protein to said cognate receptor in a cell not being deficient in the expression of said cognate receptor would result in a growth retardation of said mammalian cell and/or a low titer of the therapeutic protein.

Another embodiment of the disclosure relates to the above described use, wherein the therapeutic protein, which may be a recombinant therapeutic protein, is a growth factor.

Another particular embodiment of the disclosure relates to the above described use wherein the growth factor is the Insulin like growth factor 1 protein or a variant thereof and the cognate receptor is the Insulin like growth factor 1 receptor.

GENERAL DEFINITIONS

Figure 1:
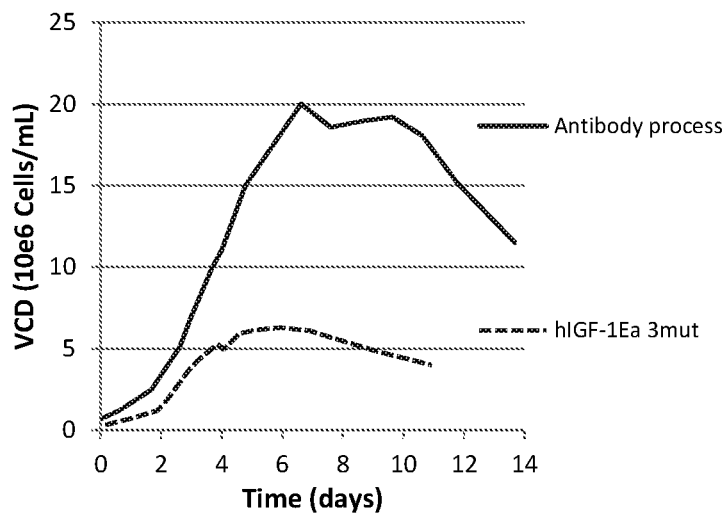
FIG. 1: A: Cell growth: Viable cell density (VCD) of CHO-K1 derivative cells expressing a recombinant antibody (bold line) and CHO-K1 derivative cells expressing hIGF-1Ea 3mut (SEQ ID NO.: 35) (dotted line) in bioreactor runs. B: Cell viability: Percentage of viable cells in bioreactor runs (bold line antibody producing CHO-K1 derivative clone, dotted line hIGF-1Ea 3mut expressing clones).
Figure 1:
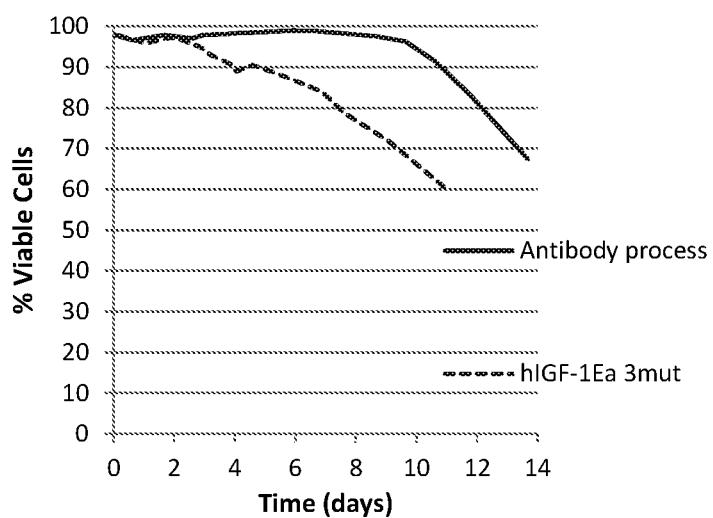

In order that the present invention may be more readily understood, certain terms are first defined. Additional definitions are set forth throughout the detailed description.

About: the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 30 percent, preferably 20 percent up or down (higher or lower). As used herein, the word "or" means any one member of a particular list.

Cognate receptor: as used herein, the term "cognate receptor" of e.g. a heterologous recombinant therapeutic protein refers to an endogenous receptor of a mammalian cell (used for the expression of said therapeutic protein), wherein the heterologous recombinant therapeutic protein is a ligand of said receptor. In other words, the cognate receptor specifically bind the heterologous recombinant therapeutic protein and binding thereof triggers a physiological response (e.g. induces a signal transduction reaction) in said cell.

Comprising: the term "comprising" means "including" e.g. a composition "comprising" X may consist exclusively of X or may include something additional e.g. X+Y.

Deficient in the expression of given gene: the phrase "deficient in the expression of given gene" refers to a situation in which a certain gene in a cell, upon genetic manipulation, shows a reduced expression level. An expression level is reduced if the (i) amount of mRNA being transcribed from said gene or (ii) the amount of protein being encoded by said gene or (iii) the activity of the protein encoded by said in a genetically manipulated cell, wherein genetically manipulated cell includes induced or spontaneous mutations, is lower than the amount/activity of mRNA and/or protein encoded by said gene in a cell of the same type not being genetically manipulated. The terms "deficiency" and "reduction" are used interchangeably and cover situations in which the level of gene expression ranges from being completely abolished (e.g. homozygous gene knock-out) to a reduction of 10%, 20%, or 30%, or 40%, or 50%, or 60%, or 70%, or 80%, or 90%, or 95% or even higher (e.g. heterozygous knock out, siRNA or shRNA approaches) compared to the expression level of said gene in a cell of the same type not being genetically manipulated, wherein the expression level is measured by determining RNA and/or protein levels. Deficient in expression of given gene also refers to a situation where mRNA and/or protein are expressed at normal levels but in a non-functional form or with impaired function.

Heterologous: as used herein, the term "heterologous" when relating to a recombinant protein indicates that the species from which the cell is derived is not the same as the species from which the polypeptide is derived. For example, a recombinant therapeutic protein is a heterologous recombinant therapeutic protein if the protein has a human amino acid sequence and said protein is expressed in a CHO cell. "Heterologous" with respect to a nucleic acid sequence also refers to a nucleotide sequence, which is ligated to a nucleic acid sequence (e.g. a promoter) to which it is not ligated in nature, or to which it is ligated at a different location in nature. Additionally, the phrase being "heterologous" to a mammalian cell, e.g. a CHO cell, in the context of a nucleic acid sequence (e.g. a promoter sequence) indicates that said nucleic acid sequence has originated from a different organism (e.g. a human promoter used to drive the expression of a certain gene in a non-human organism)

The terms "Inhibition" and "retardation" are used interchangeably in the context of this invention and cover situations in which mammalian cell growth and/or protein production of mammalian cells is negatively impacted as a result of the expression of a heterologous protein. Hence, cell growth inhibition or retardation refers to a situation in which, for example, the number of viable cells in a cell culture, the viability of cells over a certain cultivation period, the maximum reachable cell density and/or the production rate of total or individual proteins is reduced in transgenic cells compared to the non-transformed parental cell line.

Industrial manufacturing scale: the term "industrial manufacturing scale" in the context of heterologous recombinant protein production in mammalian cells refers to bioreactor production systems like conventional or air lift bioreactors being used for batch, fed-batch or perfusion cultivations. The bioreactors ranging from 50 liter to 2,000 liter for pilot scale reactors, 2,000 liter to 5,000 liter for airlift bioreactors and up to 25,000 liter for conventional stainless steel stirred bioreactors. The production of polypeptides in large scale can be done for example in wave, glass or stainless steel bioreactors. For that purpose the cells are expanded, usually starting from a single frozen vial, for example a vial from a Master Cell Bank. The cells are thawed and expanded through several steps. Bioreactors of different scale are inoculated with appropriate amounts of cells. The cell density can be increased by adding feed solutions and additives to the bioreactor. Cells are kept at a high viability for a prolonged time. Product titers in the reactor ranging from a few hundred milligrams per liter up to several grams per liter are achieved in the large scale. Purification can be done by standard chromatography methodology, which can include affinity, ion exchange, hydrophobic interaction or size exclusion chromatography steps. The size of the bioreactor can be up to several thousand liters volume in the final scale (see also e.g. F. Wurm, Nature Biotechnology Vol. 22, 11, 2004, 1393-1398). The amount of protein produced in the above described systems ranges normally from 1 g/L to 5 g/L. An industrial manufacturing scale allows to (i) grow cells up to 2.5×10⁷ cells/ml during the cultivation time, (ii) cultivate cells over a period of more than 200 hours thereby maintaining (iii) a cell viability of over 90%.

Insulin like growth factor 1 protein or a variant thereof: the phrase "Insulin like growth factor 1 protein or a variant thereof" refers to proteins being encoded by Insulin like growth factor-1 genes, particularly preferred is the human Insulin like growth factor 1 (hIGF-1) protein and variants thereof. An IGF-1 protein variant is a protein that differs by at least one amino acid from the IGF-1 wild-type sequence, wherein the term "wild-type sequence" refers to a polypeptide or gene sequence available in at least one naturally occurring organism or a polypeptide or gene sequence that has not been changed, mutated, or otherwise manipulated by man.

An IGF-1 variant is also the IGF-1 precursor protein or the pro-IGF-1 protein comprising a peptide leader sequence. An IGF-1 variant is also a fusion protein comprising an IGF-1 protein, e.g. a protein comprising an IGF-1 protein fused to an immunoglobulin Fc region. Examples for IGF-1 variants are disclosed inter alia in the patent applications WO05033134 (stabilized IGF-1 protein fused to an immunoglobulin Fc region) and WO2007/146689 (stabilized IGF-1 precursor proteins). An IGF-1 variant as described above retains its biological activity in the sense that such a protein can be considered as a functional equivalent of the wildtype IGF-1.

Functional equivalents with regard to the IGF-1 protein have to be understood as IGF-1 proteins comprising natural or artificial mutation. Mutations can be insertions, deletions or substitutions of one or more nucleic acids that do not diminish the biological activity of the IGF-1 protein. Functional equivalents having an identity of at least 80%, preferably 85%, more preferably 90%, most preferably more than 95%, very especially preferably at least 98% identity—but less than 100% identity to the IGF-1 wildtype protein, e.g. the human IGF-1 protein (SEQ ID NO.: 16). In case of fusion proteins as described above, the 100% identity shall be defined only on the basis of the IGF-1 part of such a fusionprotein. Insulin-like growth factors (IGFs) are part of a complex system that cells use to communicate with their physiologic environment. This complex system (often referred to as the insulin-like growth factor axis) consists of two cell-surface receptors (IGF-1R and IGF-2R), two ligands (IGF-1 and IGF-2), a family of six high-affinity IGF-binding proteins (IGFBP 1-6), and associated IGFBP degrading enzymes (proteases). This system is important not only for the regulation of normal physiology but also for a number of pathological states (Glass, Nat Cell Biol 5:87-90, 2003). The IGF axis has been shown to play roles in the promotion of cell proliferation and the inhibition of cell death (apoptosis). IGF-1 is mainly secreted by the liver as a result of stimulation by human growth hormone (hGH). Almost every cell in the human body is affected by IGF-1, especially cells in muscles, cartilage, bones, liver, kidney, nerves, skin and lungs. In addition to the insulin-like effects, IGF-1 can also regulate cell growth. IGF-1 and IGF-2 are regulated by a family of gene products known as the IGF-binding proteins. These proteins help to modulate IGF action in complex ways that involve both inhibiting IGF action by preventing binding to the IGF receptors as well as promoting IGF action through aiding delivery to the receptors and increasing IGF half-life in the blood stream. There are at least six characterized binding proteins (IGFBP1-6). IGF-1 is used in a wide range of therapeutic applications. Mecasermin (brand name Increlex™) is a synthetic analog of IGF-1 which is approved for the treatment of growth failure. Several companies have evaluated IGF-1 in clinical trials for a variety of additional indications, including type 1 diabetes, type 2 diabetes, amyotrophic lateral sclerosis, severe burn injury and myotonic muscular dystrophy.

Introducing into a cell: "Introducing into a cell", when referring to nucleic acid molecules (DNA RNA), refers basically to the process of transformation or transfection. "Introducing into a cell", when referring to a dsRNA can also mean facilitating uptake or absorption of the dsRNA into the cell, as it is understood by those skilled in the art. Absorption or uptake of dsRNA can occur through unaided diffusive or active cellular processes, or by auxiliary agents or devices Mammalian cell: the term "mammalian cell" in the context of the disclosed method refers to cells which are suitable for protein production at industrial manufacturing scale. Those cells are well known to the skilled person and have originated for example from *Cricetulus griseus, Cercopithecus aethiops, Homo sapiens, Mesocricetus auratus, Mus musculus* and *Chlorocebus* species. The respective cell lines are known as CHO-cells (Chinese Hamster Ovary), COS-cells (a cell line derived from monkey kidney (African green monkey), Vero-cells (kidney epithelial cells extracted from African green monkey), Hela-cells (The line was derived from cervical cancer cells taken from Henrietta Lacks), BHK-cells (baby hamster kidney cells, HEK-cells (Human Embryonic Kidney), NS0-cells (Murine myeloma cell line), C127-cells (nontumorigenic mouse cell line), PerC6®-cells (human cell line, Crucell), CAP-cells (CEVEC's Amniocyte Production) and Sp-2/0-cells (Mouse myeloma cells).

RNA interference: the term "RNA interference" or "RNAi" is well known in the art and is commonly understood to mean the inhibition of one or more target genes in a cell by "siRNA" or "small-interfering ribonucleic acid" with a region which is complementary to the target gene. Various assays are known in the art to test siRNA for its ability to mediate RNAi (see for instance Elbashir et al., Methods 26 (2002), 199-213). The effect of the siRNA according to the present invention on gene expression will typically result in expression of the target gene being inhibited by at least 10%, 30%, 50%, 90%, 95% or 99% when compared to a cell not treated with e.g. the siRNA molecules as described herein.

"siRNA" or "small-interfering ribonucleic acid" according to the invention has the meanings known in the art, including the following aspects: The siRNA consists of two strands of ribonucleotides which hybridize along a complementary region under physiological conditions. The strands are separate but they may be joined by a molecular linker in certain embodiments. The individual ribonucleotides may be unmodified naturally occurring ribonucleotides, unmodified naturally occurring deoxyribonucleotides or they may be chemically modified or synthetic as described elsewhere herein.

The siRNA molecules in accordance with the present invention comprise a double-stranded region which is substantially identical to a region of the mRNA of the target gene. A region with 100% identity to the corresponding sequence of the target gene is suitable. This state is referred to as "fully complementary". However, the region may also contain one, two or three mismatches as compared to the corresponding region of the target gene, depending on the length of the region of the mRNA that is targeted, and as such may be not fully complementary. In an embodiment, the RNA molecules used in the disclosed methods specifically target one given gene. In order to only target the desired mRNA, the siRNA reagent may have 100% homology to the target mRNA and at least 2 mismatched nucleotides to all other genes present in the cell or organism. Methods to analyze and identify siRNAs with sufficient sequence identity in order to effectively inhibit expression of a specific target sequence are known in the art. Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group).

Another factor affecting the efficiency of the RNAi reagent is the target region of the target gene. The region of a target gene effective for inhibition by the RNAi reagent may be determined by experimentation. A suitable mRNA target region would be the coding region. Also suitable are untranslated regions, such as the 5'-UTR, the 3'-UTR, and splice junctions. For instance, transfection assays as described in Elbashir S. M. et al, 2001 EMBO J., 20, 6877-6888 may be performed for this purpose. A number of other suitable assays and methods exist in the art which are well known to the skilled person.

The length of the region of the siRNA complementary to the target, in accordance with the present invention, may be from 18 to 100 nucleotides, 18 to 25 nucleotides, 18 to 22 nucleotides or 19 nucleotides. Where there are mismatches to the corresponding target region, the length of the complementary region is generally required to be somewhat longer.

Because the siRNA may carry overhanging ends (which may or may not be complementary to the target), or additional nucleotides complementary to itself but not the target gene, the total length of each separate strand of siRNA may be 18 to 100 nucleotides, 18 to 49 nucleotides, 18 to 30 nucleotides or 18 to 25 nucleotides.

A small hairpin RNA or short hairpin RNA (shRNA) is a sequence of RNA that makes a tight hairpin turn that can be used to silence target gene expression via RNA interference (RNAi). Small hairpin RNAs (shRNAs) can be transcribed in vivo can trigger degradation of corresponding mRNAs similar to the siRNAs (Shi, 2003). These developments raise the possibility that siRNA duplexes or vectors expressing shRNAs (small hairpin RNAs) maybe used to block the expression of a gene, e.g. encoding a receptor. Regulatable promoters for synthesis of small hairpin RNA have been described and are well known to the person skilled in the art (e.g. WO05007877A).

Targeted genetic recombination: as used herein, the term "targeted genetic recombination" refers to a process wherein recombination occurs within a DNA target locus present in a host cell or host organism. Recombination can involve either homologous or non-homologous DNA. To achieve targeted genetic recombination genome editing with engineered nucleases (GEEN) is a method which can be applied. Widely used engineered nucleases are zinc finger nuclease (ZFN), transcription activator-like effector nucleases (TAL-ENs), engineered meganucleases, like reengineered homing endonucleases. One example of homologous targeted genetic recombination would be cleavage of a selected locus of host DNA by a zinc finger nuclease (ZFN) (as disclosed in WO03087341), followed by homologous recombination of the cleaved DNA with homologous DNA of either exogenous or endogenous origin. One example of non-homologous targeted genetic recombination would be cleavage of a selected locus of host DNA by a ZFN, followed by non-homologous end joining (NHEJ) of the cleaved DNA. As used herein, the terms "host cell" or "host organism" or, simply, "target host", refer to a cell or an organism that has been selected to be genetically transformed to carry one or more genes for expression of a function used in the methods of the present invention. A host can further be an organism or cell that has been transformed by the targeted genetic recombination or mutation methods of the present invention.

Therapeutic protein: the term "therapeutic protein" refers to protein for human or veterinary therapy and may be intended for acute or chronic administration. In particular, a "therapeutic protein" is a protein used in the treatment of a mammal having a disease or pathological condition.

Transformation: The term "transformation of"/"transforming" a mammalian cell or "transformed" refers to the introduction of a recombinant DNA construct, e.g. a protein expression construct or a shRNA expression construct into said mammalian cell. Transformation describes the process of integrating and stably maintaining a recombinant DNA in the genome of a cell, e.g. a mammalian cell like CHO cells. Stably maintaining a recombinant DNA construct covers the integration of said DNA construct into the genome of the host organism as well as the extra chromosomal presence of a vector in a host organism, e.g. in case of a transient expression vector. The term "transformation" is used herein interchangeably with the terms "transfection" or "transduction".

Sense strand: The term "sense strand," as used herein, refers to the strand of a dsRNA that includes a region that is substantially complementary to a region of the antisense strand.

DETAILED DESCRIPTION OF THE INVENTION

Disclosed is a solution for the problem that producing a therapeutic protein, which can be a recombinant therapeutic protein, in a mammalian cell endogenously expressing a cognate receptor of said therapeutic protein, can result in growth retardation of said mammalian cell and/or a low titer of the therapeutic protein (see example section). Therefore, in one aspect, the invention provides a method of producing a therapeutic protein, which can be a recombinant protein, in a mammalian cell endogenously expressing a cognate receptor of said therapeutic protein and wherein binding of said therapeutic protein to said cognate receptor results in a growth retardation of said mammalian cell and/or a low titer of the therapeutic protein, the method comprising with a mammalian cell being deficient in the expression of the cognate receptor of said therapeutic protein and being transformed with an expression vector comprising a nucleic acid molecule encoding said therapeutic protein:

a. Cultivating said cell under conditions allowing the expression of the therapeutic protein; and
b. Harvesting the therapeutic protein from the mammalian cell cultivated in step a.

In a particular embodiment the above described method comprises the step of processing the isolated therapeutic protein.

In another embodiment the disclosure provides a solution for the problem that producing a therapeutic protein under the control of a constitutive or inducible heterologous promoter in a mammalian cell endogenously expressing a cognate receptor of said therapeutic protein can result in growth retardation of said mammalian cell and/or a low titer of the recombinant therapeutic protein (see example section).

Therefore, in one aspect, the invention provides a method of heterologously producing a recombinant therapeutic protein in a mammalian cell endogenously expressing a cognate receptor of said recombinant therapeutic protein and wherein binding of said recombinant therapeutic protein to said cognate receptor results in a growth retardation of said mammalian cell and/or a low titer of the recombinant therapeutic protein, the method comprising with a mammalian cell being deficient in the expression of the cognate receptor of said recombinant therapeutic protein and being transformed with an expression vector comprising a nucleic acid molecule encoding the heterologous recombinant therapeutic protein under the control of a constitutive or inducible promoter being heterologous to said mammalian cell:

c. Cultivating said cell under conditions allowing the expression of the recombinant therapeutic protein; and
d. Harvesting the recombinant therapeutic protein from the mammalian cell cultivated in step a, In a particular embodiment the above described method comprises the step of processing the isolated therapeutic protein.

Large scale production of polypeptides with transfected mammalian cells, e.g. CHO cells can be done for example in wave, glass or stainless steel bioreactors. For that purpose the cells are expanded, usually starting from a single frozen vial, for example a vial from a Master Cell Bank. The cells are thawed and expanded through several steps. Bioreactors of different scale are inoculated with appropriate amounts of cells. The cell density can be increased by adding feed solutions and additives to the bioreactor. Cells are kept at a high viability for a prolonged time. Product concentrations in the reactor ranging from a few hundred milligrams per liter up to several grams per liter are achieved in the large scale. Purification can be done by standard chromatography methodology, which can include affinity, ion exchange, hydrophobic interaction or size exclusion chromatography steps. The size of the bioreactor can be up to several thousand liters volume in the final scale (see also e.g. F. Wurm, Nature Biotechnology Vol. 22, 11, 2004, 1393-1398).

In a particular embodiment, the mammalian cell being deficient in the expression of the cognate receptor of said therapeutic protein of interest produces at least 1.5-fold, or 2-fold, or 3-fold, or 4-fold, or 5 fold, or 6-fold, or 7-fold, or 8-fold, or 9-fold, or 10-fold or more therapeutic protein than a cell in which the expression of the cognate receptor of the therapeutic protein has not been so modified.

In yet another embodiment of the disclosure, the cells modified as described above have at least 5 percent, or 10 percent or 15 percent or 20 percent or 30 percent or 40 percent, or 50 percent or more viable cells compared to a control population. Alternatively, or in addition, the modified cells maintain cell viability for a longer period of time compared to cells which have not been modified. For example, modified cells are able to maintain certain percentage cell viability (e.g., 95 percent) for a longer period compared to control cells.

In another particular embodiment, the mammalian cells being deficient in the expression of the cognate receptor of said therapeutic protein of interest grow up to a cell density of $0.5$-$1 \times 10^7$ cells/ml or $1$-$1.5 \times 10^7$ cells/ml or $1.5$-$2 \times 10^7$ cells/ml or $2$-$2.5 \times 10^7$ cells/ml or $3$-$3.5 \times 10^7$ cells/ml or higher during the cultivation time. The viability of the mammalian cells being deficient in the expression of the cognate receptor of said therapeutic protein is over 90% during the first 80-110 h or 110-140 h or 140-170 h or 170-200 h or 200-230 h or 230-260 h or longer cultivation time.

Figure 10:
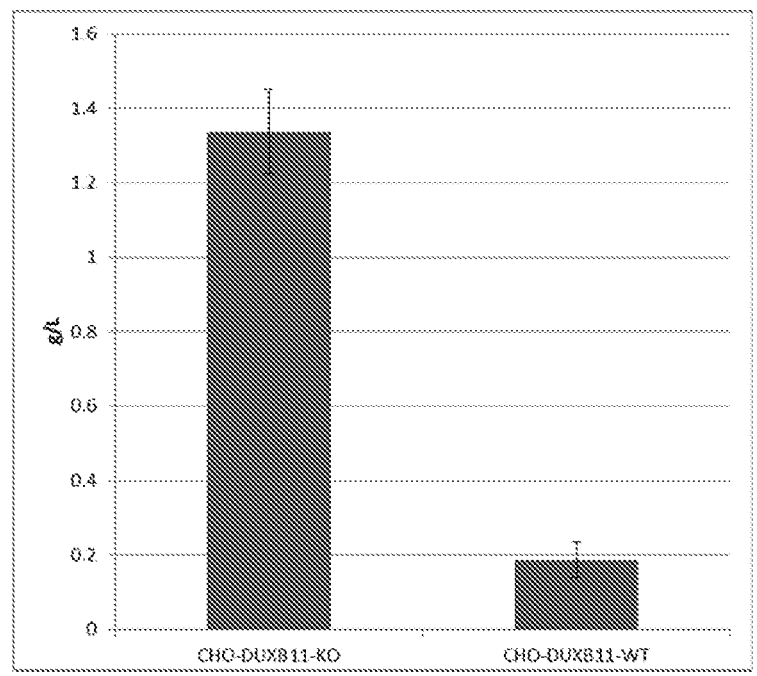
FIG. 10: IGF-1-Fc fusion Protein titers of clones at day 14 of 50 ml batch cultures. The titers of the IGF-1-Fc fusion protein: hIGF-1-Ea-fc_mut 13/2_A in 15 best CHO-DUXB11 derivative IGF-1R-KO clones is ca. 6-7 fold higher compared to the titer of the IGF-1-Fc fusion protein: hIGF-1-Ea-Δ1-3, R37A, Δ71-72, R77Q-fc domain in CHO-DUXB11 derivative wildtype cell clones.

In an additional embodiment, a culture of the mammalian cell being deficient in the expression of the cognate receptor of said therapeutic protein of interest and cultured under conditions as described in FIG. 10, produces at least 0.4 g/L or 0.6 g/L or 0.8 g/L or 1.0 g/L or 1.2 g/L or 1.4 g/L or 1.6 g/L or 1.8 g/L or 2.0 g/L or 2.2 g/l or more therapeutic protein.

In another embodiment the therapeutic protein mentioned above is a growth factor. Growth factors are known in the art and include, without being limited to, Adreno-medullin (AM), Angiopoietin (Ang), Autocrine motility factor, Bone morphogenetic proteins (BMPs), Brain-derived neurotrophic factor (BDNF), Epidermal growth factor (EGF), Erythropoietin (EPO), Fibroblast growth factor (FGF), Glial cell line-derived neurotrophic factor (GDNF), Granulocyte colony-stimulating factor (G-CSF), Granulocyte macrophage colony-stimulating factor (GM-CSF), Growth differentiation factor-9 (GDF9) Hepatocyte growth factor (HGF), Hepatoma-derived growth factor (HDGF), Migration-stimulating factor, Myostatin (GDF-8), Nerve growth factor (NGF) and other neurotrophins, Platelet-derived growth factor (PDGF), Thrombopoietin (TPO), Transforming growth factor alpha (TGF-α), Transforming growth factor beta (TGF-β), Tumor_necrosis_factor-alpha (TNF-α), Vascular endothelial growth factor (VEGF), Wnt Signaling Pathway placental growth factor (PlGF), Foetal Bovine Somatotrophin (FBS), Interleukin 2-(IL2), IL3-, IL4-, IL5-, IL6-, IL7-growth factor.

In yet another embodiment, which may be combined with any of the preceding embodiments the disclosure relates to the production of an Insulin like growth factor 1 or a variant thereof. In its mature form, human IGF-1, also called somatomedin, is a small protein of 70 amino acids that has been shown to stimulate growth of a wide range of cells in culture. The mature protein is initially encoded by three known splice variant mRNAs. The open reading frame of each mRNA encodes a precursor protein containing the 70 amino acid IGF-1 (SEQ ID NO.:16) and a particular E-peptide at the C-terminus, depending on the particular IGF-1 mRNA. These E-peptides have been termed the Ea (SEQ ID NO.: 17), Eb (SEQ ID NO.: 18) and Ec (SEQ ID NO.: 19) peptides and range from 35 to 87 amino acids in length and encompass a common sequence region at the N-terminus and a variable sequence region at the C-terminus. In physiological expression situations the E-peptides are cleaved off of the precursor by endogenous proteases to yield the mature 70 amino acid IGF-1 known to be bioactive. The IGF-1 protein binds the Insulin like growth factor 1 receptor (IGF-1R), Insulin like growth factor 2 receptor (IGF-2R) and the Insulin receptor (INSR). IGF-1 has been manufactured recombinantly on a large scale using both yeast and E. coli. IGF-1 is a poor drug candidate, since this protein is quickly degraded by endogenous proteases in the serum of patients. Different strategies have been applied to overcome said disadvantage. WO05033134 discloses a stabilized IGF-1 protein fused to an immunoglobulin Fc region. WO2007/146689 discloses a stabilized IGF-1 precursor protein wherein the cleavage of the E-peptide from the IGF-1 by a protease is reduced. Although the teaching disclosed in WO2005033134 and WO2007/146689 can be used to stabilize IGF-1 variants in vivo, they do not solve the problem that expression of recombinant IGF-1 or variants thereof in mammalian cells, for example CHO cell lines, results in cell growth inhibition and low titers (see example section).

The teaching of the present invention provides a method for the production of recombinant IGF-1 or variants thereof in mammalian cells, for example a CHO cell, wherein said mammalian cell being deficient in the expression of a functional Insulin like growth factor 1 receptor (IGF-1R), the method comprising
a. Producing a mammalian cell being deficient in the expression of the Insulin like growth factor 1 receptor;
b. Transforming the cell of step a. with an expression vector comprising a nucleic acid molecule encoding an IGF-1 or a variant thereof;
c. Selecting a cell of step b. being transformed;
d. Cultivating the cell selected in step c. under conditions allowing the expression of the IGF-1 or a variant thereof; and
e. Harvesting the IGF-1 or a variant thereof from the mammalian cells cultivated in step d,
wherein alternatively the order of steps a. and b. can be reversed or both steps can be performed at the same time.

In a particular embodiment the above described method comprises the step of processing the isolated therapeutic protein.

In a particular embodiment, the mammalian cell being deficient in the expression of the Insulin like growth factor 1 receptor (IGF-1R), when produced and cultivated as described above in steps a. to e., produces at least 1.5-fold, or 2-fold, or 3-fold, or 4-fold, or 5 fold, or 6-fold, or 7-fold, or 8-fold, or 9-fold, or 10-fold or more higher IGF-1 or a variant thereof than a cell being transformed as described in step b. above, but which has not been modified as described in step a. (not being deficient in the expression of the IGF-1R). In another particular embodiment, the mammalian cell being deficient in the expression of the IGF-1R as described above grow up to $0.5-1\times10^7$ cells/ml or $1-1.5\times10^7$ cells/ml or $1.5-2\times10^7$ cells/ml or $2-2.5\times10^7$ or $3-3.5\times10^7$ cells/ml or higher during the cultivation time. The viability of the mammalian cell being deficient in the expression of the of the IGF-1R is over 97% during the first 80-110 h or 110-140 h or 140-170 h or 170-200 h or 200-230 h or 230-260 h cultivation time.

In an additional embodiment, a culture of the mammalian cell being deficient in the expression of the IGF-1R described and cultured as disclosed herein, produces at least 1 g/L or 1.2 g/L or 1.4 g/L or 1.6 g/L or 1.8 g/L or 2 g/L or 2.2 g/L or 2.4 g/L or 2.6 g/L or 2.8 g/L or 3 g/l or more IGF-1 or a variant thereof.

The production of a mammalian cell being deficient in the expression of a certain gene, e.g. the Insulin like growth factor 1 receptor, including transformation, selection and cultivation of genetically modified cells follows the well-known overall paradigm of classical molecular biology developed for microbial and mammalian systems and is an established technique and well known to the person skilled in the art. CHO knock-out cells have been described in the prior art already at the beginning of this century (see Krämer et al, Appl. Microbiol. Biotechnol. (2010) 88:425-436). The following methods can be used for the production of mammalian cell being deficient in the expression of a certain gene:

Gene Targeting by Homologous Recombination

Homologous recombination is one way to obtain a mammalian cell being deficient in the expression of certain gene (e.g. gene knock-out). Although this technology is in principle more specific than non-targeting methods, the frequency of homologous recombination is very low and is not applicable for industrial cell line engineering (Vasquez K M, Marburger K, Intody Z, Wilson J H (2001) Manipulating the mammalian genome by homologous recombination. Proc Natl Acad Sci USA 98(15): 8403-8410). As a result, screening and analysis of many clones is necessary to identify a knock out cell. A successful example of this procedure is the knockout of the α1,6-fucosyltransferase in CHO-DG44 cells (Yamane-Ohnuki N, Kinoshita S, Inoue-Urakubo M, Kusunoki M, Iida S, Nakano R, Wakitani M, Niwa R, Sakurada M, Uchida K, Shitara K, Satoh M (2004) Establishment of FUT8 knockout Chinese hamster ovary cells: an ideal host cell line for producing completely defucosylated antibodies with enhanced antibody dependent cellular cytotoxicity. Biotechnol Bioeng 87(5):614-622).

Double strand breaks can be introduced by meganucleases to raise the occurrence of Homologous Recombination. Meganucleases (homing endonucleases) recognize long DNA sequences of 12-45 bp (Pâques F, Duchateau P (2007) Meganucleases and DNA double-strand break-induced recombination: perspectives for gene therapy. Curr Gene Ther 7(1):49-66). I-SceI and I-CreI are meganucleases which have been studied intensively (Epinat J C, Arnould S, Chames P, Rochaix P, Desfontaines D, Puzin C, Patin A, Zanghellini A, Pâques F, Lacroix E (2003) A novel engineered meganuclease induces homologous recombination in yeast and mammalian cells. Nucleic Acids Res 31(11):2952-2962).

Double Strand Breaks Introduced by Engineered Meganucleases

Meganucleases are endodeoxyribonucleases characterized by a large recognition site (12 to 40 base pairs); as a result this site generally occurs only once in any given genome. Meganucleases are "molecular DNA scissors" that can be used to replace, eliminate or modify sequences in a highly targeted way. By modifying their recognition sequence through protein engineering, the targeted sequence can be changed. The best characterized endonucleases which are most widely used in research and genome engineering include I-SceI, I-CreI and I-DmoI. Most meganucleases are homodimers or internally symmetrical monomers. The DNA binding site, which contains the catalytic domain, is composed of two parts on either side of the cutting point.

To date, about 600 meganucleases, from various unicellular organisms, have been identified and sequenced. This implies that the number of recognizable DNA sequences is very limited for genome customization applications. To overcome this limitation companies as e.g. Cellectis engineer meganucleases in a way that they are specific to the targeted site for each gene of interest. The high specificity of meganucleases gives them a high degree of precision and low cell toxicity.

After a DNA double strand breaks has occurred (e.g. by using a meganuclease) "Non Homologous End-Joining" is occurring. "Non Homologous End-Joining" is a cell natural process that repairs double strand breaks in DNA. The broken DNA ends are directly re-ligated without the need for a homologous template, in contrast to Homologous Recombination. Due to the error-prone nature of "Non Homologous End-Joining", a proportion of double strand breaks will be misrepaired by the addition and/or deletion of nucleotides. These mutations within the genomic sequence occur at the site of the double strand break, resulting in the loss of gene function and therefore achieving gene knock-out.

Double Strand Breaks Introduced by Zinc-finger Nucleases

Zinc-finger nucleases are very useful tools to produce mammalian knock out cells. A zinc finger nuclease is composed of an engineered zinc-finger domain, a short linker and a modified FokI endonuclease domain introducing sequence specific DNA double stand break. By changing residues in the zinc-finger domain new zinc-finger nucleases with different DNA-binding specificities can be produced (Bibikova M, Beumer K, Trautman J K, Carroll D (2003) Enhancing gene targeting with designed zinc finger nucleases. Science 300 (5620):764; Cathomen T, Joung J K (2008) Zinc-finger nucleases: the next generation emerges. Mol Ther 16(7):1200-1207). The zinc-finger domains direct the cleavage position, an advantage over other gene targeting processes because zinc-finger nucleases can be designed to target any desired genomic site. The skilled person is aware of the great number of scientific publications dealing with zinc finger nucleases and their application in gene targeting (Rémy S, Tesson L, Ménoret S, Usal C, Scharenberg A M, Anegon I (2010) Zinc-finger nucleases: a powerful tool for genetic engineering of animals. Transgenic Res 19(3):363-371; Krämer et al, Appl. Microbiol. Biotechnol. (2010) 88:425-436; Kandavelou K, Ramalingam S, London V, Mani M, Wu J, Alexeev V, Civin C I, Chandrasegaran S (2009) Targeted manipulation of mammalian genomes using designed zinc finger nucleases. Biochem Biophys Res Commun 388(1):56-61; Urnov F D, Miller J C, Lee Y L, Beausejour C M, Rock J M, Augustus S, Jamieson A C, Porteus M H, Gregory P D, Holmes M C (2005) Highly efficient endogenous human gene correction using designed zinc-finger nucleases. Nature 435(7042):646-651).

A DNA double strand break catalyzed by the zinc finger nucleases can activate two different DNA repair pathways, namely the homologous recombination or the non-homologous end joining. The homologous recombination is preferably activated if high amounts of an appropriate donor DNA are available and allows the introduction of new DNA into the genome (Bibikova M, Beumer K, Trautman J K, Carroll D (2003) Enhancing gene targeting with designed zinc finger nucleases. Science 300 (5620):764)).

The non-homologous end joining of DNA repairs simply rely on re-ligation of the broken DNA ends. In some cases insertions or deletions of nucleotides may occur and will then lead to a different sequence compared to the original segment. Frame shifts or nonsense codons are the consequence, yielding truncated or aberrant mRNA during transcription. Customized zinc finger nucleases can be produced in several ways (Beerli R R, Barbas C F 3rd (2002) Engineering polydactyl zinc-finger transcription factors. Nat Biotechnol 20(2):135-141); Foley J E, Yeh J R, Maeder M L, Reyon D, Sander J D, Peterson R T, Joung J K (2009) Rapid mutation of endogenous zebrafish genes using zinc finger nucleases made by Oligomerized Pool ENgineering (OPEN). PLoS ONE 4(2):e4348). Customized zinc finger nucleases can be purchased from Sangamo Biosciences/Sigma-Aldrich. The principles of generating zinc finger nucleases are disclosed in Cathomen T, Joung J K (2008) Zinc-finger nucleases: the next generation emerges. Mol Ther 16(7):1200-12078). Another approach makes use of the freely accessible oligomerized pool engineering (OPEN) platform provided by the "Zinc Finger Consortium" (www.zincfingers.org). This platform uses a zinc-finger pool archive, which is recombined based on the target DNA sequence. Afterwards, the recombined zinc fingers are screened via a bacterial two-hybrid system. A successful binding is measured by the expression of a reporter gene (Maeder M L, Thibodeau-Beganny S, Osiak A, Wright D A, Anthony R M, Eichtinger M, Jiang T, Foley J E, Winfrey R J, Townsend J A, Unger-Wallace E, Sander J D, Müller-Lerch F, Fu F, Pearlberg J, Göbel C, Dassie J P, Pruett-Miller S M, Porteus M H, Sgroi D C, Iafrate A J, Dobbs D, McCray P B Jr, Cathomen T, Voytas D F, Joung J K (2008) Rapid "open-source" engineering of customized zinc-finger nucleases for highly efficient gene modification. Mol Cell 31(2): 294-301 Foley et al. 2009; Maeder et al. 2008). The zinc-finger technology has already been applied successfully in cell line engineering as shown in Table 1 of Krämer et al, Appl. Microbiol. Biotechnol. (2010) 88:425-436.

Transcription activator-like effector nucleases (TALENs) are artificial restriction enzymes generated by fusing the TAL effector DNA binding domain to a DNA cleavage domain. TAL effectors are proteins secreted by *Xanthomonas* bacteria. The DNA binding domain contains a highly conserved 33-34 amino acid sequence with the exception of the 12th and 13th amino acids. These two locations are highly variable and show a strong correlation with specific nucleotide recognition. This simple relationship between amino acid sequence and DNA recognition has allowed for the engineering of specific DNA binding domains by selecting a combination of repeat segments containing the appropriate Repeat Variable Diresidue (RVD). The mechanism of DNA recognition of a TALE is therefore based on a simple code whereby one RVD recognizes one nucleotide of DNA sequence and ensures that the DNA binding domain of each TALE is capable of targeting large recognition sites with high precision (15-30 nt). The second component of a TAL Effector Nuclease is the catalytic domain of an endonuclease that introduces DNA Double Strand Breaks and which is fused to the TALE DNA-binding domain (FokI). TALENs function in pairs and are therefore heterodimers composed of two highly sequence-specific TALEN units. These units bind target DNA sequences and create a spacer region to allow the endonuclease domains to dimerize and create a DNA double strand break. Following DNA cleavage, DNA double strand break are repaired by Non-Homologous End-Joining (NHEJ). NHEJ repairs by joining the two ends together leading in some instances to a deletion or insertion of base-pairs, producing frameshift and preventing the production of the protein.

Recombinant adeno-associated virus (rAAV) based genome engineering is a genome editing platform centered around the use of rAAV vectors that enables insertion, deletion or substitution of DNA sequences into the genomes of mammalian cells. The technique builds on the discovery that homologous recombination, a natural DNA repair mechanism, can be harnessed to perform precise genome alterations. The technique has been adopted for use in engineering cell lines to optimize bio producer cell lines for bio manufacturing of proteins.

The rAAV genome is built of single-stranded deoxyribonucleic acid which is about 4.7 kilo base long. These single-stranded DNA viral vectors have high transduction rates and have a unique property of stimulating endogenous HR without causing double strand DNA breaks in the genome as e.g. in ZFN or TALEN technology. rAAV vector can be designed to any target genomic locus and perform e.g. gene knock-outs. rAAV targets a single allele at a time.

Another option to repress genes are TAL repressors which were reported e.g. by Garg A, Lohmueller J J, Silver P A, Armel T Z. (Nucleic Acids Res. 2012 August; 40(15):7584-95. Engineering synthetic TAL effectors with orthogonal target sites) and Zhang F, Cong L, Lodato S, Kosuri S, Church G M, Arlotta P (Nat Biotechnol. 2011 February; 29(2):149-53. Efficient construction of sequence-specific TAL effectors for modulating mammalian transcription) who created TAL effectors fused with the KRAB or SID transcriptional repression domain. It was shown that KRAB placed on both termini or on the N- or C-terminus of the TAL DNA-binding domain exhibited over 90% repression of a reporter plasmid.

Hence, another aspect of the disclosure relates to a method for producing a therapeutic protein, as disclosed above, wherein the cell being deficient in the expression of the cognate receptor of said therapeutic protein has been produced by applying targeted genetic recombination technologies.

RNA Interference

RNAi processes have been described in the prior art in great detail:

Carthew R W, Sontheimer E J (2009) Origins and mechanisms of miRNAs and siRNAs. Cell 136(4):642-655;

Dykxhoorn D M, Novina C D, Sharp P A (2003) Killing the messenger: short RNAs that silence gene expression. Nat Rev Mol Cell Biol 4(6):457-467;

Kim D H, Rossi J J (2007) Strategies for silencing human disease using RNA interference. Nat Rev Genet 8(3):173-184;

Siomi H, Siomi M C (2009) On the road to reading the RNA interference code. Nature 457(7228): 396-404;

Wu S C (2009) RNA interference technology to improve recombinant protein production in Chinese hamster ovary cells. Biotechnol Adv 27(4):417-422.

Elbashir S M, Harborth J, Lendeckel W, Yalcin A, Weber K, Tuschl T (2001) Duplexes of 21-nucleotide RNAs mediate RNA interference in cultured mammalian cells. Nature 411 (6836): 494-498.

Brummelkamp T R, Bernards R, Agami R (2002) A system for stable expression of short interfering RNAs in mammalian cells. Science 296(5567):550-553.

For example, siRNAs were used to silence in CHO cells the protein Requiem, a protein which relevant in the apoptosis cascade (Wong D C, Wong K T, Nissom P M, Heng C K, Yap M G (2006b) Targeting early apoptotic genes in batch and fed-batch CHO cell cultures. Biotechnol Bioeng 95(3): 350-361) and the caspases 3 and 7 (Sung Y H, Lee J S, Park S H, Koo J, Lee G M (2007) Influence of co-downregulation of caspase-3 and caspase-7 by siRNAs on sodium butyrate-induced apoptotic cell death of Chinese hamster ovary cells producing thrombopoietin. Metab Eng 9(5-6): 452-464).

In a particular embodiment the disclosure relates to one of the above described methods, wherein the deficiency in the expression of the cognate receptor of said therapeutic protein, which may be a recombinant therapeutic protein, e.g. the Insulin like growth factor 1 receptor if the therapeutic protein of interest is the IGF-1 protein or a variant thereof, in the mammalian cell has been achieved by applying RNA-interference, the method comprising:

(a) introducing into said cell a double-stranded ribonucleic acid (dsRNA), wherein the dsRNA comprises at least two sequences that are complementary to each other and wherein a sense strand comprises a first sequence and an antisense strand comprises a second sequence comprising a region of complementarity which is substantially complementary to at least a part of the mRNA encoding the cognate receptor of the therapeutic protein, e.g. the IGF-1R, and wherein said region of complementarity is less than 30 nucleotides in length and wherein said dsRNA upon introduction into said cell inhibits expression of the gene encoding the cognate receptor of the therapeutic protein, e.g. the IGF-1R gene by at least 40%; and (b) maintaining the cell produced in step (a) for a time sufficient to obtain degradation of the mRNA transcript of the gene encoding the cognate receptor of the therapeutic protein thereby inhibiting expression of said receptor, e.g. the IGF-1R, in the cell.

The terms "silence" and "inhibit the expression of", in as far as they refer to the IGF-1R gene, refer to the at least partial suppression of the expression of IGF-1R in a cell treated with dsRNA or shRNA targeting IGF-1R, as manifested by a reduction of the amount of mRNA transcribed or available compared to normal (untreated) cells. This measurement may be determined by comparing mRNA levels in treated cells (which may be isolated from a first cell or group of cells which have been treated such that the expression of the IGF-1R gene is inhibited), as compared to a second cell or group of cells substantially identical to the first cell or group of cells but which has or have not been so treated (control cells). The degree of inhibition is usually expressed in terms of $$\frac{(mRNA \text{ in control cells}) - (mRNA \text{ in treated cells})}{(mRNA \text{ in control cells})} \cdot 100\%$$

Alternatively, the degree of inhibition may be given in terms of a reduction of a parameter that is functionally linked to gene transcription, e.g. the amount of polypeptide, or the number of cells displaying a certain phenotype associated with IGF-1R. For example, in certain instances, expression of the IGF-1R gene is inhibited, when it is suppressed by at least about 20%, 25%, 35%, or 50% by administration of an IGF-1R specific dsRNA or shRNA. In some embodiments, the IGF-1R gene is suppressed by at least about 60%, 70%, or 80% by administration of an IGF-1R specific dsRNA or shRNA. In some embodiments, IGF-1R gene is suppressed by at least about 85%, 90%, or 95% by administration of an IGF-1R specific dsRNA or shRNA.

The dsRNA comprises two RNA strands that are sufficiently complementary to hybridize to form a duplex structure. One strand of the dsRNA (the antisense strand) comprises a region of complementarity that is substantially complementary, and generally fully complementary, to a target sequence, derived from the sequence of gene product of the IGF-1R gene, the other strand (the sense strand) comprises a region which is complementary to the antisense strand, such that the two strands hybridize and form a duplex structure when combined under suitable conditions. Generally, the duplex structure is between 15 and 30, more generally between 18 and 25, yet more generally between 19 and 24, and most generally between 19 and 21 base pairs in length. Similarly, the region of complementarity to the target sequence is between 15 and 30, more generally between 18 and 25, yet more generally between 19 and 24, and most generally between 19 and 21 nucleotides in length. The dsRNA may be blunt ended (e.g. where each nucleotide on either strand has a nucleotide suitable for base-pairing on the other strand), or it may further comprise one or more single-stranded nucleotide overhang(s), commonly on the 3' end. The dsRNA can be synthesized by standard methods known in the art as further discussed below, e.g., by use of an automated DNA synthesizer, such as are commercially available from, for example, Biosearch, Applied Biosystems, Inc.

In an additional embodiment, the deficiency in the expression of the Insulin like growth factor 1 receptor as described above has been achieved by using double stranded short interference RNA (siRNA) molecules, wherein the sequence of the sense strand of said siRNAs comprises a sequence selected from the group consisting of SEQ ID NOs.: 1, and 3.

In an additional embodiment, the deficiency in the expression of the Insulin like growth factor 1 receptor has been achieved by using small hairpin RNA (shRNA) molecules, wherein the sequence of said shRNA molecules is selected from the group consisting of SEQ ID NO.: 5, 6, 7, 8, 9 and 10.

Targeted genetic recombination technologies or RNA interference approaches as disclosed herein or those described in the above mentioned prior art can be applied to produce a recombinant mammalian cell, e.g. a CHO cell, deficient in the expression of the cognate receptor of a therapeutic protein, which may be a recombinant therapeutic protein, of interest, e.g. a growth factor like the Insulin like growth factor 1 receptor (see example section).

Production of Transgenic Mammalian Cells

The skilled person knows how to transform, select and cultivate genetically modified mammalian cells, e.g. CHO cells, like CHO-K1 derivative, CHO-DUXB11 derivative or CHO-DG44 cells. Selection protocols are routinely used to facilitate selection of cells that are likely to have integrated the recombinant DNA encoding the desired therapeutic protein, like growth factors, e.g. IGF-1. Antibiotic resistance or the ability to grow in a nutritionally selective medium conferred by a gene co-integrated on the transformation vector is routinely used (see Weber, W. and Fussenegger, M. (2003) Inducible gene expression in mammalian cells, in Gene transfer and expression in mammalian cells, (Makrides, S. C., Ed.), Elsevier: Amsterdam, pp. 589-604) (Efficient selection for high-expression transfectants with a novel eukaryotic vector: Niwa Hitoshi, Yamamura Ken-ichi, Miyazaki Jun-ichi). The two most common CHO expression systems for recombinant protein production utilize dihydrofolate reductase (DHFR)-based methotrexate (MTX) selection or glutamine synthetase (GS)-based methionine sulfoximine (MSX) selection (Rita Costa A, Elisa Rodrigues M, Henriques M, Azeredo J, Oliveira R. Eur J Pharm Biopharm. 2010 February; 74(2):127-38. Epub 2009 Oct. 22. Guidelines to cell engineering for monoclonal antibody production).

The integration site of the foreign DNA clearly influences the level of expression. Integration of the foreign genes into highly transcriptionally active regions of the genome using the Crew/loxP system have been described (Kwaks, T. and Otte, A. (2006) Employing epigenetics to augment the expression of therapeutic proteins in mammalian cells. Trends Biotechnol., 24(3), 137-142). Assuming that integration of any foreign trans gene to this specific site will yield high producing clones, targeted integration can be achieved via reciprocal site specific integration (Baer, A. and Bode, J. (2001) Coping with kinetic and thermodynamic barriers: RMCE, an efficient strategy for the targeted integration of transgenes. Curr. Opin. Biotechnol., 12, 473-480).

Additionally, short nucleotide sequences that help the foreign DNA to be more transcriptionally active regardless of its site of integration have been linked to the transgenes. The STAR elements (Stabilizing and Anti-repressor elements) reduce the extent of histone de-acetylation pattern and the spread of methylation in the vicinity of the inserted trans genes (Kwaks, T.; Barnett, P.; Hemrika, W.; Siersma, T.; Sewalt, R. Satijn, D.; Brons, J.; van Blokland, R.; Kruckeberg, A.; Kelder, A. and Otte, W. (2003) Identification of anti-repressor elements that confer high and stable protein production in mammalian cells. Nat. Biotechnol., 21, 553-558). The Scaffold/Matrix Associated Regions interact with the nuclear matrix and create loops where gene expression is coordinated and insulated from repression (Girod, P.; Zahn-Zabal, M. and Mermod, N. (2005) MAR elements as tools to increase protein production by CHO cells, in Animal cell technology meets genomics; Godia, M. F. and Fussenegges, M., Ed., Springer: Amsterdam, pp. 411-415; Girod, P.; Zahn-Zabal, M. and Mermod, N. (2005) Use of the chicken lysozyme 5' matrix attachment region to generate high producer CHO cell lines. Biotechnol. Bioeng., 91(1), 1-11), while the UCOE elements (Ubiquitous Chromatin Opening Elements) create a highly transcriptionally active environment [(Benton, T.; Chen, T.; McEntree, M.; Fox, B.; King, D.; Crombie, R.; Thomas, T. and Bebbington, C. (2002) The use of UCOE vectors in combination with a preadapted serum free, suspension cell line allows for rapid production of large quantities of protein. Cytotechnology, 38, 43-46.)

Vectors particularly suitable for producing polypeptides in mammalian cells, particularly rodent cells such as CHO and DHFR gene defective CHO cells have been disclosed in the patent application WO09080720A. There are several appropriate methods known in the prior art for introducing an expression vector into a mammalian host cell. Respective methods include but are not limited to calcium phosphate transfection, electroporation, lipofection, biolistic- and polymer-mediated genes transfer. Suitable host cells are described above. After introduction of the expression vector nucleic acid into the host cell(s), the obtained transformants are cultured under selective conditions suitable for assaying the expression of the mammalian selectable marker gene enclosed in the expression cassette (MSM). This means, that for example when the mammalian selectable marker gene is an antibiotic resistance gene, transformants are cultured in a medium containing the corresponding antibiotic active in mammalian cells and the transformants which are viable under such conditions are selected, thus enabling the obtainment of transformants which express the marker gene and thus incorporated the vector. Additionally, a second selection step may be performed by culturing the transformants in a selection medium adapted for selecting the amplifiable, selectable marker gene comprised in the expression cassette (MASM). E.g. in case DHFR is used as an amplifiable, selectable marker gene, the transformants can be cultured in a nucleotide or purine-free medium in the presence of a DHFR inhibitor. In case an inducible promoter is used in at least one expression cassette, a corresponding induction signal should be provided in order to commence expression of the polypeptide. In order to make use of the DHFR selection/amplification system, said host cells may be cultured in the presence of a DHFR inhibitor. Suitable DHFR inhibitors are antifolates such as e.g. MTX. The concentration of antifolate/MTX used depends on the host cell and the DHFR variant incorporated in the vector. The concentration range can be chosen for multistep amplification procedures in DHFR" host cells for example at values around 5 nM-20 nM ranging to values of 500 nM to 1000 nM or even higher for secondary or further amplification steps. For DHFR+ cells starting concentrations are usually higher in the range of 100 nM to 750 nM, preferably 500 nM in the first steps and 500 nM to 1000 nM and above for further amplification steps. Suitable DHFR variants are described above.

In order to make use of the GS selection/amplification system said host cells may be cultured in the presence of e.g. MSX. The concentration of MSX used depends on the host cell. The concentration range can be chosen between from about 15 to 150 micro M, 20 to 100 micro M and 25 to 50 micro M. These ranges are particularly suitable for NSO and CHO cells.

In a next step, the therapeutic protein can be isolated/harvested from the cell culture. The therapeutic protein may be obtained by disrupting the host cells. The therapeutic protein may also be expressed, e.g. secreted into the culture medium and can be obtained therefrom. Also combinations of the respective methods are possible. Thereby, products, in particular polypeptides can be produced and obtained/isolated efficiently with high yield. The obtained therapeutic protein may also be subject to further processing steps such as e.g. purification and/or modification steps in order to produce the product of interest in the desired quality.

According to one alternative, said polypeptide of interest is secreted into the cell culture medium and subsequently isolated from the cell culture medium.

The CHO cells have been cultivated and harvested according to standard methods known to the person skilled in the art (e.g. Curr. Protoc. Protein Sci. 2001 May; Chapter 5: Unit5.10. Production of recombinant proteins in mammalian cells. Chen S, Gray D, Ma J, Subramanian S.; CHO cultivation media are furthermore described in Journal of Biotechnology, Volume 108, Issue 3, 18 Mar. 2004, Pages 279-292: Serum- and protein-free media formulations for the Chinese hamster ovary cell line DUKXB11. Martin Schröder, Kathrin Matischak, Peter Friedl.

In an additional embodiment the disclosure relates to the above described methods, wherein the Insulin like growth factor 1 protein is the human Insulin like growth factor 1 protein (SEQ ID NO.: 16) or a variant thereof. For example, such sequences include but are not limited to the following sequences:

Examples of such molecules include, but are not limited to, the following polypeptides:

A polypeptide comprising a human IGF-1 Ea-peptide precursor protein wherein the amino acid G42 is substituted by the amino acid serine and wherein the amino acid(s)

(1) G1, P2, E3 are deleted, amino acid R36 is substituted or deleted and the amino acids R71 and S72 are deleted.
(2) G1, P2, E3 are deleted, amino acid R36 is substituted by glutamine (Q) and the amino acids R71 and S72 are deleted.
(3) G1, P2, E3 are deleted, amino acid R37 is substituted or deleted and the amino acids R71 and S72 are deleted.
(4) G1, P2, E3 are deleted, amino acid R37 is substituted by glutamic acid (E) and the amino acids R71 and S72 are deleted.
(5) G1, P2, E3 are deleted, amino acid R37 is substituted by alanine and the amino acids R71 and S72 are deleted.
(6) G1, P2, E3 are deleted, amino acid R37 is substituted by Proline (P) and the amino acids R71 and S72 are deleted.
(7) G1, P2, E3 are deleted, amino acids R36 and R37 are substituted or deleted and the amino acids R71 and S72 are deleted.
(8) G1, P2, E3 are deleted, amino acid R36 and R37 are both substituted by glutamine (Q) and the amino acids R71 and S72 are deleted.
(9) G1, P2, E3 are deleted, amino acid R36 is substituted by glutamine (Q), R37 is substituted by alanine and the amino acids R71 and S72 are deleted.
(10) G1, P2, E3 are deleted, amino acid R36 is substituted or deleted and the amino acids R71 and S72 are deleted and amino acid R77 is mutated to glutamine (Q).
(11) G1, P2, E3 are deleted, amino acid R36 is substituted or deleted and the amino acids R71 and S72 are deleted and amino acids R74 and R77 are mutated to glutamine (Q).
(12) G1, P2, E3 are deleted, amino acid R36 is substituted or deleted and the amino acids R71 and S72 are deleted and amino acids R74, R77 and Q104 are mutated to glutamine (Q).
(13) G1, P2, E3 are deleted, amino acid R36 is substituted by glutamine (Q) and the amino acids R71 and S72 are deleted and amino acid R74 is mutated to glutamine (Q).
(14) G1, P2, E3 are deleted, amino acid R36 is substituted by glutamine (Q) and the amino acids R71 and S72 are deleted and amino acids R74 and R77 are mutated to glutamine (Q).
(15) G1, P2, E3 are deleted, amino acid R36 is substituted by glutamine (Q) and the amino acids R71 and S72 are deleted and amino acids R74, R77 and R104 are mutated to glutamine (Q).
(16) G1, P2, E3 are deleted, amino acid R37 is substituted by glutamic acid (E) and the amino acids R71 and S72 are deleted and amino acid R77 is mutated to glutamine (Q).
(17) G1, P2, E3 are deleted, amino acid R37 is substituted by glutamic acid (E) and the amino acids R71 and S72 are deleted and amino acids R74 and R77 are mutated to glutamine (Q).
(18) G1, P2, E3 are deleted, amino acid R37 is substituted by glutamic acid (E) and the amino acids R71 and S72 are deleted and amino acids R74, R77 and R104 are mutated to glutamine (Q).
(19) G1, P2, E3 are deleted, amino acid R37 is substituted by alanine (A) and the amino acids R71 and S72 are deleted and amino acid R74 is mutated to glutamine (Q).
(20) G1, P2, E3 are deleted, amino acid R37 is substituted by alanine (A) and the amino acids R71 and S72 are deleted and amino acids R74 and R77 are mutated to glutamine (Q).
(21) G1, P2, E3 are deleted, amino acid R37 is substituted by alanine (A) and the amino acids R71 and S72 are deleted and amino acids R74, R77 and R104 are mutated to glutamine
(22) G1, P2, E3 are deleted, amino acid R37 is substituted by Proline (P) and the amino acids R71 and S72 are deleted and amino acid R74 is mutated to glutamine (Q).
(23) G1, P2, E3 are deleted, amino acid R37 is substituted by Proline (P) and the amino acids R71 and S72 are deleted and amino acids R74 and R77 are mutated to glutamine (Q).
(24) G1, P2, E3 are deleted, amino acid R37 is substituted by Proline (P) and the amino acids R71 and S72 are deleted and amino acids R74, R77 and R104 are mutated to glutamine
(25) G1, P2, E3 are deleted, amino acid R36 and R37 are both substituted by glutamine (Q) and the amino acids R71 and S72 are deleted and amino acid R74 is mutated to glutamine (Q).
(26) G1, P2, E3 are deleted, amino acid R36 and R37 are both substituted by glutamine (Q) and the amino acids R71 and S72 are deleted and amino acids R74 and R77 are mutated to glutamine (Q).
(27) G1, P2, E3 are deleted, amino acid R36 is substituted by glutamine (Q), R37 is substituted by alanine and the amino acids R71 and S72 are deleted and amino acids R74 and R77 are mutated to glutamine (Q).
(28) G1, P2, E3 are deleted, amino acid R36 and R37 are both substituted by glutamine (Q) and the amino acids R71 and S72 are deleted and amino acids R74, R77 and R104 are mutated to glutamine (Q).
(29) G1, P2, E3 are deleted, amino acid R36 is substituted by glutamine (Q), R37 is substituted by alanine and the amino acids R71 and S72 are deleted and amino acids R74, R77 and R104 are mutated to glutamine (Q).
(1a) G1, P2, E3 are deleted, amino acid R36 is substituted or deleted and the amino acids K68, S69, A70, R71 and S72 are deleted.
(2a) G1, P2, E3 are deleted, amino acid R36 is substituted by glutamine (Q) and the amino acids K68, S69, A70, R71 and S72 are deleted.
(3a) G1, P2, E3 are deleted, amino acid R37 is substituted or deleted and the amino acids K68, S69, A70, R71 and S72 are deleted.
(4a) G1, P2, E3 are deleted, amino acid R37 is substituted by glutamic acid (E) and the amino acids K68, S69, A70, R71 and S72 are deleted.
(5a) G1, P2, E3 are deleted, amino acid R37 is substituted by alanine and the amino acids K68, S69, A70, R71 and S72 are deleted.
(6a) G1, P2, E3 are deleted, amino acid R37 is substituted by Proline (P) and the amino acids K68, S69, A70, R71 and S72 are deleted.
(7a) G1, P2, E3 are deleted, amino acids R36 and R37 are substituted or deleted and the amino acids K68, S69, A70, R71 and S72 are deleted.
(8a) G1, P2, E3 are deleted, amino acid R36 and R37 are both substituted by glutamine (Q) and the amino acids K68, S69, A70, R71 and S72 are deleted.
(9a) G1, P2, E3 are deleted, amino acid R36 is substituted by glutamine (Q), R37 is substituted by alanine and the amino acids K68, S69, A70, R71 and S72 are deleted.
(10a) G1, P2, E3 are deleted, amino acid R36 is substituted or deleted and the amino acids K68, S69, A70, R71 and S72 are deleted and amino acid R74 is mutated to glutamine (Q).
(11a) G1, P2, E3 are deleted, amino acid R36 is substituted or deleted and the amino acids K68, S69, A70, R71 and S72 are deleted and amino acids R74 and R77 are mutated to glutamine (Q).
(12a) G1, P2, E3 are deleted, amino acid R36 is substituted or deleted and the amino acids K68, S69, A70, R71 and S72 are deleted and amino acids R74, R77 and Q104 are mutated to glutamine (Q).
(13a) G1, P2, E3 are deleted, amino acid R36 is substituted by glutamine (Q) and the amino acids K68, S69, A70, R71 and S72 are deleted and amino acid R74 is mutated to glutamine (Q).
(14a) G1, P2, E3 are deleted, amino acid R36 is substituted by glutamine (Q) and the amino acids K68, S69, A70, R71 and S72 are deleted and amino acids R74 and R77 are mutated to glutamine (Q).
(15a) G1, P2, E3 are deleted, amino acid R36 is substituted by glutamine (Q) and the amino acids K68, S69, A70, R71 and S72 are deleted and amino acids R74, R77 and R104 are mutated to glutamine (Q).
(16a) G1, P2, E3 are deleted, amino acid R37 is substituted by glutamic acid (E) and the amino acids K68, S69, A70, R71 and S72 are deleted and amino acid R74 is mutated to glutamine (Q).
(17a) G1, P2, E3 are deleted, amino acid R37 is substituted by glutamic acid (E) and the amino acids K68, S69, A70, R71 and S72 are deleted and amino acids R74 and R77 are mutated to glutamine (Q).
(18a) G1, P2, E3 are deleted, amino acid R37 is substituted by glutamic acid (E) and the amino acids K68, S69, A70, R71 and S72 are deleted and amino acids R74, R77 and R104 are mutated to glutamine (Q).
(19a) G1, P2, E3 are deleted, amino acid R37 is substituted by alanine (A) and the amino acids K68, S69, A70, R71 and S72 are deleted and amino acid R74 is mutated to glutamine (Q).
(20a) G1, P2, E3 are deleted, amino acid R37 is substituted by alanine (A) and the amino acids K68, S69, A70, R71 and S72 are deleted and amino acids R74 and R77 are mutated to glutamine (Q).
(21a) G1, P2, E3 are deleted, amino acid R37 is substituted by alanine (A) and the amino acids K68, S69, A70, R71 and S72 are deleted and amino acids R74, R77 and R104 are mutated to glutamine
(22a) G1, P2, E3 are deleted, amino acid R37 is substituted by Proline (P) and the amino acids K68, S69, A70, R71 and S72 are deleted and amino acid R74 is mutated to glutamine (Q).
(23a) G1, P2, E3 are deleted, amino acid R37 is substituted by Proline (P) and the amino acids K68, S69, A70, R71 and S72 72 are deleted and amino acids R74 and R77 are mutated to glutamine (Q).
(24a) G1, P2, E3 are deleted, amino acid R37 is substituted by Proline (P) and the amino acids K68, S69, A70, R71 and S72 are deleted and amino acids R74, R77 and R104 are mutated to glutamine
(25a) G1, P2, E3 are deleted, amino acid R36 and R37 are both substituted by glutamine (Q) and the amino acids K68, S69, A70, R71 and S72 are deleted and amino acid R74 is mutated to glutamine (Q).
(26a) G1, P2, E3 are deleted, amino acid R36 and R37 are both substituted by glutamine (Q) and the amino acids K68, S69, A70, R71 and S72 are deleted and amino acids R74 and R77 are mutated to glutamine (Q).
(27a) G1, P2, E3 are deleted, amino acid R36 is substituted by glutamine (Q), R37 is substituted by alanine and the amino acids K68, S69, A70, R71 and S72 are deleted and amino acids R74 and R77 are mutated to glutamine (Q).
(28a) G1, P2, E3 are deleted, amino acid R36 and R37 are both substituted by glutamine (Q) and the amino acids K68, S69, A70, R71 and S72 are deleted and amino acids R74, R77 and R104 are mutated to glutamine (Q).
(29a) G1, P2, E3 are deleted, amino acid R36 is substituted by glutamine (Q), R37 is substituted by alanine and the amino acids K68, S69, A70, R71 and S72 are deleted and amino acids R74, R77 and R104 are mutated to glutamine (Q).

Additionally, an IGF-1 variant which could be produced according to the disclosed method is one of the above described polypeptides (1)-(29a), wherein said molecules instead of being mutated at the positions 1-3, only the amino acid E3 is deleted (e.g. the molecule (28a) could also refer to a polypeptide comprising a human IGF-1 Ea-peptide precursor protein wherein the amino acid G42 is substituted by the amino acid serine and wherein the amino acid E3 is deleted, amino acid R36 and R37 are both substituted by glutamine (Q), the amino acids K68, S69, A70, R71 and S72 are deleted and amino acids R74, R77 and R104 are mutated to glutamine (Q).)

Additionally, an IGF-1 variant which could be produced according to the disclosed method is a polypeptide containing a human IGF-1 precursor protein, i.e. comprising the Ea-peptide from human IGF-1, which is fused to an immunoglobulin Fc region and wherein the amino acid glycine at position 42 is substituted by another amino acid and wherein the numbering of the amino acids corresponds to SEQ ID NO.: 16. The E-peptide may be the Ea, Eb, or Ec peptide (SEQ ID NOs.: 17-19) and the amino acid by which the glycine at position 42 is substituted isserine.

Thus, in one embodiment, an IGF-1 variant which could be produced according to the disclosed method is a polypeptide comprising a human IGF-1 precursor protein; (a) wherein the amino acid G42 is substituted by the amino acid serine; and (b) which is linked to an immunoglobulin Fc region, particularly a modified Fc region, particularly an Fc region, which is modified to modulate its binding to Fc receptor. For example, one or more amino acids can be replaced with a different amino acid residue such that the Fc region has an altered affinity for the Fc receptor or the C1 component of complement. So called silenced immunglobuline Fc regions have been described in the art: LALA and N297A (Strohl, W., 2009, Curr. Opin. Biotechnol. vol. 20(6):685-691); and D265A (Baudino et al., 2008, J. Immunol. 181: 6664-69; Strohl, W., supra). Examples of silent Fc IgG1 antibodies comprise the so-called LALA mutant comprising L234A and L235A mutation in the IgG1 Fc amino acid sequence. Another example of a silent IgG1 antibody comprises the D265A mutation. Another silent IgG1 antibody comprises the N297A mutation, which results in aglycosylated/non-glycosylated antibodies.

The above mentioned LALA approach is described in further detail in U.S. Pat. No. 5,624,821 and U.S. Pat. No. 5,648,260 both by Winter et al. Thus in one embodiment the disclosed hIGF-1 precursor protein is fused to an Fc region comprising the L234A and L235A mutation or the D265A mutation or the N297A mutation. Such Fc LALA, D265A or N297A constructs have reduced ADCC activity Thus, in one embodiment, an IGF-1 variant which could be produced according to the disclosed method is a polypeptide containing a human IGF-1 Ea-peptide precursor protein fused to an immunoglobulin Fc region, wherein the amino acid glycine at position 42 is substituted by serine, wherein the variant further comprises additional deletions and/or mutations at amino acids G1, P2, E3, R36, R37, K68, S69, A70, R71, S72, R74, R77, G96, S97, A98, G99, N100, K101, N102, Y103, Q104 and/or M105, and wherein the numbering of the amino acids corresponds to SEQ ID NO.: 20.

Examples of such molecules include, but are not limited to, the following polypeptides:

A polypeptide containing a human IGF-1 Ea-peptide precursor protein fused to an immunoglobulin Fc region wherein the amino acid glycine at position 42 is substituted by the amino acid serine, wherein the numbering of the amino acids corresponds to SEQ ID NO.: 20, and wherein the amino acid(s)

(1b) G1, P2, E3 are deleted, amino acid R36 is substituted or deleted and the amino acids R71 and S72 are deleted.
(2b) G1, P2, E3 are deleted, amino acid R36 is substituted by glutamine (Q) and the amino acids R71 and S72 are deleted.
(3b) G1, P2, E3 are deleted, amino acid R37 is substituted or deleted and the amino acids R71 and S72 are deleted.
(4b) G1, P2, E3 are deleted, amino acid R37 is substituted by glutamic acid (E) and the amino acids R71 and S72 are deleted.
(5b) G1, P2, E3 are deleted, amino acid R37 is substituted by alanine and the amino acids R71 and S72 are deleted.
(6b) G1, P2, E3 are deleted, amino acid R37 is substituted by Proline (P) and the amino acids R71 and S72 are deleted.
(7b) G1, P2, E3 are deleted, amino acids R36 and R37 are substituted or deleted and the amino acids R71 and S72 are deleted.
(8b) G1, P2, E3 are deleted, amino acid R36 and R37 are both substituted by glutamine (Q) and the amino acids R71 and S72 are deleted.
(9b) G1, P2, E3 are deleted, amino acid R36 is substituted by glutamine (Q), R37 is substituted by alanine and the amino acids R71 and S72 are deleted.
(10b) G1, P2, E3 are deleted, amino acid R36 is substituted or deleted and the amino acids R71 and S72 are deleted and amino acid R74 is mutated to glutamine (Q).
(11b) G1, P2, E3 are deleted, amino acid R36 is substituted or deleted and the amino acids R71 and S72 are deleted and amino acids R74 and R77 are mutated to glutamine (Q).
(12b) G1, P2, E3 are deleted, amino acid R36 is substituted or deleted and the amino acids R71 and S72 are deleted and amino acids R74, R77 and Q104 are mutated to glutamine (Q).
(13b) G1, P2, E3 are deleted, amino acid R36 is substituted by glutamine (Q) and the amino acids R71 and S72 are deleted and amino acid R74 is mutated to glutamine (Q).
(14b) G1, P2, E3 are deleted, amino acid R36 is substituted by glutamine (Q) and the amino acids R71 and S72 are deleted and amino acids R74 and R77 are mutated to glutamine (Q).
(15b) G1, P2, E3 are deleted, amino acid R36 is substituted by glutamine (Q) and the amino acids R71 and S72 are deleted and amino acids R74, R77 and R104 are mutated to glutamine (Q).
(16b) G1, P2, E3 are deleted, amino acid R37 is substituted by glutamic acid (E) and the amino acids R71 and S72 are deleted and amino acid R77 is mutated to glutamine (Q).
(17b) G1, P2, E3 are deleted, amino acid R37 is substituted by glutamic acid (E) and the amino acids R71 and S72 are deleted and amino acids R74 and R77 are mutated to glutamine (Q).
(18b) G1, P2, E3 are deleted, amino acid R37 is substituted by glutamic acid (E) and the amino acids R71 and S72 are deleted and amino acids R74, R77 and R104 are mutated to glutamine (Q).
(19b) G1, P2, E3 are deleted, amino acid R37 is substituted by alanine (A) and the amino acids R71 and S72 are deleted and amino acid R74 is mutated to glutamine (Q).
(20b) G1, P2, E3 are deleted, amino acid R37 is substituted by alanine (A) and the amino acids R71 and S72 are deleted and amino acids R74 and R77 are mutated to glutamine (Q).
(21b) G1, P2, E3 are deleted, amino acid R37 is substituted by alanine (A) and the amino acids R71 and S72 are deleted and amino acids R74, R77 and R104 are mutated to glutamine (Q).
(22b) G1, P2, E3 are deleted, amino acid R37 is substituted by Proline (P) and the amino acids R71 and S72 are deleted and amino acid R74 is mutated to glutamine (Q).
(23b) G1, P2, E3 are deleted, amino acid R37 is substituted by Proline (P) and the amino acids R71 and S72 are deleted and amino acids R74 and R77 are mutated to glutamine (Q).
(24b) G1, P2, E3 are deleted, amino acid R37 is substituted by Proline (P) and the amino acids R71 and S72 are deleted and amino acids R74, R77 and R104 are mutated to glutamine (Q).
(25b) G1, P2, E3 are deleted, amino acid R36 and R37 are both substituted by glutamine (Q) and the amino acids R71 and S72 are deleted and amino acid R74 is mutated to glutamine (Q).

(26b) G1, P2, E3 are deleted, amino acid R36 and R37 are both substituted by glutamine (Q) and the amino acids R71 and S72 are deleted and amino acids R74 and R77 are mutated to glutamine (Q).

(27b) G1, P2, E3 are deleted, amino acid R36 is substituted by glutamine (Q), R37 is substituted by alanine and the amino acids R71 and S72 are deleted and amino acids R74 and R77 are mutated to glutamine (Q).

(28b) G1, P2, E3 are deleted, amino acid R36 and R37 are both substituted by glutamine (Q) and the amino acids R71 and S72 are deleted and amino acids R74, R77 and R104 are mutated to glutamine (Q).

(29b) G1, P2, E3 are deleted, amino acid R36 is substituted by glutamine (Q), R37 is substituted by alanine and the amino acids R71 and S72 are deleted and amino acids R74, R77 and R104 are mutated to glutamine (Q).

(1c) G1, P2, E3 are deleted, amino acid R36 is substituted or deleted and the amino acids K68, S69, A70, R71 and S72 are deleted.

(2c) G1, P2, E3 are deleted, amino acid R36 is substituted by glutamine (Q) and the amino acids K68, S69, A70, R71 and S72 are deleted.

(3c) G1, P2, E3 are deleted, amino acid R37 is substituted or deleted and the amino acids K68, S69, A70, R71 and S72 are deleted.

(4c) G1, P2, E3 are deleted, amino acid R37 is substituted by glutamic acid (E) and the amino acids K68, S69, A70, R71 and S72 are deleted.

(5c) G1, P2, E3 are deleted, amino acid R37 is substituted by alanine and the amino acids K68, S69, A70, R71 and S72 are deleted.

(6c) G1, P2, E3 are deleted, amino acid R37 is substituted by Proline (P) and the amino acids K68, S69, A70, R71 and S72 are deleted.

(7c) G1, P2, E3 are deleted, amino acids R36 and R37 are substituted or deleted and the amino acids K68, S69, A70, R71 and S72 are deleted.

(8c) G1, P2, E3 are deleted, amino acid R36 and R37 are both substituted by glutamine (Q) and the amino acids K68, S69, A70, R71 and S72 are deleted.

(9c) G1, P2, E3 are deleted, amino acid R36 is substituted by glutamine (Q), R37 is substituted by alanine and the amino acids K68, S69, A70, R71 and S72 are deleted.

(10c) G1, P2, E3 are deleted, amino acid R36 is substituted or deleted and the amino acids K68, S69, A70, R71 and S72 are deleted and amino acid R74 is mutated to glutamine (Q).

(11c) G1, P2, E3 are deleted, amino acid R36 is substituted or deleted and the amino acids K68, S69, A70, R71 and S72 are deleted and amino acids R74 and R77 are mutated to glutamine (Q).

(12c) G1, P2, E3 are deleted, amino acid R36 is substituted or deleted and the amino acids K68, S69, A70, R71 and S72 are deleted and amino acids R74, R77 and Q104 are mutated to glutamine (Q).

(13c) G1, P2, E3 are deleted, amino acid R36 is substituted by glutamine (Q) and the amino acids K68, S69, A70, R71 and S72 are deleted and amino acid R74 is mutated to glutamine (Q).

(14c) G1, P2, E3 are deleted, amino acid R36 is substituted by glutamine (Q) and the amino acids K68, S69, A70, R71 and S72 are deleted and amino acids R74 and R77 are mutated to glutamine (Q).

(15c) G1, P2, E3 are deleted, amino acid R36 is substituted by glutamine (Q) and the amino acids K68, S69, A70, R71 and S72 are deleted and amino acids R74, R77 and R104 are mutated to glutamine (Q).

(16c) G1, P2, E3 are deleted, amino acid R37 is substituted by glutamic acid (E) and the amino acids K68, S69, A70, R71 and S72 are deleted and amino acid R74 is mutated to glutamine (Q).

(17c) G1, P2, E3 are deleted, amino acid R37 is substituted by glutamic acid (E) and the amino acids K68, S69, A70, R71 and S72 are deleted and amino acids R74 and R77 are mutated to glutamine (Q).

(18c) G1, P2, E3 are deleted, amino acid R37 is substituted by glutamic acid (E) and the amino acids K68, S69, A70, R71 and S72 are deleted and amino acids R74, R77 and R104 are mutated to glutamine (Q). (19c) G1, P2, E3 are deleted, amino acid R37 is substituted by alanine (A) and the amino acids K68, S69, A70, R71 and S72 are deleted and amino acid R74 is mutated to glutamine (Q).

(20c) G1, P2, E3 are deleted, amino acid R37 is substituted by alanine (A) and the amino acids K68, S69, A70, R71 and S72 are deleted and amino acids R74 and R77 are mutated to glutamine (Q).

(21c) G1, P2, E3 are deleted, amino acid R37 is substituted by alanine (A) and the amino acids K68, S69, A70, R71 and S72 are deleted and amino acids R74, R77 and R104 are mutated to glutamine (22c) G1, P2, E3 are deleted, amino acid R37 is substituted by Proline (P) and the amino acids K68, S69, A70, R71 and S72 are deleted and amino acid R74 is mutated to glutamine (Q).

(23c) G1, P2, E3 are deleted, amino acid R37 is substituted by Proline (P) and the amino acids K68, S69, A70, R71 and S72 72 are deleted and amino acids R74 and R77 are mutated to glutamine (Q).

(24c) G1, P2, E3 are deleted, amino acid R37 is substituted by Proline (P) and the amino acids K68, S69, A70, R71 and S72 are deleted and amino acids R74, R77 and R104 are mutated to glutamine (Q).

(25c) G1, P2, E3 are deleted, amino acid R36 and R37 are both substituted by glutamine (Q) and the amino acids K68, S69, A70, R71 and S72 are deleted and amino acid R74 is mutated to glutamine (Q).

(26c) G1, P2, E3 are deleted, amino acid R36 and R37 are both substituted by glutamine (Q) and the amino acids K68, S69, A70, R71 and S72 are deleted and amino acids R74 and R77 are mutated to glutamine (Q).

27c) G1, P2, E3 are deleted, amino acid R36 is substituted by glutamine (Q), R37 is substituted by alanine and the amino acids K68, S69, A70, R71 and S72 are deleted and amino acids R74 and R77 are mutated to glutamine (Q).

(28c) G1, P2, E3 are deleted, amino acid R36 and R37 are both substituted by glutamine (Q) and the amino acids K68, S69, A70, R71 and S72 are deleted and amino acids R74, R77 and R104 are mutated to glutamine (Q).

(29c) G1, P2, E3 are deleted, amino acid R36 is substituted by glutamine (Q), R37 is substituted by alanine and the amino acids K68, S69, A70, R71 and S72 are deleted and amino acids R74, R77 and R104 are mutated to glutamine (Q).

In another embodiment the IGF-1 variant which could be produced according to the disclosed method are proteins comprising the above described polypeptides (1b)-(29c), wherein said molecules instead of being mutated at the positions 1-3, only the amino acid E3 is deleted (e.g. the molecule (28c) could also refer to a polypeptide comprising a human IGF-1 precursor protein fused to an immunoglobulin Fc region wherein the amino acid G42 is substituted by the amino acid amino acid serine and wherein the amino acid(s) E3 are deleted, amino acid R36 and R37 are both substituted by glutamine (Q) and the amino acids K68, S69, A70, R71 and S72 are deleted and amino acids R74, R77 and R104 are mutated to glutamine (Q).)

In another embodiment the IGF-1 variant which can be produced according to the disclosed method relates to the above described polypeptides 1-29c, comprising an mutated Ea-peptide consisting of the amino acids a) VQAQQHTDMPKTQKEVHLKNASG (SEQ ID. NO.: 33), or
b) VQAQQHTDMPKTQKYQPPATNKNTKSQRRKGS (SEQ ID. NO.: 34).

In a further embodiment, an IGF-1 variant which could be produced according to the disclosed method is an IGF-1 precursor protein as described above being fused to a Fc region, wherein the Fc region may be directly fused to the modified IGF-1 precursor polypeptide or may be connected by a hinge region using recombinant DNA technologies well known in the art. If a DNA hinge region is used, the Fc region may be connected to any part of the modified IGF-1 precursor polypeptide. In one embodiment the Fc region is fused directly to the C-terminus of the modified IGF-1 precursor polypeptide. In another embodiment, the Fc region is linked to the C-terminus of the modified IGF-1 precursor polypeptide by a Gly-Ser (-GS-) linker.

A DNA linker may be used to provide a restriction site between components for ease of manipulation. A linker may also be provided to enhance expression of the polypeptide from a host cell, to decrease steric hindrance such that the component may assume its optimal tertiary or quaternary structure and/or interact appropriately with its target molecule. For linkers and methods of identifying desirable spacers, see, for example, George et al. (2003) Protein Engineering 15:871-879.

A linker sequence may include one or more amino acids naturally connected to a receptor component, or may be an added sequence used to enhance expression of the fusion protein, provide specifically desired sites of interest and allow component domains to form optimal tertiary structures and/or to enhance the interaction of a component with its target molecule. In one embodiment, the linker comprises one or more peptide sequences which are between 1-100 amino acids, preferably 1-25 amino acids in length. In one embodiment, the linker is 1-5 amino acids in length. In one embodiment, the linker is a three amino acid sequence; more specifically, the three amino acid sequence of Gly Pro Gly. In another embodiment, the linker is Gly-Ser.

Examples of such hinge molecules include, but are not limited to, the following polypeptides:

hinge 1:
(SEQ ID NO.: 30)
CPPCPA hinge 2:
(SEQ ID NO.: 31)
DKTHTCPPCPA hinge 3:
(SEQ ID NO.: 32)
EPKSCDKTHTCPPCPA Consequently, the disclosure relates to a method in which an IGF-1 variant is produced containing a human IGF-1 Ea-peptide precursor protein which is fused to an immunoglobulin Fc region, particularly a modified Fc region, particularly an Fc region, which is modified to modulate its binding to Fc receptor, preferably by substituting one or both of amino acids 234 and 235 to alanine as described above, wherein the amino acid glycine at position 42 is deleted or substituted by serine, wherein the numbering of the amino acids corresponds to SEQ ID NO.: 20 and wherein the immunoglobulin Fc region is fused to the IGF-1 precursor protein via a hinge region.

Examples of such molecules include, but are not limited to, the following polypeptides:

hIgF1-Ea-Fc_mut 13/2_E (SEQ ID NO.: 23)
hIgF1-Ea-Fc_mut 13/2_A (SEQ ID NO.: 24)
hIgF1-Ea-Fc_mut 13/2_C (SEQ ID NO.: 25)
hIgF1-Ea-Fc_mut 13/2_F (SEQ ID NO.: 26)
hIgF1-Ea-Fc_mut 04/2_A (SEQ ID NO.: 28)
hIgF1-Ea-Fc_mut 04/2_E (SEQ ID NO.: 27)
hIgF1-Ea-Fc_mut 04/2_F (SEQ ID NO.: 29)

In certain aspects the disclosure relates to the above described methods, wherein the mammalian cell is selected from the group consisting of cell from *Cricetulus griseus*, *Cercopithecus aethiops*, *Homo sapiens*, *Mesocricetus auratus*, *Mus musculus* and *Chlorocebus* species. In other embodiments, which can be combined with any of the proceeding embodiments, the mammalian cell is selected from the group consisting of CHO-cells (Chinese Hamster Ovary), COS-cells (a cell line derived from monkey kidney (African green monkey), Vero-cells (kidney epithelial cells extracted from African green monkey), Hela-cells (The line was derived from cervical cancer cells taken from Henrietta Lacks), BHK-cells (baby hamster kidney cells, HEK-cells (Human Embryonic Kidney), NS0-cells (Murine myeloma cell line), C127-cells (nontumorigenic mouse cell line), PerC6®-cells (human cell line, Crucell), CAP-cells (CEVEC's Amniocyte Production) and Sp-2/0-cells (Mouse myeloma cells).

CHO cells were successfully isolated for the first time in 1957 (Tjio J H, Puck TT (1958) Genetics of somatic mammalian cells. II. Chromosomal constitution of cells in tissue culture. J Exp Med 108(2):259-268). Based on the original immortalized CHO cell line, several different clones have been developed. The CHO-K1 strain, derived from the original cell line, depends on glycine supplementation (Kao F T, Puck T T (1968) Genetics of somatic mammalian cells, VII. Induction and isolation of nutritional mutants in Chinese hamster cells. Proc Natl Acad Sci USA 60(4):1275-1281). Subsequent genetic mutations led to the CHO-DG44 strain in which both alleles of dihydrofolate reductase (DHFR) were deleted (Urlaub G, Chasin L A (1980) Isolation of Chinese hamster cell mutants deficient in dihydrofolate reductase activity. Proc Natl Acad Sci USA 77(7): 4216-4220). This cell line requires glycine and hypoxanthine as well as thymidine for growth. Although the DG44 cell line was intended for research, this strain became one of the most commonly used CHO expression systems. In a particular aspect, the mammalian cell used in the above disclosed method is a Chinese Hamster Ovary (CHO) cell, wherein said CHO cell can be a CHO-K1 derivative cell, a CHO-DUXB11 derivative cell or a CHO-DG44 cell. CHO K1 cells are sub-clones of the parental CHO cell line that was initiated from an ovary biopsy of an adult Chinese hamster in 1957 (DSMZ no.: ACC110). They require proline, because of the absence of the appropriate synthesis apparatus. Different host cells which have specific cellular machineries and characteristic mechanisms for post-translational activities (e.g., CHO, HeLa, MDCK, HEK293, and WI38), are available from the American Type Culture Collection.

In a particular embodiment of the invention the CHO cells are CHO-K1 derivative cells, the IGFR1 of said cells has been knocked out by using zinc finger nucleases or knocked down by using the RNA interference technology and the therapeutic protein produced in said cells according to the method of the invention is the IGF-1 protein of SEQ ID NO.: 23, or SEQ ID NO.: 24, or SEQ ID NO.: 25, or SEQ ID NO.: 26, or SEQ ID NO.: 27, or SEQ ID NO.: 28, or SEQ ID NO.: 29.

In an additional aspect the disclosure relates to a genetically modified mammalian cell that has been modified to allow a higher expression of a heterologous recombinant therapeutic protein in said cell compared to a cell of the same type which has not been so modified, wherein the heterologous recombinant therapeutic protein is a ligand of an endogenous cognate receptor expressed in said cell, and wherein the genetic modification resulted in a deficient expression of said cognate receptor, and wherein the expression of the recombinant therapeutic protein is at least 1.5-fold, or 2-fold, or 3-fold, or 4-fold, or 5 fold, or 6-fold, or 7-fold, or 8-fold, or 9-fold, or 10-fold or more higher than in a cell in which the expression of the cognate receptor of the therapeutic protein has not been so modified.

In another particular embodiment, the disclosure relates to a genetically modified mammalian cell that has been modified to allow a higher expression of a heterologous recombinant therapeutic protein in said cell compared to a cell of the same type which has not been so modified, wherein the heterologous recombinant therapeutic protein is a ligand of an endogenous cognate receptor expressed in said cell, and wherein the genetic modification resulted in a deficient expression of said cognate receptor and said genetically modified mammalian cells when expressing the therapeutic protein are able to grow up to $0.5\text{-}1\times10^7$ cells/ml or $1\text{-}1.5\times10^7$ cells/ml or $1.5\text{-}2\times10^7$ cells/ml or $2\text{-}2.5\times10^7$ or $3\text{-}3.5\times10^7$ cells/ml or higher during the cultivation time.

In an additional embodiment, the disclosure relates to a genetically modified mammalian cell that has been modified to allow a higher expression of a heterologous recombinant therapeutic protein in said cell compared to a cell of the same type which has not been so modified, wherein the heterologous recombinant therapeutic protein is a ligand of an endogenous cognate receptor expressed in said cell, and wherein the genetic modification resulted in a deficient expression of said cognate receptor and wherein the viability of said genetically modified mammalian cell, when expressing the therapeutic protein, is over 97% during the first 80-110 h or 110-140 h or 140-170 h or 170-200 h or 200-230 h or 230-260 h cultivation time.

In another aspect the disclosure relates to a genetically modified mammalian cell that has been modified to allow a higher expression of a heterologous recombinant therapeutic protein in said cell compared to a cell of the same type which has not been so modified, wherein the heterologous recombinant therapeutic protein is a ligand of an endogenous cognate receptor expressed in said cell, and wherein the genetic modification resulted in a deficient expression of said cognate receptor and (i) wherein the expression of the recombinant therapeutic protein is at least 1.5-fold, or 2-fold, or 3-fold, or 4-fold, or 5 fold, or 6-fold, or 7-fold, or 8-fold, or 9-fold, or 10-fold or more higher than in a cell which had not been so modified (ii) and said genetically modified mammalian cells are able to grow up to $0.5\text{-}1\times10^7$ cells/ml or $1\text{-}1.5\times10^7$ cells/ml or $1.5\text{-}2\times10^7$ cells/ml or $2\text{-}2.5\times10^7$ or $3\text{-}3.5\times10^7$ cells/ml or higher during the cultivation time (iii) and the viability of said genetically modified mammalian cell is over 90% during the first 80-110 h or 110-140 h or 140-170 h or 170-200 h or 200-230 h or 230-260 h cultivation time.

In yet another aspects the disclosure relates to the above described genetically modified mammalian cell that has been modified to allow a higher expression of a heterologous recombinant therapeutic protein in said cell compared to a cell of the same type which has not been so modified, wherein the mammalian cell is selected from the group consisting of Cricetulus griseus, Cercopithecus aethiops, Homo sapiens, Mesocricetus auratus, Mus musculus and Chlorocebus sp. Cell.

In other embodiments, which can be combined with any of the preceding embodiments, the above described mammalian cell is selected from the group consisting of CHO-cells (Chinese Hamster Ovary), COS-cells (a cell line derived from monkey kidney (African green monkey), Vero-cells (kidney epithelial cells extracted from African green monkey), Hela-cells (The line was derived from cervical cancer cells taken from Henrietta Lacks), BHK-cells (baby hamster kidney cells, HEK-cells (Human Embryonic Kidney), NS0-cells (Murine myeloma cell line), C127-cells (nontumorigenic mouse cell line), PerC6®-cells (human cell line, Crucell), CAP-cells (CEVEC's Amniocyte Production) and Sp-2/0-cells (Mouse myeloma cells). In a particular aspect, the mammalian cell described above is a Chinese Hamster Ovary (CHO) cell, wherein said CHO cell can be a CHO-K1 derivative cell, a CHO-DUXB11 derivative cell or a CHO-DG44 cell.

Yet another aspect of the disclosure includes a genetically modified CHO cell, e.g. a CHO-K1 derivative or CHO-DUXB11 derivative cell, being deficient in the expression of the Insulin like growth factor 1 receptor.

In an additional embodiment, the above described CHO cell being deficient in the expression of the Insulin like growth factor 1 receptor harbors chromosomal or extra-chromosomal at least one copy of the human Insulin like growth factor 1 gene or a variant thereof under control of a heterologous promoter.

In yet another embodiment, which can be combined with any of the preceding embodiments, the above described CHO cell being deficient in the expression of the Insulin like growth factor 1 receptor comprises at least one chromosomal or extra-chromosomal copy of the human Insulin like growth factor 1 gene or a variant thereof under control of a heterologous promoter, allowing the expression of at least 1.5-times, or 2-times, or 3-times, or 4-times, or 5 times, or 6-times, or 7-times, or 8-times, or 9-times, or 10-times more human Insulin like growth factor 1 protein or a variant thereof compared to a cell of the same type in which the expression of the IGF-1R had not been so modified.

In other embodiments, which can be combined with any of the preceding embodiments, the above described CHO cell being deficient in the expression of the Insulin like growth factor 1 receptor comprises at least one chromosomal or extra-chromosomal copy of the human Insulin like growth factor 1 gene or a variant thereof under control of a heterologous promoter and only non-functional Insulin like growth factor 1 receptor genes which have been knocked out by targeted genetic recombination technologies.

In an additional embodiment, which can be combined with any of the preceding embodiments, the above described CHO cell being deficient in the expression of the Insulin like growth factor 1 receptor comprises at least (i) one chromosomal or extra-chromosomal copy of the human Insulin like growth factor 1 gene or a variant thereof under control of a heterologous promoter and (ii) double stranded siRNA molecules comprising at least two sequences that are complementary to each other and wherein a sense strand comprises a first sequence and an antisense strand comprises a second sequence comprising a region of complementarity which is substantially complementary to at least a part of the mRNA encoding IGF-1R and wherein the total length of each separate strand of siRNA may be 15 to 49 nucleotides, 17 to 30 nucleotides or 19 to 25 nucleotides and wherein the expression of the Insulin like growth factor 1 receptor being inhibited by at least 10%, 30%, 50%, 90%, 95% or 99% when compared to a cell not treated with the above mentioned dsRNA molecules according to the present disclosure. In one embodiment, the above described cell comprises at least one double stranded siRNA molecule wherein the sequence of the sense strand of said molecule is selected from the group consisting of SEQ ID NOs: 1 or 3.

In a further embodiment, which can be combined with any of the preceding embodiments, the above described CHO cell being deficient in the expression of the Insulin like growth factor 1 receptor comprises at least (i) one chromosomal or extra-chromosomal copy of the human Insulin like growth factor 1 gene or a variant thereof under control of a heterologous promoter and (ii) shRNA molecules comprising a region of complementarity to at least a part of the mRNA encoding IGF-1R and and wherein the expression of the Insulin like growth factor 1 receptor being inhibited by at least 10%, 30%, 50%, 90%, 95% or 99% when compared to a cell not treated with the above mentioned shRNA molecules according to the present invention. In one embodiment, the above described cell comprises at least one type of shRNA molecule selected from the group consisting of SEQ ID NO.: 5, 6, 7, 8, 9 and 10.

SEQUENCES

| SEQ ID | DNA/PROT | Description | Sequence |
|---|---|---|---|
| 1 | DNA | IGF1R siRNA (1) sense | CAGUCAAAAUUGGAGAUUUTT |
| 2 | DNA | IGF1R siRNA (1) anti-sense | AAAUCUCCAAUUUUGACUGTG |
| 3 | DNA | IGF1R siRNA (2) sense | CCACAUGGGUUAAGUUAAATT |
| 4 | DNA | IGF1R siRNA (2) anti-sense | UUUAACUUAACCCAUGUGGTA |
| 5 | DNA | IGF1R shRNA 1 | AGCTTTTCCAAAAAATACCACATGGGTTAAGTTAAATCTCTTGAATTTAACTTAACCCATGTGGCG |
| 6 | DNA | IGF1R shRNA 2 | AGCTTTTCCAAAAAACAGCATCAAGGATGAGATGGATCTCTTGAGTCCATCTCATCCTTGATGCG |
| 7 | DNA | IGF1R shRNA 3 | AGCTTTTCCAAAAAACTGCATGGTAGCTGAAGATTTTCTCTTGAGAAATCTTCAGCTACCATGCG |
| 8 | DNA | IGF1R shRNA 4 | AGCTTTTCCAAAAAACTGGTTTACAAGAACTAATTATCTCTTGAGTAATTAGTTCTTGTAAACCG |
| 9 | DNA | IGF1R shRNA 5 | AGCTTTTCCAAAAAATACCCTTTCTTTGAGAGCAGATCTCTTGAGTCTGCTCTCAAAGAAAGGGCG |
| 10 | DNA | IGF1R shRNA 6 | AGCTTTTCCAAAAAACGGCACAACTACTGCTCCAAATCTCTTGAATTTGGAGCAGTAGTTGTGCG |
| 11 | DNA | CHO IGF1R zink finger nuclease recognition sites and cutting site | CCCACCTGGCACCTACAGGT/TCGAGGGCTGGCGCTGTGTGG |
| 12 | DNA | CHO IGF1R forward sequencing primer (in intron 2-3) | CTAGCCTGTCTCTGGGACAC |
| 13 | DNA | CHO IGF1R reverse sequencing primer (in intron 3-4) | CTGGATGAACCTCTGGGTGG |
| 14 | DNA | CHO IGF1R exon 3 | TGTGCCCAAGTGTGTGCGGAAAGCGAGCGTGCACCGAGAACAACGAATGCTGCCACCCAGAGTGCCTAGGCAGCTGCCATACACCTGACGACAACACAACCTGTGTGGCCTGCCGACACTACTACTACAAAGGCGTGTGTGTGCCTGCCTGCCCACCTGGCACCTACAGGT/TCGAGGGCTGGCGCTGTGTGGACCGCGATTTCTGCGCCAACATCCCCAACGCTGAGAGCAGTGACTCAGATGGCTTTGTCATCCACGATGCGAGTGCATGCAAGAATGTCCCTCAGGCTTCATCCGCAACAGCACCCAGAG |

| SEQ ID | DNA/PROT | Description | Sequence |
|---|---|---|---|
| 15 | DNA | CHO IGF1R exon 3 and flanking introns | AAACTTAACGGCACATCCCATAGCAAACCATTTCATAAGAAAGGACTTGGC ATGTGTTGTGTCCTTTCCCAGTGTGGGCTTCACAGATGGTATTACCTGTGCA GATTTCAGAGAAAGTGTGTTTTCCTAGCCTGTCTCTGGGACACCATTTAGT GCTGGTTGTGGCAGCAGATGACCCTGGGGAGGCTGTGTAGTCTCTTCATCT CACCACCTCCTCCCCCTGTTCCCACAGTGTGCCCAAGTGTGTGCGGAAAGC GAGCGTGCACCGAGAACAACGAATGCTGCCACCCAGAGTGCCTAGGCAGCT GCCATACACCTGACGACAACACAACCTGTGTGGCCTGCCGACACTACTACTA CAAAGGCGTGTGTGTGCCTGCCTGCCCACCTGGCACCTACAGGT/TCGAGGG CTGGCGCTGTGTGGACCGCGATTTCTGCGCCAACATCCCCAACGCTGAGAG CAGTGACTCAGATGGCTTTGTCATCCACGATGGCGAGTGCATGCAAGAATGT CCCTCAGGCTTCATCCGCAACAGCACCCAGAGGTCAGTGGCTCTTGTTCCCC ATCCAGGAGGTGAATCTTGTTCATATTCCATGATTGTAGGAACCACCCAGAG GTTCATCCAGATGGGGAGGCTGTTGGAGGGTGCTGACTAAGCTTGTTTTTAT GAGAATCTTGGAATGGCTGGTCTGTTCATTTCTTTGTTTGTTGGCTTGCTTTG TTGTCTTTGAAAGTGCCTTGCTAGCCCTAGAGAGGAAGAATTAGCCTGCTG |
| 16 | PROT. | human insulin growth factor 1 (hIGF-1) | GPETLCGAELVDALQFVCGDRGFYFNKPTGYGSSSRRAPQTGIVDECCFRSCDL RRLEMYCAPLKPAKSA |
| 17 | PROT. | Ea peptide | RSVRAQRHTDMPKTQKEVHLKNASRGSAGNKNYRM |
| 18 | PROT. | Eb peptide | RSVRAQRHTDMPKTQKYQPPSTNKNTKSQRRKGWPKTHPGGEQKEGTEASLQI RGKKKEQRREIGSRNAECRGKKGK |
| 19 | PROT. | Ec peptide | RSVRAQRHTDMPKTQKYQPPSTNKNTKSQRRKGSTFEERK |
| 20 | PROT. | Wild type IGF-1-Ea without the leader-sequence | GPETLCGAELVDALQFVCGDRGFYFNKPTGYGSSSRRAPQTGIVDECCFRSCDL RRLEMYCAPLKPAKSARSVRAQRHTDMPKTQKEVHLKNASRGSAGNKNYRM |
| 21 | PROT. | hIGF1-Ea-D1-3, R37A, D71-72, 77-fc domain | TLCGAELVDALQFVCGDRGFYFNKPTGYGSSSRAAPQTGIVDECCFRSCDLRRL EMYCAPLKPAKSAVRAQHTDMPKTQKEVHLKNASRGSAGNKNYRMGSDKTHTC PPCPAPEAAGGPSVFLFPPKPKDTLMISRTPEVTCVVVDVSHEDPEVKFNWYVD GVEVHNAKTKPREEQYNSTYRVVSVLTVLHQDWLNGKEYKCKVSNKALPAPIEK TISKAKGQPREPQVYTLPPSREEMTKNQVSLTCLVKGFYPSDIAVEWESNGQPE NNYKTTPPVLDSDGSFFLYSKLTVDKSRWQQGNVFSCSVMHEALHNHYTQKSL SLSPGK |
| 22 | PROT. | hIGF1-Ea-D1-3, R37A, D71-72, R77Q-fc domain | TLCGAELVDALQFVCGDRGFYFNKPTGYGSSSRAAPQTGIVDECCFRSCDLRRL EMYCAPLKPAKSAVRAQQHTDMPKTQKEVHLKNASRGSAGNKNYRMGSDKTH TCPPCPAPEAAGGPSVFLFPPKPKDTLMISRTPEVTCVVVDVSHEDPEVKFNWY VDGVEVHNAKTKPREEQYNSTYRVVSVLTVLHQDWLNGKEYKCKVSNKALPAPI EKTISKAKGQPREPQVYTLPPSREEMTKNQVSLTCLVKGFYPSDIAVEWESNGQ PENNYKTTPPVLDSDGSFFLYSKLTVDKSRWQQGNVFSCSVMHEALHNHYTQK SLSLSPGK |
| 23 | PROT. | hIgF1-Ea-Fc mut 13/2_E | TLCGAELVDALQFVCGDRGFYFNKPTGYGSSSQAAPQTSIVDECCFRSCDLRRL EMYCAPLKPAVQAQQHTDMPKTQKEVHLKNASRGSAGNKNYQMDKTHTCPPC PAPEAAGGPSVFLFPPKPKDTLMISRTPEVTCVVVDVSHEDPEVKFNWYVDGVE VHNAKTKPREEQYNSTYRVVSVLTVLHQDWLNGKEYKCKVSNKALPAPIEKTISK AKGQPREPQVYTLPPSREEMTKNQVSLTCLVKGFYPSDIAVEWESNGQPENNY KTTPPVLDSDGSFFLYSKLTVDKSRWQQGNVFSCSVMHEALHNHYTQKSLSLSP GK |
| 24 | PROT. | hIgF1-Ea-Fc mut 13/2_A | TLCGAELVDALQFVCGDRGFYFNKPTGYGSSSQAAPQTSIVDECCFRSCDLRRL EMYCAPLKPAVQAQQHTDMPKTQKEVHLKNASRGSAGNKNYQMCPPCPAPEA AGGPSVFLFPPKPKDTLMISRTPEVTCVVVDVSHEDPEVKFNWYVYVDGVEVHNAK TKPREEQYNSTYRVVSVLTVLHQDWLNGKEYKCKVSNKALPAPIEKTISKAKGQP REPQVYTLPPSREEMTKNQVSLTCLVKGFYPSDIAVEWESNGQPENNYKTTPPV LDSDGSFFLYSKLTVDKSRWQQGNVFSCSVMHEALHNHYTQKSLSLSPGK |
| 25 | PROT. | hIgF1-Ea-Fc mut 13/2_C | TLCGAELVDALQFVCGDRGFYFNKPTGYGSSSQAAPQTSIVDECCFRSCDLRRL EMYCAPLKPAVQAQQHTDMPKTQKEVHLKNASGCPPCPAPEAAGGPSVFLFPP KPKDTLMISRTPEVTCVVVDVSHEDPEVKFNWYVDGVEVHNAKTKPREEQYNST YRVVSVLTVLHQDWLNGKEYKCKVSNKALPAPIEKTISKAKGQPREPQVYTLPPS REEMTKNQVSLTCLVKGFYPSDIAVEWESNGQPENNYKTTPPVLDSDGSFFLYS KLTVDKSRWQQGNVFSCSVMHEALHNHYTQKSLSLSPGK |
| 26 | PROT. | hIgF1-Ea-Fc mut 13/2_F | TLCGAELVDALQFVCGDRGFYFNKPTGYGSSSQAAPQTSIVDECCFRSCDLRRL EMYCAPLKPAVQAQQHTDMPKTQKEVHLKNASGDKTHTCPPCPAPEAAGGPSV FLFPPKPKDTLMISRTPEVTCVVVDVSHEDPEVKFNWYVDGVEVHNAKTKPREE |

| SEQ ID | DNA/PROT | Description | Sequence |
|---|---|---|---|
| | | | QYNSTYRVVSVLTVLHQDWLNGKEYKCKVSNKALPAPIEKTISKAKGQPREPQVY<br>TLPPSREEMTKNQVSLTCLVKGFYPSDIAVEWESNGQPENNYKTTPPVLDSDGS<br>FFLYSKLTVDKSRWQQGNVFSCSVMHEALHNHYTQKSLSLSPGK |
| 27 | PROT. | hIgF1-Ea-<br>Fc mut<br>04/2_E | TLCGAELVDALQFVCGDRGFYFNKPTGYGSSSREAPQTSIVDECCFRSCDLRRL<br>EMYCAPLKPAVQAQQHTDMPKTQKEVHLKNASRGSAGNKNYQMDKTHTCPPC<br>PAPEAAGGPSVFLFPPKPKDTLMISRTPEVTCVVVDVSHEDPEVKFNWYVDGVE<br>VHNAKTKPREEQYNSTYRVVSVLTVLHQDWLNGKEYKCKVSNKALPAPIEKTISK<br>AKGQPREPQVYTLPPSREEMTKNQVSLTCLVKGFYPSDIAVEWESNGQPENNY<br>KTTPPVLDSDGSFFLYSKLTVDKSRWQQGNVFSCSVMHEALHNHYTQKSLSLSP<br>GK |
| 28 | PROT. | hIgF1-Ea-<br>Fc mut<br>04/2_A | TLCGAELVDALQFVCGDRGFYFNKPTGYGSSSREAPQTSIVDECCFRSCDLRRL<br>EMYCAPLKPAVQAQQHTDMPKTQKEVHLKNASRGSAGNKNYQMCPPCPAPEA<br>AGGPSVFLFPPKPKDTLMISRTPEVTCVVVDVSHEDPEVKFNVVYVDGVEVHNAK<br>TKPREEQYNSTYRVVSVLTVLHQDWLNGKEYKCKVSNKALPAPIEKTISKAKGQP<br>REPQVYTLPPSREEMTKNQVSLTCLVKGFYPSDIAVEWESNGQPENNYKTTPPV<br>LDSDGSFFLYSKLTVDKSRWQQGNVFSCSVMHEALHNHYTQKSLSLSPGK |
| 29 | PROT. | hIgF1-Ea-<br>Fc mut<br>04/2_F | TLCGAELVDALQFVCGDRGFYFNKPTGYGSSSREAPQTSIVDECCFRSCDLRRL<br>EMYCAPLKPAVQAQQHTDMPKTQKEVHLKNASGDKTHTCPPCPAPEAAGGPSV<br>FLFPPKPKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQPREPQVY<br>TLPPSREEMTKNQVSLTCLVKGFYPSDIAVEWESNGQPENNYKTTPPVLDSDGS<br>FFLYSKLTVDKSRWQQGNVFSCSVMHEALHNHYTQKSLSLSPGK |
| 30 | PROT. | hinge 1 | CPPCPA |
| 31 | PROT. | hinge 2 | DKTHTCPPCPA |
| 32 | PROT. | hinge 3 | EPKSCDKTHTCPPCPA |
| 33 | PROT. | mutated Ea-<br>peptide 1 | RSVRAQRHTDMPKTQKEVHLKNASG |
| 34 | PROT. | mutated Ea-<br>peptide 2 | RSVRAQRHTDMPKTQKYQPPATNKNTKSQRRKGS |
| 35 | PROT. | hIGF1-Ea-mut<br>3 | GPTLCGAELVDALQFVCGDRGFYFNKPTGYGSSSRAAPQTGIVDECCFRSCDLR<br>RLEMYCAPLKPAKSAVRAQRHTDMPKTQKEVHLKNASRGSAGNKNYRM |
| 36 | DNA | pZFN1 vector | TCGCGATGTACGGGCCAGATATACGCGTTGACATTGATTATTGACTAGTTATT<br>AATAGTAATCAATTACGGGGTCATTAGTTCATAGCCCATATATGGAGTTCCGC<br>GTTACATAACTTACGGTAAATGGCCCGCCTGGCTGACCGCCCAACGACCCCC<br>GCCCATTGACGTCAATAATGACGTATGTTCCCATAGTAACGCCAATAGGGACT<br>TTCCATTGACGTCAATGGGTGGACTATTTACGGTAAACTGCCCACTTGGCAGT<br>ACATCAAGTGTATCATATGCCAAGTACGCCCCCTATTGACGTCAATGACGGTA<br>AATGGCCCGCCTGGCATTATGCCCAGTACATGACCTTATGGGACTTTCCTACT<br>TGGCAGTACATCTACGTATTAGTCATCGCTATTACCATGGTGATGCGGTTTTG<br>GCAGTACATCAATGGGCGTGGATAGCGGTTTGACTCACGGGGATTTCCAAGT<br>CTCCACCCCATTGACGTCAATGGGAGTTTGTTTTGGCACCAAAATCAACGGG<br>ACTTTCCAAAATGTCGTAACAACTCCGCCCCATTGACGCAAATGGGCGGTAG<br>GCGTGTACGGTGGGAGGTCTATATAAGCAGAGCTCTCTGGCTAACTAGAGAA<br>CCCACTGCTTACTGGCTTATCGAAATTAATACGACTCACTATAGGGAGACCCA<br>AGCTGGCTAGCGTTTAAACTTAAGCTGATCCACTAGTCCAGTGTGGTGGAATT<br>CGCCATGGACTACAAAGACCATGACGGTGATTATAAAGATCATGACATCGATT<br>ACAAGGATGACGATGACAAGATGGCCCCCAAGAAGAAGAGGAAGGTGGGCA<br>TCCACGGGGTACCCGCCGCTATGGCTGAGAGGCCCTTCCAGTGTCGAATCT<br>GCATGCGTAACTTCAGTCGCTCCGCCCACCTGTCCCGCCACATCCGCACCCA<br>CACCGGCGAGAAGCCTTTTGCCTGTGACATTTGTGGGAGGAAATTTGCCACC<br>TCCGGCCACCTGTCCCGCCATACCAAGATACACACGGGCAGCCAAAAGCCCT<br>TCCAGTGTCGAATCTGCATGCGTAACTTCAGTCAGTCCGGCGACCTGACCCG<br>CCACATCCGCACCCACACCGGCGAGAAGCCTTTTGCCTGTGACATTTGTGGG<br>AGGAAATTTGCCCGCTCCTGGGGCCTGCAGGTGCATACCAAGATACACACGG<br>GATCTCAGAAGCCCTTCCAGTGTCGAATCTGCATGCGTAACTTCAGTCGCTC<br>CGACAACCTGTCCACCCACATCCGCACCCACACCGGCGAGAAGCCTTTTGCC<br>TGTGACATTTGTGGGAGGAAATTTGCCCGCTCCGACGCCCGCGCCAACCATA<br>CCAAGATACACCTGCGGGGATCCCAGCTGGTGAAGAGCGAGCTGGAGGAGA<br>AGAAGTCCGAGCTGCGGCACAAGCTGAAGTACGTGCCCCACGAGTACATCG<br>AGCTGATCGAGATCGCCAGGAACAGCACCCAGGACCGCATCCTGGAGATGA<br>AGGTGATGGAGTTCTTCATGAAGGTGTACGGCTACAGGGGAAAGCACCTGG<br>GCGGAAGCAGAAAGCCTGACGGCGCCATCTATACAGTGGGCAGCCCCATCG<br>ATTACGGCGTGATCGTGGACACAAAGGCCTACAGCGGCGGCTACAATCTGCC<br>TATCGGCCAGGCCGACGAGATGGAGAGATACGTGGAGGAGAACCAGACCCG |

| SEQ ID | DNA/PROT | Description | Sequence |
|---|---|---|---|
| | | | GAATAAGCACCTCAACCCCAACGAGTGGTGGAAGGTGTACCCTAGCAGCGTG
ACCGAGTTCAAGTTCCTGTTCGTGAGCGGCCACTTCAAGGGCAACTACAAGG
CCCAGCTGACCAGGCTGAACCACATCACCAACTGCAATGGCGCCGTGCTGA
GCGTGGAGGAGCTGCTGATCGGCGGCGAGATGATCAAAGCCGGCACCCTGA
CACTGGAGGAGGTGCGGCGCAAGTTCAACAACGGCGAGATCAACTTCAGAT
CTTGATAACTCGAGTCTAGAGGGCCCGTTTAAACCCGCTGATCAGCCTCGAC
TGTGCCTTCTAGTTGCCAGCCATCTGTTGTTTGCCCCTCCCCCGTGCCTTCCT
TGACCCTGGAAGGTGCCACTCCCACTGTCCTTTCCTAATAAAATGAGGAAATT
GCATCGCATTGTCTGAGTAGGTGTCATTCTATTCTGGGGGGTGGGGTGGGGC
AGGACAGCAAGGGGGAGGATTGGGAAGACAATAGCAGGCATGCTGGGGATG
CGGTGGGCTCTATGGCTTCTACTGGGCGGTTTTATGGACAGCAAGCGAACCG
GAATTGCCAGCTGGGGCGCCCTCTGGTAAGGTTGGGAAGCCCTGCAAAGTA
AACTGGATGGCTTTCTCGCCGCCAAGGATCTGATGGCGCAGGGGATCAAGCT
CTGATCAAGAGACAGGATGAGGATCGTTTCGCATGATTGAACAAGATGGATT
GCACGCAGGTTCTCCGGCCGCTTGGGTGGAGAGGCTATTCGGCTATGACTG
GGCACAACAGACAATCGGCTGCTCTGATGCCGCCGTGTTCCGGCTGTCAGC
GCAGGGGCGCCCGGTTCTTTTTGTCAAGACCGACCTGTCCGGTGCCCTGAAT
GAACTGCAAGACGAGGCAGCGCGGCTATCGTGGCTGGCCACGACGGGCGTT
CCTTGCGCAGCTGTGCTCGACGTTGTCACTGAAGCGGGAAGGGACTGGCTG
CTATTGGGCGAAGTGCCGGGGCAGGATCTCCTGTCATCTCACCTTGCTCCTG
CCGAGAAAGTATCCATCATGGCTGATGCAATGCGGCGGCTGCATACGCTTGA
TCCGGCTACCTGCCCATTCGACCACCAAGCGAAACATCGCATCGAGCGAGCA
CGTACTCGGATGGAAGCCGGTCTTGTCGATCAGGATGATCTGGACGAAGAGC
ATCAGGGGCTCGCGCCAGCCGAACTGTTCGCCAGGCTCAAGGCGAGCATGC
CCGACGGCGAGGATCTCGTCGTGACCCATGGCGATGCCTGCTTGCCGAATA
TCATGGTGGAAAATGGCCGCTTTTCTGGATTCATCGACTGTGGCCGGCTGGG
TGTGGCGGACCGCTATCAGGACATAGCGTTGGCTACCCGTGATATTGCTGAA
GAGCTTGGCGGCGAATGGGCTGACCGCTTCCTCGTGCTTTACGGTATCGCC
GCTCCCGATTCGCAGCGCATCGCCTTCTATCGCCTTCTTGACGAGTTCTTCTG
AATTATTAACGCTTACAATTTCCTGATGCGGTATTTTCTCCTTACGCATCTGTG
CGGTATTTCACACCGCATACAGGTGGCACTTTTCGGGGAAATGTGCGCGGAA
CCCCTATTTGTTTATTTTTCTAAATACATTCAAATATGTATCCGCTCATGAGACA
ATAACCCTGATAAATGCTTCAATAATAGCACGTGCTAAAACTTCATTTTTAATTT
AAAAGGATCTAGGTGAAGATCCTTTTTGATAATCTCATGACCAAAATCCCTTAA
CGTGAGTTTTCGTTCCACTGAGCGTCAGACCCCGTAGAAAAGATCAAAGGAT
CTTCTTGAGATCCTTTTTTTCTGCGCGTAATCTGCTGCTTGCAAACAAAAAAAC
CACCGCTACCAGCGGTGGTTTGTTTGCCGGATCAAGAGCTACCAACTCTTTTT
CCGAAGGTAACTGGCTTCAGCAGAGCGCAGATACCAAATACTGTCCTTCTAG
TGTAGCCGTAGTTAGGCCACCACTTCAAGAACTCTGTAGCACCGCCTACATA
CCTCGCTCTGCTAATCCTGTTACCAGTGGCTGCTGCCAGTGGCGATAAGTCG
TGTCTTACCGGGTTGGACTCAAGACGATAGTTACCGGATAAGGCGCAGCGGT
CGGGCTGAACGGGGGGTTCGTGCACACAGCCCAGCTTGGAGCGAACGACCT
ACACCGAACTGAGATACCTACAGCGTGAGCTATGAGAAAGCGCCACGCTTCC
CGAAGGGAGAAAGGCGGACAGGTATCCGGTAAGCGGCAGGGTCGGAACAG
GAGAGCGCACGAGGGAGCTTCAGGGGGAAACGCCTGGTATCTTTATAGTC
CTGTCGGGTTTCGCCACCTCTGACTTGAGCGTCGATTTTTGTGATGCTCGTCA
GGGGGGCGGAGCCTATGGAAAAACGCCAGCAACGCGGCCTTTTTACGGTTC
CTGGGCTTTTGCTGGCCTTTTGCTCACATGTTCTTGACTCT |
| 37 | DNA | pZFN2 vector | GACTCTTCGCGATGTACGGGCCAGATATACGCGTTGACATTGATTATTGACTA
GTTATTAATAGTAATCAATTACGGGGTCATTAGTTCATAGCCCATATATGGAGT
TCCGCGTTACATAACTTACGGTAAATGGCCCGCCTGGCTGACCGCCCAACGA
CCCCCGCCCATTGACGTCAATAATGACGTATGTTCCCATAGTAACGCCAATAG
GGACTTTCCATTGACGTCAATGGGTGGACTATTTACGGTAAACTGCCCACTTG
GCAGTACATCAAGTGTATCATATGCCAAGTACGCCCCCTATTGACGTCAATGA
CGGTAAATGGCCCGCCTGGCATTATGCCCAGTACATGACCTTATGGGACTTT
CCTACTTGGCAGTACATCTACGTATTAGTCATCGCTATTACCATGGTGATGCG
GTTTTGGCAGTACATCAATGGGCGTGGATAGCGGTTTGACTCACGGGGATTT
CCAAGTCTCCACCCCATTGACGTCAATGGGAGTTTGTTTTGGCACCAAAATCA
ACGGGACTTTCCAAAATGTCGTAACAACTCCGCCCCATTGACGCAAATGGGC
GGTAGGCGTGTACGGTGGGAGGTCTATATAAGCAGAGCTCTCTGGCTAACTA
GAGAACCCACTGCTTACTGGCTTATCGAAATTAATACGACTCACTATAGGGAG
ACCCAAGCTGGCTAGCGTTTAAACTTAAGCTGATCCACTAGTCCAGTGTGGT
GGAATTCGCCATGAGATCTGACTACAAAGACCATGACGGTGATTATAAAGATC
ATGACATCGATTACAAGGATGACGATGACAAGATGGCCCCCAAGAAGAAGAG
GAAGGTGGCATTCATGGGTACCCGCCGCTATGGCTGAGAGGCCCTTCCA
GTGTCGAATCTGCATGCGTAACTTCAGTCGCTCCGACCACCTGTCCACCCAC
ATCCGCACCCACACCGGCGAGAAGCCTTTTGCCTGTGACATTTGTGGGAGGA
AATTTGCCCGCTCCGACGCCCTGGCCCGCCATACCAAGATACACACGGGCA
GCCAAAAGCCCTTCCAGTGTCGAATCTGCATGCGTAACTTCAGTCAGTCCTC
CGACCTGTCCCGCCACATCCGCACCCACACCGGCGAGAAGCCTTTTGCCTGT
GACATTTGTGGGAGGAAATTTGCCGACCGCTCCCACCTGGCCCGCCATACCA
AGATACACACGGGATCTCAGAAGCCCTTCCAGTGTCGAATCTGCATGCGTAA
CTTCAGTCAGTCCTCCGACCTGTCCCGCCACATCCGCACCCACACCGGCGA |

| SEQ ID | DNA/ PROT | Description | Sequence |
|---|---|---|---|
| | | | GAAGCCTTTTGCCTGTGACATTTGTGGGAGGAAATTTGCCCGCTCCGACCAC<br>CTGACCCAGCATACCAAGATACACCTGCGGGATCCCAGCTGGTGAAGAGC<br>GAGCTGGAGGAGAAGAAGTCCGAGCTGCGGCACAAGCTGAAGTACGTGCCC<br>CACGAGTACATCGAGCTGATCGAGATCGCCAGGAACAGCACCCAGGACCGC<br>ATCCTGGAGATGAAGGTGATGGAGTTCTTCATGAAGGTGTACGGCTACAGGG<br>GAAAGCACCTGGGCGGAAGCAGAAAGCCTGACGGCGCCATCTATACAGTGG<br>GCAGCCCCATCGATTACGGCGTGATCGTGGACACAAAGGCCTACAGCGGCG<br>GCTACAATCTGCCTATCGGCCAGGCCGACGAGATGCAGAGATACGTGAAGG<br>AGAACCAGACCCGGAATAAGCACATCAACCCCAACGAGTGGTGGAAGGTGTA<br>CCCTAGCAGCGTGACCGAGTTCAAGTTCCTGTTCGTGAGCGGCCACTTCAAG<br>GGCAACTACAAGGCCCAGCTGACCAGGCTGAACCACAAAACCAACTGCAATG<br>GCGCCGTGCTGAGCGTGGAGGAGCTGCTGATCGGCGGCGAGATGATCAAAG<br>CCGGCACCCTGACACTGGAGGAGGTGCGGCGCAAGTTCAACAACGGCGAGA<br>TCAACTTCTGATAACTCGAGTCTAGAGGGCCCGTTTAAACCCGCTGATCAGC<br>CTCGACTGTGCCTTCTAGTTGCCAGCCATCTGTTGTTTGCCCCTCCCCCGTG<br>CCTTCCTTGACCCTGGAAGGTGCCACTCCCACTGTCCTTTCCTAATAAAATGA<br>GGAAATTGCATCGCATTGTCTGAGTAGGTGTCATTCTATTCTGGGGGGTGGG<br>GTGGGGCAGGACAGCAAGGGGGAGGATTGGGAAGACAATAGCAGGCATGCT<br>GGGGATGCGGTGGGCTCTATGGCTTCTACTGGGCGGTTTTATGGACAGCAA<br>GCGAACCGGAATTGCCAGCTGGGGCGCCCTCGGTAAGGTTGGGAAGCCCT<br>GCAAAGTAAACTGGATGGCTTTCTCGCCGCCAAGGATCTGATGGCGCAGGG<br>GATCAAGCTCTGATCAAGAGACAGGATGAGGATCGTTTCGCATGATTGAACA<br>AGATGGATTGCACGCAGGTTCTCCGGCCGCTTGGGTGGAGAGGCTATTCGG<br>CTATGACTGGGCACAACAGACAATCGGCTGCTCTGATGCCGCCGTGTTCCGG<br>CTGTCAGCGCAGGGGCGCCCGGTTCTTTTTGTCAAGACCGACCTGTCCGGT<br>GCCCTGAATGAACTGCAAGACGAGGCAGCGCGGCTATCGTGGCTGGCCACG<br>ACGGGCGTTCCTTGCGCAGCTGTGCTCGACGTTGTCACTGAAGCGGGAAGG<br>GACTGGCTGCTATTGGGCGAAGTGCCGGGGCAGGATCTCCTGTCATCTCAC<br>CTTGCTCCTGCCGAGAAAGTATCCATCATGGCTGATGCAATGCGGCGGCTGC<br>ATACGCTTGATCCGGCTACCTGCCCATTCGACCACCAAGCGAAACATCGCAT<br>CGAGCGAGCACGTACTCGGATGGAAGCCGGTCTTGTCGATCAGGATGATCT<br>GGACGAAGAGCATCAGGGGCTCGCGCCAGCCGAACTGTTCGCCAGGCTCAA<br>GGCGAGCATGCCCGACGGCGAGGATCTCGTCGTGACCCATGGCGATGCCTG<br>CTTGCCGAATATCATGGTGGAAAATGGCCGCTTTTCTGGATTCATCGACTGTG<br>GCCGGCTGGGTGTGGCGGACCGCTATCAGGACATAGCGTTGGCTACCCGTG<br>ATATTGCTGAAGAGCTTGGCGGCGAATGGGCTGACCGCTTCCTCGTGCTTTA<br>CGGTATCGCCGCTCCCGATTCGCAGCGCATCGCCTTCTATCGCCTTCTTGAC<br>GAGTTCTTCTGAATTATTAACGCTTACAATTTCCTGATGCGGTATTTTCTCCTT<br>ACGCATCTGTGCGGTATTTCACACCGCATACAGGTGGCACTTTTCGGGGAAA<br>TGTGCGCGGAACCCCTATTTGTTTATTTTTCTAAATACATTCAAATATGTATCC<br>GCTCATGAGACAATAACCCTGATAAATGCTTCAATAATAGCACGTGCTAAAAC<br>TTCATTTTTAATTTAAAAGGATCTAGGTGAAGATCCTTTTTGATAATCTCATGAC<br>CAAAATCCCTTAACGTGAGTTTTCGTTCCACTGAGCGTCAGACCCCGTAGAAA<br>AGATCAAAGGATCTTCTTGAGATCCTTTTTTTCTGCGCGTAATCTGCTGCTTG<br>CAAACAAAAAAACCACCGCTACCAGCGGTGGTTTGTTTGCCGGATCAAGAGC<br>TACCAACTCTTTTTCCGAAGGTAACTGGCTTCAGCAGAGCGCAGATACCAAAT<br>ACTGTCCTTCTAGTGTAGCCGTAGTTAGGCCACCACTTCAAGAACTCTGTAGC<br>ACCGCCTACATACCTCGCTCTGCTAATCCTGTTACCAGTGGCTGCTGCCAGT<br>GGCGATAAGTCGTGTCTTACCGGGTTGGACTCAAGACGATAGTTACCGGATA<br>AGGCGCAGCGGTCGGGCTGAACGGGGGGTTCGTGCACACAGCCCAGCTTG<br>GAGCGAACGACCTACACCGAACTGAGATACCTACAGCGTGAGCTATGAGAAA<br>GCGCCACGCTTCCCGAAGGGAGAAAGGCGGACAGGTATCCGGTAAGCGGCA<br>GGGTCGGAACAGGAGAGCGCACGAGGGAGCTTCCAGGGGGAAACGCCTGG<br>TATCTTTATAGTCCTGTCGGGTTTCGCCACCTCTGACTTGAGCGTCGATTTTT<br>GTGATGCTCGTCAGGGGGCGGAGCCTATGGAAAAACGCCAGCAACGCGGC<br>CTTTTTACGGTTCCTGGGCTTTTGCTGGCCTTTTGCTCACATGTTCTT |
| 38 | DNA | CHOK1 derivative clone 1: copy Δ2 | AGCGTGCACCGAGAACAACGAATGCTGCCACCCAGAGTGCCTAGGCAGCTG<br>CCATACACCTGACGACAACACAACCTGTGTGGCCTGCCGACACTACTACTAC<br>AAAGGCGTGTGTGTGCCTGCCTGCCCACCTGGCACCTAC(Δag)GTTCGAGGG<br>CTGGCGCTGTGTGGACCGCGATTTCTGCGCCAACATCCCCAACGCTGAGAG<br>CAGTGACTCAGATGGCTTTGTCATCCACGATGGCGAGTGCATGCAAGAATGT<br>CCCTCAGGCTTCATCCGCAACAGCACCCAGAGGTCAGTGGCTCTTGTTCCCC<br>ATCCAGGAGGTGAATCTTGTTCATATTCCATGATTGTAGGAACCACCCAGAGG<br>TTCATCCAG |
| 39 | DNA | CHOK1 derivative knockout clone 2: copy Δ5 | AGCGTGCACCGAGAACAACGAATGCTGCCACCCAGAGTGCCTAGGCAGCTG<br>CCATACACCTGACGACAACACAACCTGTGTGGCCTGCCGACACTACTACTAC<br>AAAGGCGTGTGTGTGCCTGCCTGCCCACCTGGCACCTACAG(Δgttcg)AGGGC<br>TGGCGCTGTGTGGACCGCGATTTCTGCGCCAACATCCCCAACGCTGAGAGC<br>AGTGACTCAGATGGCTTTGTCATCCACGATGGCGAGTGCATGCAAGAATGTC<br>CCTCAGGCTTCATCCGCAACAGCACCCAGAGGTCAGTGGCTCTTGTTCCCCA<br>TCCAGGAGGTGAATCTTGTTCATATTCCATGATTGTAGGAACCACCCAGAGGT<br>TCATCCAG |

-continued

| SEQ ID | DNA/PROT | Description | Sequence |
|---|---|---|---|
| 40 | DNA | CHOK1 derivative knockout clone 3: copy Δ2 | AGCGTGCACCGAGAACAACGAATGCTGCCACCCAGAGTGCCTAGGCAGCTG CCATACACCTGACGACAACACAACCTGTGTGGCCTGCCGACACTACTACTAC AAAGGCGTGTGTGTGCCTGCCTGCCCACCTGGCACCTAC(Δag)GTTCGAGGG CTGGCGCTGTGTGGACCGCGATTTCTGCGCCAACATCCCCAACGCTGAGAG CAGTGACTCAGATGGCTTTGTCATCCACGATGGCGAGTGCATGCAAGAATGT CCCTCAGGCTTCATCCGCAACAGCACCCAGAGGTCAGTGGCTCTTGTTCCCC ATCCAGGAGGTGAATCTTGTTCATATTCCATGATTGTAGGAACCACCCAGAGG TTCATCCAG |
| 41 | DNA | CHOK1 derivative knock out clone 2: copy Δ22 | AGCGTGCACCGAGAACAACGAATGCTGCCACCCAGAGTGCCTAGGCAGCTG CCATACACCTGACGACAACACAACCTGTGTGGCCTGCCGACACTACTACTAC AAAGGCGTGTGTGTGCCTGCCTGCCCACCTGGC(Δacctacaggttcgagggctggc) GCTGTGTGGACCGCGATTTCTGCGCCAACATCCCCAACGCTGAGAGCAGTGA CTCAGATGGCTTTGTCATCCACGATGGCGAGTGCATGCAAGAATGTCCCTCA GGCTTCATCCGCAACAGCACCCAGAGGTCAGTGGCTCTTGTTCCCCATCCAG GAGGTGAATCTTGTTCATATTCCATGATTGTAGGAACCACCCAGAGGTTCATC CAG |
| 42 | DNA | CHOK1 derivative knock out clone 1: copy 14 nucleotides replaced and 18 added | AGCGTGCACCGAGAACAACGAATGCTGCCACCCAGAGTGCCTAGGCAGCTG CCATACACCTGACGACAACACAACCTGTGTGGCCTGCCGACACTACTACTAC AAAGGCGTGTGTGTGCCTGCCTGCCCACCTGG tgaggtataggaca gtattatagaggt ggggcAGGGCTGGCGCTGTGTGGACCGCGATTTCTGCGCCAACATCCCCAAC GCTGAGAGCAGTGACTCAGATGGCTTTGTCATCCACGATGGCGAGTGCATGC AAGAATGTCCCTCAGGCTTCATCCGCAACAGCACCCAGAGGTCAGTGGCTCT TGTTCCCCATCCAGGAGGTGAATCTTGTTCATATTCCATGATTGTAGGAACCA CCCAGAGGTTCATCCAG |
| 43 | DNA | CHOK1 derivative knock out clone 3: copy Δ114 | AGCGTGCACCGAGAACAACGAATGCTGCCACCCAGAGTGC(Δctaggcagctgcc atacacctgacgacaacacaacctgtgtggcctgccgacactactactacaaaggcgtgtgtgtgcctgc ctgcccacctggcacctacaggttcgagggc)TGGCGCTGTGTGGACCGCGATTTCTGC GCCAACATCCCCAACGCTGAGAGCAGTGACTCAGATGGCTTTGTCATCCACG ATGGCGAGTGCATGCAAGAATGTCCCTCAGGCTTCATCCGCAACAGCACCCA GAGGTCAGTGGCTCTTGTTCCCCATCCAGGAGGTGAATCTTGTTCATATTCCA TGATTGTAGGAACCACCCAGAGGTTCATCCAG |
| 44 | DNA | CHO-DUXB11 derivative knock out clone: sequence Δ22 | AGCGTGCACCGAGAACAACGAATGCTGCCACCCAGAGTGCCTAGGCAGCTG CCATACACCTGACGACAACACAACCTGTGTGGCCTGCCGACACTACTACTAC AAAGGCGTGTGTGTGCCTGCCTGCCCACCTGG(Δcacctacaggttcgagggctgg)C GCTGTGTGGACCGCGATTTCTGCGCCAACATCCCCAACGCTGAGAGCAGTGA CTCAGATGGCTTTGTCATCCACGATGGCGAGTGCATGCAAGAATGTCCCTCA GGCTTCATCCGCAACAGCACCCAGAGGTCAGTGGCTCTTGTTCCCCATCCAG GAGGTGAATCTTGTTCATATTCCATGATTGTAGGAACCACCCAGAGGTTCATC CAG |
| 45 | DNA | CHO-DUXB11 derivative knock out clone: sequence Δ7 | AGCGTGCACCGAGAACAACGAATGCTGCCACCCAGAGTGCCTAGGCAGCTG CCATACACCTGACGACAACACAACCTGTGTGGCCTGCCGACACTACTACTAC AAAGGCGTGTGTGTGCCTGCCTGCCCACCTGGCACCTACA(Δggttcga)GGGC TGGCGCTGTGTGGACCGCGATTTCTGCGCCAACATCCCCAACGCTGAGAGC AGTGACTCAGATGGCTTTGTCATCCACGATGGCGAGTGCATGCAAGAATGTC CCTCAGGCTTCATCCGCAACAGCACCCAGAGGTCAGTGGCTCTTGTTCCCCA TCCAGGAGGTGAATCTTGTTCATATTCCATGATTGTAGGAACCACCCAGAGGT TCATCCAG |
| 46 | DNA | shRNA custom forward primer | AGGCGATTAAGTTGGGTA |
| 47 | DNA | T7 primer for shRNA vector sequencing (reverse strand) | TAATACGACTCACTATAGGG |

EXAMPLES

Figure 8:
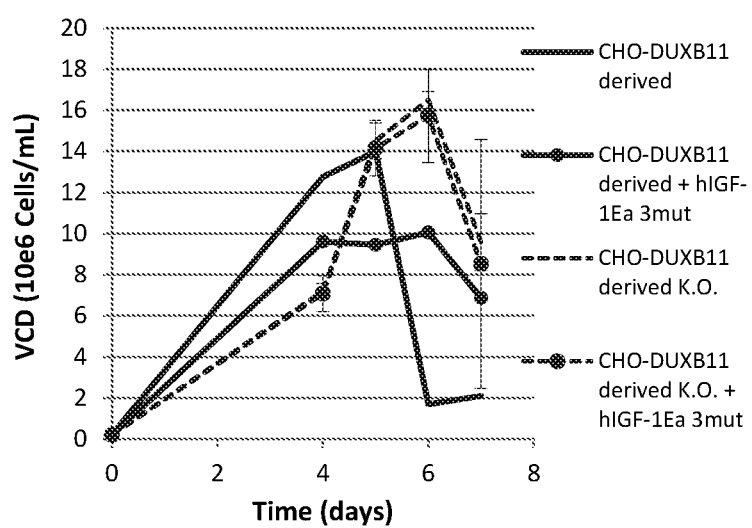
FIG. 8: In bolt the cell growth of parental CHO-DUXB11 derived cells and in bolt lines with circles the reduced cell growth during co-cultivation with hIGF-1Ea 3mut is shown. With dashed lines the cell growth average of the two IGF-1R KO clones are shown (error bars: standard error of the mean). The cell growth is improved compared to the wild-type parental CHO-DUXB11 derived cells. The co-cultivation with hIGF-1Ea 3mut resulted in no cell growth inhibition for the one KO clone and minor cell growth inhibition for the second IGF-1R KO clone.
Figure 9:
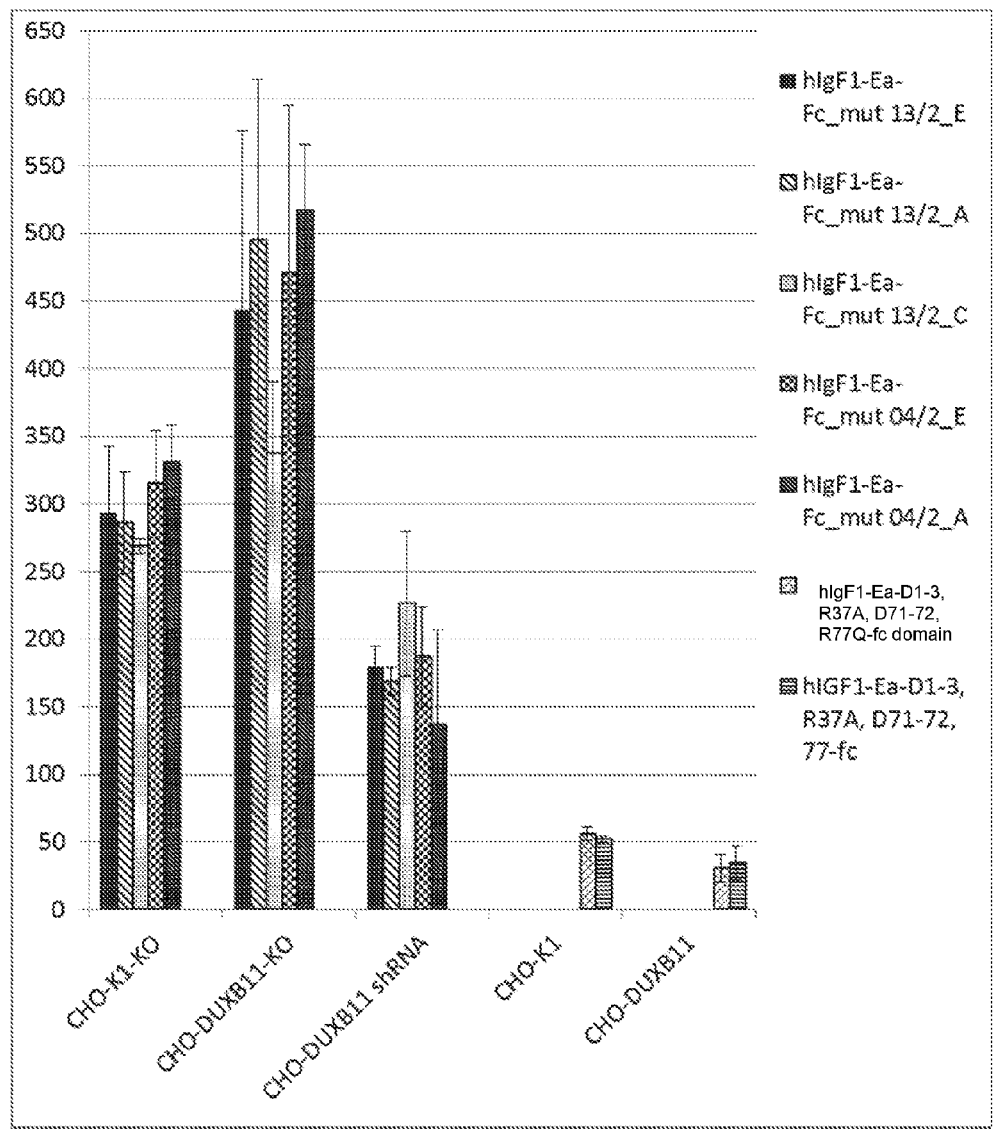
FIG. 9: IGF-1-Fc fusion protein titers of 14 day batch cultures are shown (pool level). The expressions of 7 different IGF-1-Fc fusion proteins in 5 different cell lines are highlighted. The expression of IGF-1-Fc fusion proteins was 5-20 fold increased in CHO-K1 derivative IGF-1R-KO cell lines, CHO-DUXB11 derivative IGF-1R-KO cell lines as well as in CHO-DUXB11 derivative shRNA (reduced expression of IGF-1R and INSR) cell lines compared to the CHO-K1 or CHO-DUXB11 derivative wildtype cell lines.

Expression of recombinant IGF-1 in CHO cell lines results in cell growth inhibition (FIGS. 1, 2) and low titers. Stable knockdown/knockout of IGF1-R in CHO cells using shRNA technology or "zinc finger nuclease" technology surprisingly resulted in an improved cell growth and higher IGF-1 protein titers (FIGS. 6, 7, 8, 9 and 10). CHO cells with reduced expression of IGF-1-R (knockdown) which were stable transfected with plasmids encoding IGF-1 produced ca. 5 fold higher pool titer compared to stable transfected wild type CHO cells. Even higher pool titer could be measured after stable transfection of IGF-1R knockout cell lines. A 5-20 fold titer increase of recombinant IGF-1 could be detected compared to the wild type CHO cell line (FIG. 9). In summary these data show that knockdown or knockout of receptor genes in mammalian cell lines can significantly improve the production of difficult to express therapeutic proteins.

Part A: General Methodology

The present invention is now described by means of non-limiting examples, which however, constitute preferred embodiments of the present invention.

I. Cell Culture Methods and Transfection

Appropriate methods for transfecting and culturing the host cells according to the present invention for expressing a therapeutic protein of interest are known to the person skilled in the art. The following is disclosed by means of examples.

Example 1

Cell Culturing

Suspension growing CHO cells are cultivated in shake flasks in a standard medium as disclosed in e.g. U.S. Pat. No. 6,048,728. Cells are passaged 2 times per week into fresh media and are maintained in logarithmic growth phase throughout the study.

Example 2

Transfection

For transfection, parental CHO cells in exponential growth phase with viability over 95 percent were used. Transfections by electroporation (nucleofection) was done using the Amaxa™, Nucleofector™ Technology according to the instructions of the manufacturer (Lonza). $5 \times 10^6$ cells were centrifuged 10 min at 90 g, and resuspended in 100 µl transfection reagent ('Solution V') (Lonza). Nothing (negative control of transfection) or 30 pmol siRNA or 3 µg linearized DNA vector (shRNA vector or vector coding for an IGF-1 variant (e.g. of SEQ ID NOs.: 23-29) or a homogeneous mix of 6 µg or 10 µg of both vectors coding for Zinc finger nucleases (pZFN1 and 2 (SEQ ID NOs.: 36/37)), were added to the cells, and the whole mixture was transferred in an electroporation cuvette. After nucleofection (program: U-23), cuvette was rinsed with 1 ml pre-warmed (37 degrees centigrade) culture medium, and cells were added to 20 ml pre-warmed medium in a 125 ml shake-flask and incubated for 2 days at 37 degrees centigrade and 10 percent $CO_2$.

Example 3

Puromycin/Geneticin Selection

Selection was started 48 h after transfection. The puromycin/geneticin selection marker located on the expression vector nucleic acid allows selection for puromycin/G418 resistance. For selection of transfectants, cells were cultivated in the presence of 5 µg/ml puromycin (PAA)/0.8 mg/ml G418 (Invitrogen) up to cells recover to a viability above 80 percent. About four/two weeks after transfection and puromycin/G418 selection, pool populations consisting predominantly of puromycin/G418 resistant cells emerge. Cells were frozen after pool recovery.

Example 4

Gene Amplification of G418 Resistant Cells

An even more stringent selection of the G418 resistant cells was initiated by passaging the cells to a G418 free, MTX containing culture medium (1 µM). After three weeks of cultivation, a MTX resistant and high producing cell pool was generated. The DHFR (dihydrofolate reductase) selection marker allows stringent selection of high producing cells by adding the folic acid analogue methotrexate (MTX) to the culture media, resulting in increased titers for transfection pools. After recovery of the cells from the MTX selection, cells were frozen, and cultivation was continued in MTX containing medium throughout FACS cloning and screening.

Example 5

Establishment of Clonal Cell Lines by Fluorescence-activated Cell Sorting (FACS)

To obtain a clonal cell line (i.e., a cell line derived from a single cell), the pool of transfected cells was seeded out in 96 well plates. $1 \times 10^7$ cells per transfected pool or 'superpool' (harmonized mix of several pools) were centrifuged and washed with 5 ml of chilled PBS (phosphate buffered saline) and re-suspended in 1 ml cold PBS. For shRNA and pZFN transfected cells, a suitable amount of Cy5 labeled hIGF-1Ea 3mut was added. Cells were incubated on ice for 30 min in the dark, subsequently washed twice with 5 ml of chilled PBS and re-suspended in 1 ml cold PBS. Cells were filtrated and dispensed into a FACS tube for sorting or/and cloning. The cell cloning was performed with a FACS Aria (Becton Dickinson). shRNA and pZFN transfected CHO cells were single cell sorted. In order to select only cells with less or no functional IGF-1R expression, only the 5% lowest Cy5 fluorescent cells were selected. Cells were scaled up using standard procedures. Individual clones were evaluated either for IGF-1R mRNA expression or for mutations in IGF-1R exon 3, the lowest IGF-1R mRNA expressing or IGF-1R knock out clones being retained after cultivation and analysis. From these candidates, the cell line with appropriate growth in presence of hIGF-1 Ea 3mut or rhIGF-1 was chosen for transfection with an IGF-1 variant of SEQ ID NOs.: 23-29 coding vectors. The clone with the highest productivity was chosen for production of the recombinant protein. The productivity can usually be further improved by establishing/adapting the culturing conditions i.e. by or adapting bioprocess parameters (e.g. temperature, feeds, oxygen and temperature shift).

Example 6

Bacterial Cloning of Circular Vectors

One Shot Stbl3 bacteria (Invitrogen, catalog C7373-03) were transformed with the vector to be cloned following the manufacturer's instructions and spread on agarose plates containing a suitable concentration of antibiotic. Antibiotics used were Kanamycin at 25 µg/ml or Ampicillin at 100 µg/ml. After overnight incubation, distinct grown bacterial colonies were picked and expanded in 2 ml antibiotic containing LB Broth for 8 h, and further expanded in 100 ml for 15 h. The DNA vector was purified using the Endofree Plasmid Maxi kit (Qiagen, catalog 12362), following the manufacturer's instructions. The vector sequence required for genome editing was validated by Sanger sequencing using vector-specific forward and reverse primers. The vectors with the correct sequence were further used.

Example 7

Spike-in Experiments

Cell cultures were passaged at a density of 2×10$^5$ viable cell/ml in standard medium (50 ml culture). A suitable amount of sterile filtrated (0.22 µm filter) hIGF-1Ea 3mut or rhIGF-1 was added for a final concentration of 50 mg/l. Both triggered cell growth inhibition of CHO-K1 and CHO-DUXB11 derivative parental cell. Cells were cultivated under standard conditions, and cell viability and density were regularly measured on a 24 h basis.

Example 8

Cultivation of Transfected CHO Cells Expressing IGF-1 in Bioreactor

For cultivation of transfected cells expressing IGF-1 in bioreactor a Fed-Batch process was applied. The process events such as feedstart and temperature shift were timed to support cell growth and to extend the production phase by maintaining viability (Niraj Kumar, Patrick Gammell, Martin Clynes (2007) Proliferation control strategies to improve productivity and survival during CHO based production culture; Cytotechnology (2007) 53:33-46).

Example 9

Harvesting of IGF-1 from CHO Cells

As harvest procedure a standard cell separation techniques with depth filtration followed by sterile filtration was applied. The CHO cells were cultivated and harvested according to standard methods known to the person skilled in the art (e.g. Curr. Protoc. Protein Sci. 2001 May; Chapter 5: Unit 5.10. Production of recombinant proteins in mammalian cells. Chen S, Gray D, Ma J, Subramanian S; (Mahesh Prashada, Klaus Tarrach (2006) Depth filtration: Cell clarification of bioreactor offloads, Filtration & Separation Volume 43, Issue 7, September 2006, Pages 28-30).

II. Vector Constructions

Several vector assemblies according to the teachings of the present invention are feasible. As the individual elements of the vector are known in the prior art, suitable vectors can be assembled e.g. by sequencing or amplification and appropriate cloning of the basic genetic elements and expression cassettes in the desired orientation. Respective cloning methods are state of the art and also the sequence of the genetic elements described above are described in the prior art. Subsequently, the generation of vector constructs is described by way of example. However, it is understood by those of skill in the art that several other embodiments and ways to obtain respective vectors are suitable and readily available. All plasmid constructs (e.g. pBW679) described in this section are based on the mammalian expression vectors described in WO2009080720. The example section of WO2009080720, particularly FIG. 1, table 1 and the example section II: vector constructions (page 21-31) are herein incorporated by reference.

Example 10 shRNA Vector Construction

Six sense (SED ID NOs.: 5-10) and six corresponding antisense hairpin siRNA template oligonucleotides were synthesized, annealed and ligated into the pSilencer™ 2.1-U6 puro expression vector (Ambion, part number AM5762) following the manufacturer's instructions. Those ligation products were cloned in E. Coli as described in example 6, using 100 µg/ml Ampicillin. Three colonies for each of the six shRNA vectors were picked and expanded. The sequences of the purified DNA vectors were validated using a custom forward primer (SEQ ID NO.: 46) and the T7 reverse primer (SEQ ID NO.: 47). DNA vectors with the correct forward and reverse sequences were linearized with SspI (NEB, catalog R0132S), purified with isopropanol and ethanol precipitations and re-suspended in nuclease-free water before transfection. Two transfection replicates were performed for each of those six shRNA vectors (thus 12 pools were generated) and one transfection was done for the scrambled shRNA control (included in the pSilencer™ 2.1-U6 puro expression vector kit). Transfected cells were selected with puromycin (example 3). The two pools corresponding either to shRNA 1, 4 or 6 (SEQ ID NOs.: 5, 8, 9) were superpooled respectively and all six pools transfected with shRNAs 2, 3 and 5 (SEQ ID NOs.: 6, 7, 9) were homogeneously combined in a superpool, before staining with Cy5 labeled hIGF-1Ea 3mut and single cell cloning using FACS (example 5).

Example 11

Design/Production and Use of ZFNs which are Specific for Exon 3 of IGF-1R

Exon 3 of IGF-1R and the flanking introns were sequenced in CHO-K1 and CHO-DUXB11 derivative parental cell lines (SEQ ID NO.: 14/15). First, exon 3 was sequenced based on proprietary hamster cDNA sequence covering exon 3, as well as mouse sequence of IGF-1R gene. PCR primers were designed on conserved parts and resulting PCR products were sequenced. Based on the exon 3 sequence Sigma sequenced the exon 3 flanking introns and engineered two ZFNs targeting IGF-1R exon 3. Each ZFN is targeting and binding to 18 nucleotides on the reverse (on the 5') respectively the forward (on the 3') DNA strand. The two binding sites are separated by the five nucleotides of the cutting site (SEQ ID NO.: 11). Product description and methods are available from Sigma (described in '74188 CompoZr Custom ZFN Tech Bulletin'). Sigma also designed forward and reverse PCR primers in the surrounding intron sequences (SEQ ID NO.: 12 and 13) to amplify IGF-1R exon 3 on gDNA level, resulting in a 501 bp PCR product. Sigma provided CompoZr™ (custom Zinc Finger Nucleases, product number CSTZFN-1KT, lot number 08021019MN) comprising 20-25 µg of two DNA vectors, coding for the reverse (pZFN1) respectively the forward (pZFN2) strand-recognizing engineered ZFN.

E. Coli were transformed—according to well-known transformation protocols—(see example 6) with either vector and spread on 25 µg/ml Kanamycin containing agarose plates. For each vector, 4 bacterial colonies were picked and expanded. The ZFN sequences of the four purified DNA plasmid samples of each pZFN were validated using T7 forward and BHG reverse primers and pooled. 6 µg or 10 µg of a homogeneous mix of circular pZFN1 and pZFN2 vectors were transfected in CHO-K1 derivative cell and CHO-DUXB11 derivative parental cells using electroporation (Amaxa). Three replicate transfections were performed for each quantity, resulting in six pools for each parental cell line. To measure the cleavage efficiency of ZFNs in the pools, the Surveyor Mutation Detection assay (Transgenomics, catalog 706025) was used at days 3 and 10 after transfection (counted as day zero). The genomic DNA of the pools was isolated using the GenElute Mammalian Genomic DNA Miniprep kit (Sigma, catalog G1N70-1KT), the exon 3 amplified in a PCR reaction using the forward and reverse sequencing primers of IGF-1R (SEQ ID NO.: 12 and 13). The PCR product was then denatured at 95 C degree. The temperature was gradually lowered and some wild-type and mutated product hybridize to form double strand DNA with mismatches around the cleavage site, which was cleaved by Surveyor® enzyme. The final products were analyzed using a capillary gel electrophorese system (LAB901). Additional to the expected 501 bp perfect match PCR product, two smaller bands of approximately 277 bp and 224 bp were detected in all six pools of both cell lines, corresponding to the fragments on either side of the cutting site, thus attesting ZFN activity in CHO-K1 and CHO-DUXB11 derivative parental cells. Seven days after transfection, the pools were single cell cloned (as described in Example 5) in 10×96 well plates.

Overall 507 clones of pZFN-transfected CHO-K1 derivative cell line were assessed for mutations using the Surveyor Mutation Detection assay described above (the genomic DNA of clones is extracted in 96-well plates using Extract-N-Amp Blood PCR kit from Sigma, catalog XNAB2). In 42 clones two smaller bands were detected indicating that their genome contains at least one mutated copy of exon 3. Subsequently IGF-1R exon 3 of these clones was sequenced. The DNA sequencing chromatograms showed two overlaying signals of same intensity, indicating two copies of the target sequence. Six of the 42 clones had IGF-1R mutations in both copies, among which two clones had frame shift mutations in both copies (clones 1 and 2, SEQ ID NO.: 38, 39, 41 and 42), and one clone (3) had a frame shift mutation in one copy and a 114 bp deletion in the other (SEQ ID NO.: 40 and 43). The IGF-1R sequences in those 3 clones were confirmed by TOPO cloning (TA cloning kit, Invitrogen, cat. K4575-40; 6 bacterial colonies picked). All three K.O. clones were growing to significantly higher viable cell densities than the parental cells. Spike-in in of 50 mg/L of hIGF-1Ea 3mut' (SEQ ID NO.: 35) resulted in similar cell grow behavior as parental cells in standard medium (FIG. 8). The clone with the genotype Δ5/Δ22 (SEQ ID NO.: 39/41) was selected for transfection with the Insulin like growth factor 1 protein, e.g. the human IGF-1 (SEQ ID NO.:16 or 20) or a variant thereof (e.g. SEQ ID NOs.: 21-29).

Single cell cloning of pZFN-transfected CHO-DUXB11 derivative cell line resulted in 117 clones which were assessed for mutations with Surveyor assay as described above. Overall 28 clones had at least one mutated copy of IGF-1R exon 3 (two smaller bands detected), but sequencing indicated that all those clones still contains wild type copies. Two clones, in which mutated sequences were detected (Δ22 or Δ16) were a second time transfected with pZFNs and six pools were generated using 10 μg of mixed pZFNs. Seven days after transfection, these pools were single cell sorted in 6×96 well plates (as described in Example 5). Overall 211 clones were sequenced for IGF-1R exon3 (no Surveyor assay possible anymore as already a mutated sequence existent) and overlapping sequences analyzed on chromatograms. Overall ca. 20% of the clones had a wild type and two mutated sequences (mostly deletions around the cutting site). Three clones, with the genotype Δ22/Δ7/wildtype, Δ16/Δ7/wildtype and Δ16/Δ22/wildtype, were selected for a third round of transfection with pZFNs (their sequences were confirmed by TOPO cloning). Two transfections with 8 μg of mixed pZFNs were performed for each of the three clones. After 7-9 days the two pools corresponding to a clone were merged. In order to enrich the cells with non functional IGF-1R, the three resulting pools were 6-8 weeks co-cultivated in presence of 50 mg/l hIGF-1Ea 3mut. Two days before single cell cloning the cells were cultivated without hIGF-1Ea 3mut (to allow binding of Cy5 labelled hIGF-1Ea 3mut and select the 5% lowest fluorescent cells). The three pools were single cell sorted in 9×96 well plates.

A PCR primer binding the wild type cutting site sequence in IGF-1R exon 3 was designed, allowing an efficient screening of mutated clones. The PCR was performed together with the forward sequencing primer for IGF-1R (assuming the PCR results in a PCR product if the cells contain wild type IGF-1R sequence). Overall 389 clones were screened and 58 PCR-negative clones were sequenced. In 30 of those clones no wild type sequence could be detected, among which 22 clones contained frame shift mutations (13 clones with sequences Δ22/Δ7). Their cell growth with and without co-cultivation of 50 mg/l hIGF-1Ea 3mut was evaluated, and the best growing clone in presence of hIGF-1Ea 3mut, with the genotype Δ22/Δ7 (SEQ ID NO.: 44/45), was selected for transfection with DNA constructs encoding the proteins of SEQ IDs No.: 21-29.

Example 12

Cloning Strategy of Vector pBW806 (hIGF1-Ea-fc_mut 13/2_A) (FIG. 11)

Vector pBW806, encoding the hIGF1-Ea-fc_mut 13/2_A, was prepared following two consecutive cloning steps. In a first step plasmid 11AARNSC_hIGF1-Ea-fc_mut 13/2_E_pMA-T (Novartis propriety vector) was digested with XbaI and AscI in order to extract the de novo synthesized Fc region. In parallel pBW679 (Novartis propriety vector) was digested with AscI and XbaI generating the corresponding backbone fragment carrying transcriptional and translational regulatory elements as well as a G418/DHFR selection/amplification marker. Both digested elements were ligated by their compatible ends resulting in the intermediate vector pBW805. In a second step plasmid 11AARNUC_hIGF1-Ea-fc_mut 13/2_A_pMA-T (Novartis propriety vector) was digested with XbaI and Sse232I in order to extract the n-terminal region of the hIGF1-Ea-fc_mut 13/2_A fusion protein. In parallel the intermediate vector pBW805 was subsequently digested with Sse232I and XbaI delivering the desired backbone fraction which finally was ligated with the 11AARNUC_hIGF1-Ea-fc_mut 13/2_A_pMA-T fragment resulting in the final expression vector pBW806.

Cloning Strategy of Vector pBW807 (hIGF1-Ea-fc_mut 13/2_C) (FIG. 12)

Vector pBW807, encoding the hIGF1-Ea-fc_mut 13/2_C, was prepared following two consecutive cloning steps. In a first step plasmid 11AARNSC_hIGF1-Ea-fc_mut 13/2_E_pMA-T (Novartis propriety vector) was digested with XbaI and AscI in order to extract the de novo synthesized Fc region. In parallel pBW679 (Novartis propriety vector) was digested with AscI and XbaI generating the corresponding backbone fragment carrying transcriptional and translational regulatory elements as well as a G418/DHFR selection/amplification marker. Both digested elements were ligated by their compatible ends resulting in the intermediate vector pBW805. In a second step plasmid 11AARNWC_hIGF1-Ea-fc_mut 13/2_C_pMA-T (Novartis propriety vector) was digested with XbaI and Sse232I in order to extract the n-terminal region of the hIGF1-Ea-fc_mut 13/2_C fusion protein. In parallel the intermediate vector pBW805 was subsequently digested with Sse232I and XbaI delivering the desired backbone fraction which finally was ligated with the 11AARNUC_hIGF1-Ea-fc_mut 13/2_C_pMA-T (Novartis propriety vector) fragment resulting in the final expression vector pBW807.

Cloning Strategy of Vector pBW808 (hIgF1-Ea-Fc_mut 13/2_F) (FIG. 13)

Vector pBW808, encoding the hIgF1-Ea-Fc_mut 13/2_F (Novartis propriety vector), was prepared following two consecutive cloning steps. In a first step plasmid 11AARNSC_hIGF1-Ea-fc_mut 13/2_E_pMA-T (Novartis propriety vector) was digested with XbaI and AscI in order to extract the de novo synthesized Fc region. In parallel pBW679 (Novartis propriety vector) was digested with AscI and XbaI generating the corresponding backbone fragment carrying transcriptional and translational regulatory elements as well as a G418/DHFR selection/amplification marker. Both digested elements were ligated by their compatible ends resulting in the intermediate vector pBW805. In a second step plasmid 11AARNYC_hIgF1-Ea-Fc_mut 13/2_F_pMA-T (Novartis propriety vector) was digested with XbaI and Sse232I in order to extract the n-terminal region of the hIgF1-Ea-Fc_mut 13/2_Fc fusion protein. In parallel the intermediate vector pBW805 was subsequently digested with Sse232I and XbaI delivering the desired backbone fraction which finally was ligated with the 11AARNUC_hIgF1-Ea-Fc_mut 13/2_F_pMA-T (Novartis propriety vector) fragment resulting in the final expression vector pBW808.

Cloning Strategy of Vector pBW809 (hIGF1-Ea-fc_mut 04/2_E) (FIG. 14)

Vector pBW809, encoding the HIGF1-EA-FC_MUT 04/2_E Fc fusion sequence, was prepared following two consecutive cloning steps. In a first step plasmid 11AARNSC_hIGF1-Ea-fc_mut 13/2_E_pMA-T (Novartis propriety vector) was digested with XbaI and AscI in order to extract the de novo synthesized Fc region. In parallel pBW679 (Novartis propriety vector) was digested with AscI and XbaI generating the corresponding backbone fragment carrying transcriptional and translational regulatory elements as well as a G418/DHFR selection/amplification marker. Both digested elements were ligated by their compatible ends resulting in the intermediate vector pBW805. In a second step plasmid 11AARN2C_hIGF1-Ea-fc_mut 04/2_E_pMA-T (Novartis propriety vector) was digested with XbaI and Sse232I in order to extract the n-terminal region of the hIGF1-Ea-fc_mut 04/2_E fusion protein. In parallel the intermediate vector pBW805 was subsequently digested with Sse232I and XbaI delivering the desired backbone fraction which finally was ligated with the 11AARNUC_hIGF1-Ea-fc_mut 04/2_E_pMA-T (Novartis propriety vector) fragment resulting in the final expression vector pBW809.

Cloning Strategy of Vector pBW810 (hIGF1-Ea-fc_mut 04/2_A) (FIG. 15)

Vector pBW810, encoding the hIGF1-Ea-fc_mut 04/2_A, was prepared following two consecutive cloning steps. In a first step plasmid 11AARNSC_hIGF1-Ea-fc_mut 13/2_E_pMA-T (Novartis propriety vector) was digested with XbaI and AscI in order to extract the de novo synthesized Fc region. In parallel pBW679 (Novartis propriety vector) was digested with AscI and XbaI generating the corresponding backbone fragment carrying transcriptional and translational regulatory elements as well as a G418/DHFR selection/amplification marker. Both digested elements were ligated by their compatible ends resulting in the intermediate vector pBW805. In a second step plasmid 11AARN2C_hIGF1-Ea-fc_mut 04/2_A_pMA-T (Novartis propriety vector) was digested with XbaI and Sse232I in order to extract the n-terminal region of the hIGF1-Ea-fc_mut 04/2_A fusion protein. In parallel the intermediate vector pBW805 was subsequently digested with Sse232I and XbaI delivering the desired backbone fraction which finally was ligated with the 11AARNUC_hIGF1-Ea-fc_mut 04/2_A_pMA-T (Novartis propriety vector) fragment resulting in the final expression vector pBW810.

Cloning Strategy of Vector pBW410 (hIGF-1Ea 3mut) (FIG. 16)

Vector 0610900pGA4 (Novartis propriety vector), encoding the hIGF-1Ea 3mut sequence was digested with XbaI and MluI in order to extract the de novo synthesized coding IGF sequence. In parallel pBW165 (Novartis propriety vector) was digested with MluI and XbaI generating the corresponding backbone fragment carrying transcriptional and translational regulatory elements as well as a G418/DHFR selection/amplification marker. Both digested elements were ligated by their compatible ends resulting in the final expression vector pBW410.

Cloning Strategy of Vector pBW664 (hIGF1-Ea-Δ1-3, R37A, Δ71-72, 77-fc Domain) (FIG. 17)

Vector 0905915 (Novartis propriety vector), encoding the hIGF1-Ea-Δ1-3, R37A, Δ71-72, 77-fc domain sequence was digested with XbaI and AscI in order to extract the de novo synthesized coding IGF sequence. In parallel pBW596 (Novartis propriety vector) was digested with AscI and XbaI generating the corresponding backbone fragment carrying transcriptional and translational regulatory elements as well as a G418/DHFR selection/amplification marker. Both digested elements were ligated by their compatible ends resulting in the final expression vector pBW664.

Cloning Strategy of Vector pBW666 (hIGF1-Ea-Δ1-3, R37A, Δ71-72, R77Q-fc Domain) (FIG. 18)

Vector 0950919 (Novartis propriety vector), encoding the hIGF1-Ea-Δ1-3, R37A, Δ71-72, R77Q-fc domain sequence was digested with XbaI and AscI in order to extract the de novo synthesized coding IGF sequence. In parallel pBW596 (Novartis propriety vector) was digested with AscI and XbaI generating the corresponding backbone fragment carrying transcriptional and translational regulatory elements as well as a G418/DHFR selection/amplification marker. Both digested elements were ligated by their compatible ends resulting in the final expression vector pBW666.

Figure 2:
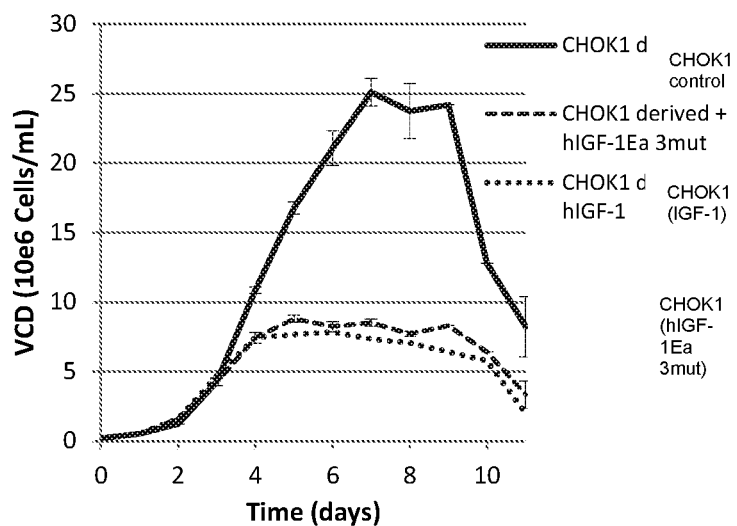
FIG. 2: A: Cell growth: The continuous line shows the viable cell density (VCD) of CHO-K1 derivative cells. During co-cultivation with hIGF-1Ea 3mut or hIGF-1 the cell growth is inhibited (dashed and dotted line, respectively). The average of 3 biologic replicates is shown (except for hIGF-1 spike-in; error bars: standard error of the mean). hIGF-1Ea 3mut/hIGF-1 was spiked on day 0 (spike-in experiment). B: Cell viability: The continuous line shows the cell viability of CHO-K1 derivative cell, the dashed respectively dotted line the reduced cell viability after hIGF-1Ea 3mut/hIGF-1 spike in. The average of 3 biologic replicates is shown (except for hIGF-1 spike-in; error bars: standard error of the mean). The cell viability drops two days earlier if the cells were co-incubated with hIGF-1Ea 3mut/hIGF-1. No difference between hIGF-1 and hIGF-1Ea 3mut in cell growth or cell viability could be detected.
Figure 2:
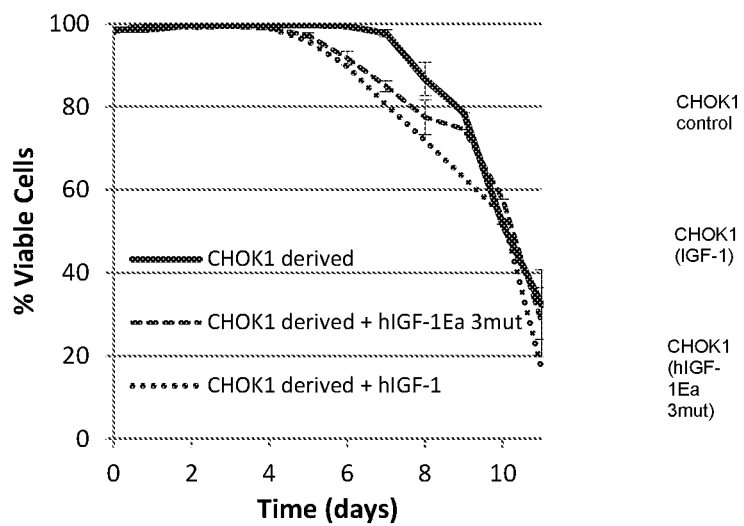

Results:

Expression of recombinant IGF-1 in CHO cell lines results in cell growth inhibition and low titers. The maximum titer measurement of hIGF-1Ea 3mut was 8 ug/ml which corresponds to 100 mg/L of an antibody titer (based on molar mass). The average titer measurements of a recombinant antibody in bioreactor process are around 3 g/L. One cause of the low titer of IGF-1 is reduced cell growth and low cell viability of IGF-1 expressing cells. During an antibody expression process CHO-K1 derivative cell cells grow up to $2 \times 10^7$ cells/ml and the cell viability is over 97% during the first 230-260 h cultivation time. In contrast CHO-K1 derivative cells expressing IGF-1 grow only up to $0.5 \times 10^7$ cells/ml and the cell viability drops already after 2 days under 97% (see FIG. 1). The reduced cell growth could also be detected during co-cultivation of non-transfected CHO-K1 derivative cells with IGF-1. FIG. 2 shows that parental CHO-K1 derivative cells grow up to $2.5 \times 10^7$ cells/ml. During co-cultivation of CHO-K1 derivative cells with rhIGF1 or hIGF-1Ea 3mut (50 mg/L) cell growth is also significantly inhibited ($0.9 \times 10^7$ cells/ml) (see FIG. 2).

Figure 3:
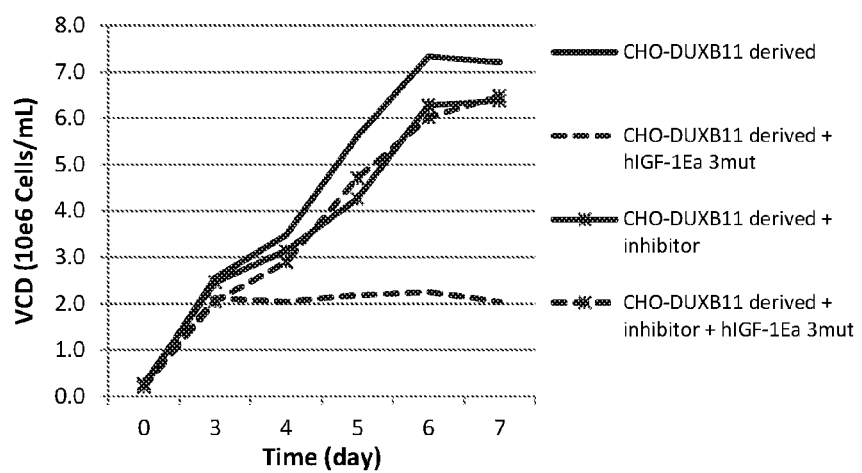
FIG. 3: Viable cell density (VCD) of CHO-DUXB11 derivative cells (bold line) and the reduced cell growth during co-cultivation with hIGF-1Ea 3mut (dotted line) are shown. After adding the IGF-1R tyrosine kinase inhibitor NVPAEW541 (bold line with asterisk) the cell growth is slightly reduced. Co-cultivation with hIGF-1Ea 3mut after adding the IGF-1R tyrosine kinase inhibitor resulted in no further cell growth inhibition (dotted line with asterisk) (cells were incubated for 1 h with NVPAEW541 before spike-in of hIGF-1Ea 3mut, to let time for the inhibitor to bind).

In the next step a specific IGF-1R tyrosine kinase inhibitor (NVPAEW541) (In vivo antitumor activity of NVPAEW541—A novel, potent, and selective inhibitor of the IGF-IR kinase; Carlos Garcia-Echeverria et al.; Cancer Cell; Published Online Feb. 26, 2004 DOI: 10.1016/S1535610804000510) was added during hIGF-1Ea 3mut co-cultivation experiments in CHO-DUXB11 derivative cells. The cell growth inhibition could be prevented (see FIG. 3). This verifies that IGF-1R triggers a signal into the cell resulting in cell growth inhibition.

Figure 4:
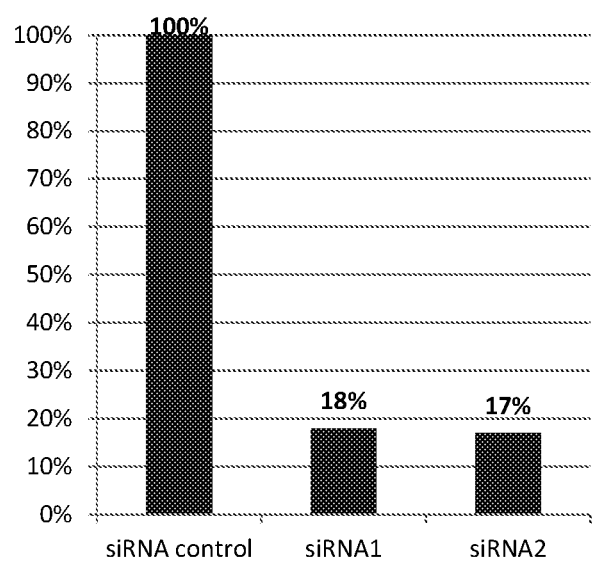
FIG. 4: IGF-1R mRNA expression quantified by real-time RT-PCR after siRNA transfection in CHO-DUXB11 derived parental cells. Percentage of IGF-1R mRNA level in cells transfected with two different siRNA against IGF-1R in comparison to cells transfected with scrambled siRNA (equate 100%), at day 4 after transfection. IGF-1R mRNA levels of samples were normalized (GAPDH).

To confirm these findings transfection of a CHO-DUXB11 derived cells with siRNA and shRNA vectors were performed (si- and shRNA against IGF-1R). Two different siRNAs (SEQ ID NOs.: 1-4) against IGF-1R and a control siRNA (scrambled) were used. The scrambled sequence was included to discount any changes to the gene expression profile that may result from the siRNA delivery method. This siRNA is not complementary to any known gene in the Chinese hamster. Both siRNAs tested reduced the mRNA level of IGF-1R of more than 80% (see FIG. 4).

To generate a cell line which has a permanent reduced expression of IGF-1R, parental CHO-DUXB11 derived cells were transfected with vectors expressing shRNA against IGF-1R (SEQ ID NOs.: 5-10). Overall 6 different shRNA sequences against IGF-1R were evaluated (see FIG. 5). Up to 94% reduced gene expression of IGF-1R could be achieved with this approach (shRNA4) on pool level.

Figure 5:
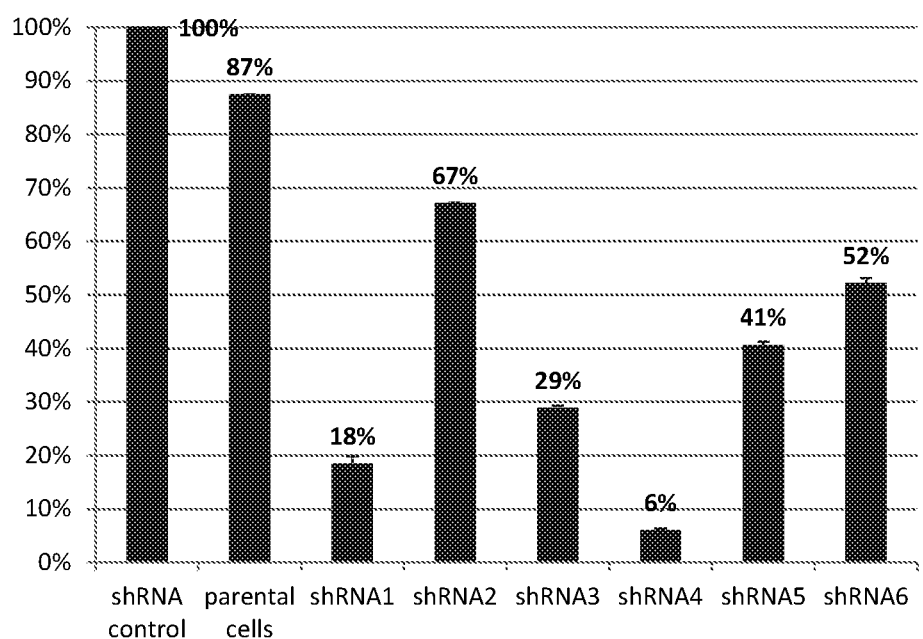
FIG. 5: IGF-1R mRNA expression quantified by real-time RT-PCR after stable shRNA transfection and puromycin selection in CHO-DUXB11 derived parental cells (pool level). Percentage of IGF-1R mRNA level of cells transfected with six different shRNA against IGF-1R in comparison to cells transfected with scrambled shRNA (equate 100%), at culture day 5 of a 50 ml cell culture. IGF-1R mRNA levels of samples were normalized to GAPDH. shRNA 4 showed the best effect in repressing IGF-1R expression.
Figure 6:
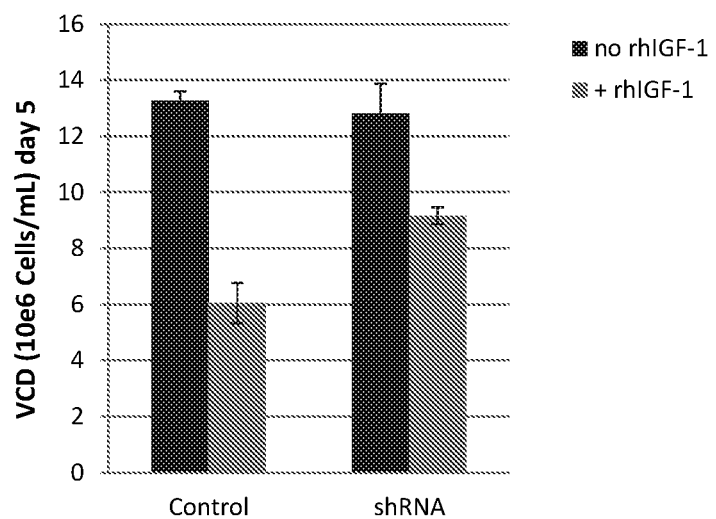
FIG. 6: Highlighted are the viable cell density (VCD) of IGF-1R knockdown clones and the CHO-DUXB11 derived control clones (Control) in presence and absence of hIGF-1Ea 3mut, at culture day 5 of a 50 ml batch. The IGF-1R knockdown clones (shRNAs; n=12 best shRNA clones) show an improved cell growth in presence of hIGF-1Ea 3mut compared to parental CHO-DUXB11 derived control clones (n=7) (error bars: standard error of the mean).

The shRNA pools shown in FIG. 5 were single cell cloned using FACS technique. This technology enables rapid identification and isolation of clones with a specific property (e.g. high antibody producer) from a heterogeneous population of transfected cells, decreasing the labor and time associated with standard limiting dilution cloning methods (Borth N, Zeyda M, Kunert R, Katinger H. Efficient selection of high-producing subclones during gene amplification of recombinant Chinese hamster ovary cells by flow cytometry and cell sorting. Biotechnol Bioeng. 2000-2001; 71(4): 266-73; Carroll, S.; Al-Rubeai, M. The selection of high-producing cell lines using flow cytometry and cell sorting. Expert Opin. Biol. Ther. 2004, 4, 1821-1829; Yoshikawa, T.; Nakanishi, F.; Ogura, Y.; Oi, D.; Omasa, T.; Katakura, Y.; Kishimoto, M.; Suga, K. Flow cytometry: An improved method for the selection of highly productive geneamplified CHO cells using flow cytometry. Biotechnol. Bioeng. 2001, 74, 435-442; Meng, Y. G.; Liang, J.; Wong, W. L.; Chisholm, V. Green fluorescent protein as a second selectable marker for selection of high producing clones from transfected CHO cells. Gene 2000, 242, 201-207). In this specific case the cells were stained with Cy5 labeled hIGF-1Ea 3mut and the lowest 5% stained cells were sorted. These clones showed a dramatic reduction in the expression of IGF-1R and increased viable cell number during co-cultivation with hIGF-1Ea 3mut compared to the parental cell line (see FIGS. 5 and 6). Nevertheless cell growth inhibition was still present (direct comparison of clones cultivated with and without presence of hIGF-1Ea 3mut). As there are still low quantities of IGF-1R mRNA present (detected by real-time RT-PCR) it can be assumed that IGF-1R is still expressed to lower amount on the cell surface which explains the remaining sensitivity to IGF-1.

In the next step a knockout of IGF-1R using zinc finger nuclease technique (ZFN) was performed in CHO-K1 derivative cell and CHO-DUXB11 derived cell lines. ZFN which are specific binding in the region of exon 3 of IGF-1R were designed. Two plasmids, each of them encoding for one subunit of the IGF-1R specific ZFN, were co-transfected in CHO-K1 derivative cell or CHO-DUXB11 derived cells. Each ZFN subunit binds specific 18 base pair long sequences; therefore overall a 36 bp sequence is specifically recognized (avoiding random cutting on other locations of the genome). The endonuclease domain of FokI is reengineered to function only as heterodimer in order to cleave DNA. The ZFN dimer creates targeted double strand breaks at exon 3 of IGF-1R. Through the error prone cellular process of non-homologous end joining, this double strand break can result in modification of the DNA sequence and therefor creates a functional knockout of the targeted gene. For CHO-K1 derivative cell three knock out clones were generated (knock out on both alleles): Clone 1: Δ2 (SEQ ID NO.: 38), clone 2: Δ5 (SEQ ID NO.: 39) and clone 3: Δ2 (SEQ ID NO.: 40), Clone 1: +18 (and 14 bps substitution) (SEQ ID NO.: 42), clone 2: Δ22 (SEQ ID NO.: 41) and clone 3: Δ114 (SEQ ID NO.: 43).

CHO-DUXB11 derived cell line is in contrast to CHO-K1 derivative cell polyclonal and polyploidy which made the knockout of the IGF-1R challenging (more than 2 IGF-1R copies/genome had to be knocked out). We have generated several unique knockout clones with frame shift mutations and validated two of them with TOPO cloning and sequencing. Clone 12: Δ7 (50%) (SEQ ID NO.: 45)/Δ22 (50%) (SEQ ID NO.: 44), clone 19: Δ7 (14.5%)/Δ16 (44%)/Δ22 (18%)/Δ22mut (15%). The percentages in brackets are based on the frequency how often this mutation is occurring out of 32 sequenced bacterial colonies. For clone 19 it can be assumed that 6 IGF-1R alleles are existent (3×Δ16, 1×Δ7, 1×Δ22, 1×Δ22mut).

Figure 7:
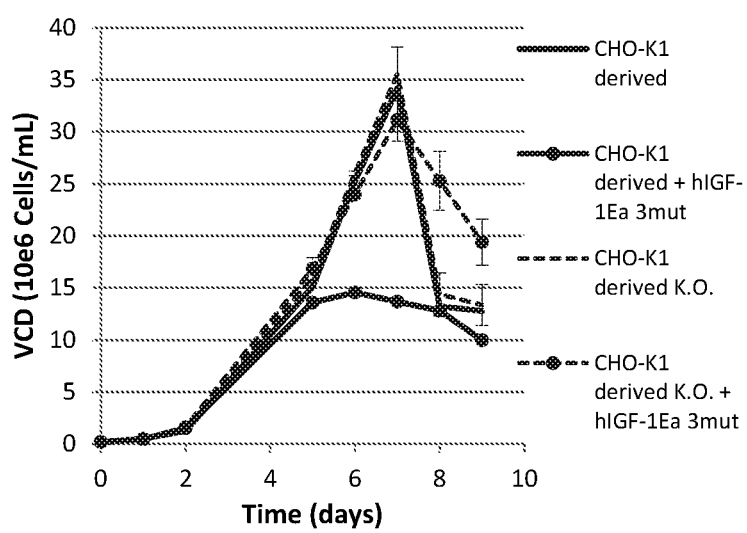
FIG. 7: In bold the viable cell density (VCD) of parental CHO-K1 derivative cells and in bold with circles the reduced cell growth during co-cultivation with hIGF-1Ea 3mut is shown. With dashed lines the cell growth average of the three IGF-1R KO clones are shown (error bars: standard error of the mean). The cell growth is slightly improved compared to the wildtype parental CHO-K1 derivative cells. The co-cultivation with hIGF-1Ea 3mut resulted in only minor cell growth inhibition and cell growth is similar to parental CHO-K1 derivative cell without hIGF-1 Ea 3mut co-cultivation.

The three generated CHO-K1 derivative cell IGF-1R KO clones were co-cultivated with hIGF-1Ea 3mut and no cell growth inhibition could be detected (see FIG. 7). The two generated IGF-1R KO CHO-DUXB11 derived clones were also cultivated in the presence/absence of IGF-1. Similar as CHO-K1 IGF-1R KO clones an improved cell growth could be detected for the KO clones in comparison to the wild-type CHO-DUXB11 derived cells (see FIG. 8). One of the KO clones showed no cell growth inhibition in the presence of IGF-1 and the other KO clone had in the presence of IGF-1 a similar maximum viable cell count as the CHO-DUXB11 derived cell without IGF-1 co-cultivation.

The Δ5/Δ22 CHO-K1 derivative cell IGF-1R KO clone as well as the 47/422 CHO-DUXB11 cell derived IGF-1R KO clone were transfected with 5 different IGF-1-FC fusion candidates (see FIG. 9). A 5-17 fold titer increase of recombinant IGF-1-FC protein could be detected on pool level compared to the wild type CHO-K1 derivative cell/CHO-DUXB11 cell derived cell line transfected with a different IGF-1-FC fusion candidate.

Two of the IGF-1-FC fusion candidates (hIGF1-Ea-fc-_mut 13/2_A and hIGF1-Ea-fc_mut 04/2_E) expressed in CHO-K1 derivative cell IGF-1R-KO or CHO-DUXB11 derived IGF-1R-KO cell lines was cultivated in 100 L wave bioreactor (fedbatch process and temperature shift). CHO-K1 derivative cell IGF-1RKO pools expressing hIGF1-Ea-fc_mut 13/2_A/4 are growing up to a max. viable cell density of $3 \times 10^7$ cells/ml, which is higher than an average AB process (average cell density is $2.2 \times 10^7$ cells/ml. In comparison to the CHO-K1 derived wildtype cells expressing IGF-1 this is a 3-6 fold increase in viable cell numbers (see FIG. 1). CHO-DUXB11 derived IGF-1RKO cells expressing hIGF1-Ea-fc_mut 13/2_A/4 were growing up to a max. cell density of 1.5-2×10⁷ cells/ml which is higher max. cell density compared to the wildtype CHO-DUXB11 derived cell line.

The CHO-DUXB11 derived IGF-1R KO cells expressing hIGF1-Ea-fc_mut 13/2_A were single cell sorted and batch titer in 24 well as well as in 50 ml batch cultures determined. in FIG. 9 the shake flask titer of the 15 best clones from each group. Overall the CHO-DUXB11 cell derived IGF-1R KO clones have an 8 fold higher 24 well titer and a 7 fold higher shake flask titer.

The invention claimed is:

1. A method of producing a protein in a mammalian cell, wherein the cell has been modified to be deficient in expression of a cognate receptor of the protein and has been transformed with a nucleic acid encoding the protein, the method comprising the steps of:
   (a) Cultivating the cell under conditions allowing the expression of the protein; and
   (b) Harvesting the protein from the cell cultivated in step (a),
wherein the cell produces at least 1.5-fold more protein than a cell in which the expression of the receptor has not been modified, wherein the protein is Insulin like growth factor 1 (IGF-1) protein or a variant thereof and the receptor is IGF-1 receptor (IGF-1R).

2. The method of claim 1, wherein the deficiency in the expression of the receptor in the cell has been achieved by applying RNA interference or targeted genetic recombination.

3. The method of claim 2, wherein the deficiency in the expression of the receptor in the cell has been achieved by applying RNA interference, the method comprising the steps of:

(c) introducing into the cell a double-stranded ribonucleic acid (dsRNA), wherein the dsRNA comprises a sense and an antisense strand, and wherein the sense strand comprises a first sequence, and the antisense strand comprises a second sequence comprising a region of complementarity which is substantially complementary to at least a part of the mRNA encoding the receptor, and wherein the region of complementarity is less than 30 nucleotides in length and wherein introduction of the dsRNA into the cell can inhibit expression of the gene encoding the receptor by at least 10%; and (d) maintaining the cell produced in step (c) for a time sufficient to obtain degradation of the mRNA transcript of the gene encoding the receptor, thereby inhibiting expression of the receptor gene in the cell, wherein the steps (c) and (d) are both performed before the steps (a) and (b).

4. The method of claim 2, wherein the RNA interference is achieved using a shRNA, the method comprising the steps of:

(c) introducing into the cell a shRNA which is substantially complementary to at least a part of the mRNA encoding the receptor, and wherein introduction of the shRNA into the cell can inhibit expression of the receptor gene by at least 10%; and (d) maintaining the cell produced in step (a) for a time sufficient to obtain degradation of the mRNA transcript of the receptor gene, wherein the steps (c) and (d) are both performed before the steps (a) and (b).

5. The method of claim 1, wherein the cell which has been modified to be deficient in expression of IGF-1R is a CHO, COS, Vero, Hela, BHK, HEK, NS0, C127, hybridoma, PerC6, CAP, or Sp-2/0 cell.

6. The method of claim 5, wherein the cell is a CHO-K1 derivative cell, a CHO-DUXB11 derivative cell, or a CHO-DG44 cell.

7. The method of claim 6, wherein the cell has been modified using a shRNA in RNA interference, and wherein the sequence of the shRNA is selected from the group consisting of SEQ ID NO: 5, 6, 7, 8, 9 and 10.

8. The method of claim 3, wherein the cognate receptor is IGF-1R of SEQ ID NO: 44, and the sequence of a strand of the dsRNA is SEQ ID NO: 1 or 3.

9. The method of claim 1, wherein the deficiency in the expression of the IGF-1R has been achieved by the use of a zinc finger nuclease.

10. The method of claim 1, wherein the growth factor is the human Insulin like growth factor 1 (IGF-1) protein of SEQ ID NO: 16 or a variant thereof.

11. The method of claim 1, further comprising the steps of
c. Making the cell deficient in the expression of Insulin growth factor 1 receptor;
d. Transforming the cell with an expression vector comprising a nucleic acid encoding an IGF-1 or a variant thereof;
e. Selecting cell of step (d) being transformed;
wherein steps (c) and (d) can be performed in either order, and wherein steps (c), (d) and (e) are performed before steps (a) and (b).

12. The method of claim 1, wherein the protein is produced at an industrial manufacturing scale.

13. The method of claim 1, wherein the growth factor is a human insulin like growth factor 1 (IGF-1) protein variant selected from the group consisting of SEQ ID NO: 23, 24, 25, 26, 27, 28 and 29.

* * * * *

```
                         SEQUENCE LISTING

<160> NUMBER OF SEQ ID NOS: 49

<210> SEQ ID NO 1
  <211> LENGTH: 21
  <212> TYPE: DNA
  <213> ORGANISM: Artificial Sequence
  <220> FEATURE:
  <223> OTHER INFORMATION: SiRNA sequence against the Chinese Hamster
        IGF1Receptor gene

<400> SEQUENCE: 1
cagucaaaau uggagauuut t                                             21

<210> SEQ ID NO 2
  <211> LENGTH: 21
  <212> TYPE: DNA
  <213> ORGANISM: Artificial Sequence
  <220> FEATURE:
  <223> OTHER INFORMATION: SiRNA sequence against the Chinese Hamster
        IGF1Receptor gene

<400> SEQUENCE: 2
aaaucuccaa uuuugacugt g                                             21

<210> SEQ ID NO 3
  <211> LENGTH: 21
  <212> TYPE: DNA
  <213> ORGANISM: Artificial Sequence
  <220> FEATURE:
  <223> OTHER INFORMATION: SiRNA sequence against the Chinese Hamster
        IGF1Receptor gene

<400> SEQUENCE: 3
ccacaugggu uaaguuaaat t                                             21

<210> SEQ ID NO 4
  <211> LENGTH: 21
  <212> TYPE: DNA
  <213> ORGANISM: Artificial Sequence
  <220> FEATURE:
  <223> OTHER INFORMATION: SiRNA sequence against the Chinese Hamster
        IGF1Receptor gene

<400> SEQUENCE: 4
uuuaacuuaa cccauguggt a                                             21

<210> SEQ ID NO 5
  <211> LENGTH: 66
  <212> TYPE: DNA
  <213> ORGANISM: Artificial Sequence
  <220> FEATURE:
  <223> OTHER INFORMATION: DNA encoding a shRNA against the Chinese
        Hamster IGF1Receptor gene

<400> SEQUENCE: 5
agcttttcca aaaatacca catgggttaa gttaaatctc ttgaatttaa cttaacccat    60
gtggcg                                                             66

<210> SEQ ID NO 6
  <211> LENGTH: 65
```

```
<212> TYPE: DNA
<213> ORGANISM: Artificial Sequence
<220> FEATURE:
<223> OTHER INFORMATION: DNA encoding a shRNA against the Chinese
      Hamster IGF1Receptor gene

<400> SEQUENCE: 6
agcttttcca aaaacagca tcaaggatga gatggatctc ttgagtccat ctcatccttg    60
atgcg                                                              65

<210> SEQ ID NO 7
<211> LENGTH: 65
<212> TYPE: DNA
<213> ORGANISM: Artificial Sequence
<220> FEATURE:
<223> OTHER INFORMATION: DNA encoding a ShRNA against the Chinese
      Hamster IGF1Receptor gene

<400> SEQUENCE: 7
agcttttcca aaaactgca tggtagctga agattttctc ttgagaaaatc ttcagctacc   60 atgcg                                                              65

<210> SEQ ID NO 8
<211> LENGTH: 65
<212> TYPE: DNA
<213> ORGANISM: Artificial Sequence
<220> FEATURE:
<223> OTHER INFORMATION: DNA encoding a shRNA against the Chinese
      Hamster IGF1Receptor gene

<400> SEQUENCE: 8
agcttttcca aaaactggt ttacaagaac taattatctc ttgagtaatt agttcttgta    60
aaccg                                                              65

<210> SEQ ID NO 9
<211> LENGTH: 66
<212> TYPE: DNA
<213> ORGANISM: Artificial Sequence
<220> FEATURE:
<223> OTHER INFORMATION: DNA encoding a shRNA against the Chinese
      Hamster IGF1Receptor gene

<400> SEQUENCE: 9
agcttttcca aaaataccc tttctttgag agcagatctc ttgagtctgc tctcaaagaa    60
agggcg                                                             66

<210> SEQ ID NO 10
<211> LENGTH: 65
<212> TYPE: DNA
<213> ORGANISM: Artificial Sequence
<220> FEATURE:
<223> OTHER INFORMATION: DNA encoding a shRNA against the Chinese
      Hamster IGF1Receptor gene

<400> SEQUENCE: 10
agcttttcca aaaacggca caactactgc tccaaatctc ttgaatttgg agcagtagtt    60
gtgcg                                                              65

<210> SEQ ID NO 11
<211> LENGTH: 41
<212> TYPE: DNA
<213> ORGANISM: Chinese Hamster

<400> SEQUENCE: 11
```

```
cccacctggc acctacaggt tcgagggctg gcgctgtgtg g                   41
```

<210> SEQ ID NO 12
<211> LENGTH: 20
<212> TYPE: DNA
<213> ORGANISM: Chinese Hamster

<400> SEQUENCE: 12

```
ctagcctgtc tctgggacac                                          20
```

<210> SEQ ID NO 13
<211> LENGTH: 20
<212> TYPE: DNA
<213> ORGANISM: Chinese Hamster

<400> SEQUENCE: 13

```
ctggatgaac ctctgggtgg                                          20
```

<210> SEQ ID NO 14
<211> LENGTH: 313
<212> TYPE: DNA
<213> ORGANISM: Chinese Hamster

<400> SEQUENCE: 14

```
tgtgcccaag tgtgtgcgga aagcgagcgt gcaccgagaa caacgaatgc tgccacccag    60
agtgcctagg cagctgccat acacctgacg acaacacaac ctgtgtggcc tgccgacact   120
actactacaa aggcgtgtgt gtgcctgcct gcccacctgg cacctacagg ttcgagggct   180
ggcgctgtgt ggaccgcgat ttctgcgcca acatccccaa cgctgagagc agtgactcag   240
atggctttgt catccacgat ggcgagtgca tgcaagaatg ccctcaggc ttcatccgca    300
acagcaccca gag                                                     313
```

<210> SEQ ID NO 15
<211> LENGTH: 774
<212> TYPE: DNA
<213> ORGANISM: Chinese Hamster

<400> SEQUENCE: 15

```
aaacttaacg gcacatccca tagcaaacca tttcataaga aaggacttgg catgtgttgt    60
gtcctttccc agtgtgggct tcacagatgg tattacctgt gcagatttca gagaaagtgt   120
gttttttccta gcctgtctct gggacaccat ttagtgctgg ttgtggcagc agatgaccct   180
gggaggctg tgtagtctct tcatctcacc acctcctccc cctgttccca cagtgtgccc    240
aagtgtgtgc ggaaagcgag cgtgcaccga gaacaacgaa tgctgccacc cagagtgcct   300
aggcagctgc catacacctg acgacaacac aacctgtgtg gcctgccgac actactacta   360
caaaggcgtg tgtgtgcctg cctgcccacc tggcacctac aggttcgagg ctggcgctg    420
tgtggaccgc gatttctgcg ccaacatccc caacgctgag agcagtgact cagatggctt   480
tgtcatccac gatggcgagt gcatgcaaga atgtccctca ggcttcatcc gcaacagcac   540
ccagaggtca gtggctcttg ttccccatcc aggaggtgaa tcttgttcat attccatgat   600
tgtaggaacc acccagaggt tcatccagat ggggaggctg ttgagggtg ctgactaagc    660
ttgtttttat gagaatcttg gaatggctgg tctgttcatt tctttgtttg ttggcttgct   720
ttgttgtctt tgaaagtgcc ttgctagccc tagagaggaa gaattagcct gctg         774
```

<210> SEQ ID NO 16

```
<211> LENGTH: 70
<212> TYPE: PRT
<213> ORGANISM: Homo sapiens

<400> SEQUENCE: 16

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
    50                  55                  60

Lys Pro Ala Lys Ser Ala
65                  70

<210> SEQ ID NO 17
<211> LENGTH: 35
<212> TYPE: PRT
<213> ORGANISM: Homo sapiens

<400> SEQUENCE: 17

Arg Ser Val Arg Ala Gln Arg His Thr Asp Met Pro Lys Thr Gln Lys
1               5                   10                  15

Glu Val His Leu Lys Asn Ala Ser Arg Gly Ser Ala Gly Asn Lys Asn
                20                  25                  30

Tyr Arg Met
        35

<210> SEQ ID NO 18
<211> LENGTH: 77
<212> TYPE: PRT
<213> ORGANISM: Human

<400> SEQUENCE: 18

Arg Ser Val Arg Ala Gln Arg His Thr Asp Met Pro Lys Thr Gln Lys
1               5                   10                  15

Tyr Gln Pro Pro Ser Thr Asn Lys Asn Thr Lys Ser Gln Arg Arg Lys
                20                  25                  30

Gly Trp Pro Lys Thr His Pro Gly Gly Glu Gln Lys Glu Gly Thr Glu
            35                  40                  45

Ala Ser Leu Gln Ile Arg Gly Lys Lys Lys Glu Gln Arg Arg Glu Ile
    50                  55                  60

Gly Ser Arg Asn Ala Glu Cys Arg Gly Lys Lys Gly Lys
65                  70                  75

<210> SEQ ID NO 19
<211> LENGTH: 40
<212> TYPE: PRT
<213> ORGANISM: Homo sapiens

<400> SEQUENCE: 19

Arg Ser Val Arg Ala Gln Arg His Thr Asp Met Pro Lys Thr Gln Lys
1               5                   10                  15

Tyr Gln Pro Pro Ser Thr Asn Lys Asn Thr Lys Ser Gln Arg Arg Lys
                20                  25                  30

Gly Ser Thr Phe Glu Glu Arg Lys
            35                  40
```

<210> SEQ ID NO 20
<211> LENGTH: 105
<212> TYPE: PRT
<213> ORGANISM: Homo sapiens

<400> SEQUENCE: 20

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala Arg Ser Val Arg Ala Gln Arg His Thr Asp
65                  70                  75                  80

Met Pro Lys Thr Gln Lys Glu Val His Leu Lys Asn Ala Ser Arg Gly
                85                  90                  95

Ser Ala Gly Asn Lys Asn Tyr Arg Met
                100                 105

<210> SEQ ID NO 21
<211> LENGTH: 328
<212> TYPE: PRT
<213> ORGANISM: Artificial Sequence
<220> FEATURE:
<223> OTHER INFORMATION: Mutated Human IGF-1 protein

<400> SEQUENCE: 21

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Arg Ala Ala Pro Gln Thr Gly Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Lys Ser Ala Val Arg Ala Gln His Thr Asp Met Pro Lys Thr Gln Lys
65                  70                  75                  80

Glu Val His Leu Lys Asn Ala Ser Arg Gly Ser Ala Gly Asn Lys Asn
                85                  90                  95

Tyr Arg Met Gly Ser Asp Lys Thr His Thr Cys Pro Pro Cys Pro Ala
            100                 105                 110

Pro Glu Ala Ala Gly Gly Pro Ser Val Phe Leu Phe Pro Pro Lys Pro
        115                 120                 125

Lys Asp Thr Leu Met Ile Ser Arg Thr Pro Glu Val Thr Cys Val Val
    130                 135                 140

Val Asp Val Ser His Glu Asp Pro Glu Val Lys Phe Asn Trp Tyr Val
145                 150                 155                 160

Asp Gly Val Glu Val His Asn Ala Lys Thr Lys Pro Arg Glu Glu Gln
                165                 170                 175

Tyr Asn Ser Thr Tyr Arg Val Val Ser Val Leu Thr Val Leu His Gln
            180                 185                 190

Asp Trp Leu Asn Gly Lys Glu Tyr Lys Cys Lys Val Ser Asn Lys Ala
        195                 200                 205

Leu Pro Ala Pro Ile Glu Lys Thr Ile Ser Lys Ala Lys Gly Gln Pro
    210                 215                 220

```
Arg Glu Pro Gln Val Tyr Thr Leu Pro Pro Ser Arg Glu Glu Met Thr
225                 230                 235                 240

Lys Asn Gln Val Ser Leu Thr Cys Leu Val Lys Gly Phe Tyr Pro Ser
            245                 250                 255

Asp Ile Ala Val Glu Trp Glu Ser Asn Gly Gln Pro Glu Asn Asn Tyr
        260                 265                 270

Lys Thr Thr Pro Pro Val Leu Asp Ser Asp Gly Ser Phe Phe Leu Tyr
    275                 280                 285

Ser Lys Leu Thr Val Asp Lys Ser Arg Trp Gln Gln Gly Asn Val Phe
290                 295                 300

Ser Cys Ser Val Met His Glu Ala Leu His Asn His Tyr Thr Gln Lys
305                 310                 315                 320

Ser Leu Ser Leu Ser Pro Gly Lys
                325

<210> SEQ ID NO 22
<211> LENGTH: 329
<212> TYPE: PRT
<213> ORGANISM: Artificial Sequence
<220> FEATURE:
<223> OTHER INFORMATION: Mutated Human IGF-1 protein

<400> SEQUENCE: 22

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Arg Ala Ala Pro Gln Thr Gly Ile Val Asp Glu Cys Cys Phe Arg Ser
        35                  40                  45

Cys Asp Leu Arg Arg Leu Glu Met Tyr Cys Ala Pro Leu Lys Pro Ala
50                  55                  60

Lys Ser Ala Val Arg Ala Gln Gln His Thr Asp Met Pro Lys Thr Gln
65                  70                  75                  80

Lys Glu Val His Leu Lys Asn Ala Ser Arg Gly Ser Ala Gly Asn Lys
                85                  90                  95

Asn Tyr Arg Met Gly Ser Asp Lys Thr His Thr Cys Pro Pro Cys Pro
            100                 105                 110

Ala Pro Glu Ala Ala Gly Gly Pro Ser Val Phe Leu Phe Pro Pro Lys
        115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255
```

```
Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 23
<211> LENGTH: 324
<212> TYPE: PRT
<213> ORGANISM: Artificial Sequence
<220> FEATURE:
<223> OTHER INFORMATION: Mutated human IGF-1 protein

<400> SEQUENCE: 23

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Gln Ala Ala Pro Gln Thr Ser Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Val Gln Ala Gln Gln His Thr Asp Met Pro Lys Thr Gln Lys Glu Val
65                  70                  75                  80

His Leu Lys Asn Ala Ser Arg Gly Ser Ala Gly Asn Lys Asn Tyr Gln
                85                  90                  95

Met Asp Lys Thr His Thr Cys Pro Pro Cys Pro Ala Pro Glu Ala Ala
            100                 105                 110

Gly Gly Pro Ser Val Phe Leu Phe Pro Pro Lys Pro Lys Asp Thr Leu
        115                 120                 125

Met Ile Ser Arg Thr Pro Glu Val Thr Cys Val Val Val Asp Val Ser
    130                 135                 140

His Glu Asp Pro Glu Val Lys Phe Asn Trp Tyr Val Asp Gly Val Glu
145                 150                 155                 160

Val His Asn Ala Lys Thr Lys Pro Arg Glu Glu Gln Tyr Asn Ser Thr
                165                 170                 175

Tyr Arg Val Val Ser Val Leu Thr Val Leu His Gln Asp Trp Leu Asn
            180                 185                 190

Gly Lys Glu Tyr Lys Cys Lys Val Ser Asn Lys Ala Leu Pro Ala Pro
        195                 200                 205

Ile Glu Lys Thr Ile Ser Lys Ala Lys Gly Gln Pro Arg Glu Pro Gln
    210                 215                 220

Val Tyr Thr Leu Pro Pro Ser Arg Glu Glu Met Thr Lys Asn Gln Val
225                 230                 235                 240

Ser Leu Thr Cys Leu Val Lys Gly Phe Tyr Pro Ser Asp Ile Ala Val
                245                 250                 255

Glu Trp Glu Ser Asn Gly Gln Pro Glu Asn Asn Tyr Lys Thr Thr Pro
            260                 265                 270

Pro Val Leu Asp Ser Asp Gly Ser Phe Phe Leu Tyr Ser Lys Leu Thr
        275                 280                 285
```

-continued

```
Val Asp Lys Ser Arg Trp Gln Gln Gly Asn Val Phe Ser Cys Ser Val
    290                 295                 300

Met His Glu Ala Leu His Asn His Tyr Thr Gln Lys Ser Leu Ser Leu
305                 310                 315                 320

Ser Pro Gly Lys

<210> SEQ ID NO 24
<211> LENGTH: 319
<212> TYPE: PRT
<213> ORGANISM: Artificial Sequence
<220> FEATURE:
<223> OTHER INFORMATION: Mutated human IGF-1 protein

<400> SEQUENCE: 24

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
                20                  25                  30

Gln Ala Ala Pro Gln Thr Ser Ile Val Asp Glu Cys Cys Phe Arg Ser
            35                  40                  45

Cys Asp Leu Arg Arg Leu Glu Met Tyr Cys Ala Pro Leu Lys Pro Ala
50                  55                  60

Val Gln Ala Gln Gln His Thr Asp Met Pro Lys Thr Gln Lys Glu Val
65                  70                  75                  80

His Leu Lys Asn Ala Ser Arg Gly Ser Ala Gly Asn Lys Asn Tyr Gln
                85                  90                  95

Met Cys Pro Pro Cys Pro Ala Pro Glu Ala Ala Gly Gly Pro Ser Val
            100                 105                 110

Phe Leu Phe Pro Pro Lys Pro Lys Asp Thr Leu Met Ile Ser Arg Thr
        115                 120                 125

Pro Glu Val Thr Cys Val Val Val Asp Val Ser His Glu Asp Pro Glu
    130                 135                 140

Val Lys Phe Asn Trp Tyr Val Asp Gly Val Glu Val His Asn Ala Lys
145                 150                 155                 160

Thr Lys Pro Arg Glu Glu Gln Tyr Asn Ser Thr Tyr Arg Val Val Ser
                165                 170                 175

Val Leu Thr Val Leu His Gln Asp Trp Leu Asn Gly Lys Glu Tyr Lys
            180                 185                 190

Cys Lys Val Ser Asn Lys Ala Leu Pro Ala Pro Ile Glu Lys Thr Ile
        195                 200                 205

Ser Lys Ala Lys Gly Gln Pro Arg Glu Pro Gln Val Tyr Thr Leu Pro
    210                 215                 220

Pro Ser Arg Glu Glu Met Thr Lys Asn Gln Val Ser Leu Thr Cys Leu
225                 230                 235                 240

Val Lys Gly Phe Tyr Pro Ser Asp Ile Ala Val Glu Trp Glu Ser Asn
                245                 250                 255

Gly Gln Pro Glu Asn Asn Tyr Lys Thr Thr Pro Pro Val Leu Asp Ser
            260                 265                 270

Asp Gly Ser Phe Phe Leu Tyr Ser Lys Leu Thr Val Asp Lys Ser Arg
        275                 280                 285

Trp Gln Gln Gly Asn Val Phe Ser Cys Ser Val Met His Glu Ala Leu
    290                 295                 300

His Asn His Tyr Thr Gln Lys Ser Leu Ser Leu Ser Pro Gly Lys
305                 310                 315
```

<210> SEQ ID NO 25
<211> LENGTH: 309
<212> TYPE: PRT
<213> ORGANISM: Artificial Sequence
<220> FEATURE:
<223> OTHER INFORMATION: Mutated human IGF-1 protein

<400> SEQUENCE: 25

```
Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
                20                  25                  30

Gln Ala Ala Pro Gln Thr Ser Ile Val Asp Glu Cys Cys Phe Arg Ser
            35                  40                  45

Cys Asp Leu Arg Arg Leu Glu Met Tyr Cys Ala Pro Leu Lys Pro Ala
    50                  55                  60

Val Gln Ala Gln Gln His Thr Asp Met Pro Lys Thr Gln Lys Glu Val
65                  70                  75                  80

His Leu Lys Asn Ala Ser Gly Cys Pro Pro Cys Pro Ala Pro Glu Ala
                85                  90                  95

Ala Gly Gly Pro Ser Val Phe Leu Phe Pro Pro Lys Pro Lys Asp Thr
            100                 105                 110

Leu Met Ile Ser Arg Thr Pro Glu Val Thr Cys Val Val Val Asp Val
    115                 120                 125

Ser His Glu Asp Pro Glu Val Lys Phe Asn Trp Tyr Val Asp Gly Val
130                 135                 140

Glu Val His Asn Ala Lys Thr Lys Pro Arg Glu Glu Gln Tyr Asn Ser
145                 150                 155                 160

Thr Tyr Arg Val Val Ser Val Leu Thr Val Leu His Gln Asp Trp Leu
                165                 170                 175

Asn Gly Lys Glu Tyr Lys Cys Lys Val Ser Asn Lys Ala Leu Pro Ala
            180                 185                 190

Pro Ile Glu Lys Thr Ile Ser Lys Ala Lys Gly Gln Pro Arg Glu Pro
    195                 200                 205

Gln Val Tyr Thr Leu Pro Pro Ser Arg Glu Glu Met Thr Lys Asn Gln
210                 215                 220

Val Ser Leu Thr Cys Leu Val Lys Gly Phe Tyr Pro Ser Asp Ile Ala
225                 230                 235                 240

Val Glu Trp Glu Ser Asn Gly Gln Pro Glu Asn Asn Tyr Lys Thr Thr
                245                 250                 255

Pro Pro Val Leu Asp Ser Asp Gly Ser Phe Phe Leu Tyr Ser Lys Leu
            260                 265                 270

Thr Val Asp Lys Ser Arg Trp Gln Gln Gly Asn Val Phe Ser Cys Ser
    275                 280                 285

Val Met His Glu Ala Leu His Asn His Tyr Thr Gln Lys Ser Leu Ser
290                 295                 300

Leu Ser Pro Gly Lys
305
```

<210> SEQ ID NO 26
<211> LENGTH: 314
<212> TYPE: PRT
<213> ORGANISM: Artificial Sequence
<220> FEATURE:
<223> OTHER INFORMATION: Mutated human IGF-1 protein

<400> SEQUENCE: 26

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Gln Ala Ala Pro Gln Thr Ser Ile Val Asp Glu Cys Cys Phe Arg Ser
            35                  40                  45

Cys Asp Leu Arg Arg Leu Glu Met Tyr Cys Ala Pro Leu Lys Pro Ala
50                  55                  60

Val Gln Ala Gln Gln His Thr Asp Met Pro Lys Thr Gln Lys Glu Val
65                  70                  75                  80

His Leu Lys Asn Ala Ser Gly Asp Lys Thr His Thr Cys Pro Pro Cys
                85                  90                  95

Pro Ala Pro Glu Ala Ala Gly Gly Pro Ser Val Phe Leu Phe Pro Pro
                100                 105                 110

Lys Pro Lys Asp Thr Leu Met Ile Ser Arg Thr Pro Glu Val Thr Cys
            115                 120                 125

Val Val Val Asp Val Ser His Glu Asp Pro Glu Val Lys Phe Asn Trp
        130                 135                 140

Tyr Val Asp Gly Val Glu Val His Asn Ala Lys Thr Lys Pro Arg Glu
145                 150                 155                 160

Glu Gln Tyr Asn Ser Thr Tyr Arg Val Val Ser Val Leu Thr Val Leu
                165                 170                 175

His Gln Asp Trp Leu Asn Gly Lys Glu Tyr Lys Cys Lys Val Ser Asn
            180                 185                 190

Lys Ala Leu Pro Ala Pro Ile Glu Lys Thr Ile Ser Lys Ala Lys Gly
            195                 200                 205

Gln Pro Arg Glu Pro Gln Val Tyr Thr Leu Pro Pro Ser Arg Glu Glu
        210                 215                 220

Met Thr Lys Asn Gln Val Ser Leu Thr Cys Leu Val Lys Gly Phe Tyr
225                 230                 235                 240

Pro Ser Asp Ile Ala Val Glu Trp Glu Ser Asn Gly Gln Pro Glu Asn
                245                 250                 255

Asn Tyr Lys Thr Thr Pro Pro Val Leu Asp Ser Asp Gly Ser Phe Phe
            260                 265                 270

Leu Tyr Ser Lys Leu Thr Val Asp Lys Ser Arg Trp Gln Gln Gly Asn
        275                 280                 285

Val Phe Ser Cys Ser Val Met His Glu Ala Leu His Asn His Tyr Thr
290                 295                 300

Gln Lys Ser Leu Ser Leu Ser Pro Gly Lys
305                 310

<210> SEQ ID NO 27
<211> LENGTH: 324
<212> TYPE: PRT
<213> ORGANISM: Artificial Sequence
<220> FEATURE:
<223> OTHER INFORMATION: Mutated human IGF-1 protein

<400> SEQUENCE: 27

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Arg Glu Ala Pro Gln Thr Ser Ile Val Asp Glu Cys Cys Phe Arg Ser
            35                  40                  45

```
Cys Asp Leu Arg Arg Leu Glu Met Tyr Cys Ala Pro Leu Lys Pro Ala
 50                  55                  60

Val Gln Ala Gln Gln His Thr Asp Met Pro Lys Thr Gln Lys Glu Val
 65                  70                  75                  80

His Leu Lys Asn Ala Ser Arg Gly Ser Ala Gly Asn Lys Asn Tyr Gln
                 85                  90                  95

Met Asp Lys Thr His Thr Cys Pro Pro Cys Pro Ala Pro Glu Ala Ala
             100                 105                 110

Gly Gly Pro Ser Val Phe Leu Phe Pro Pro Lys Pro Lys Asp Thr Leu
         115                 120                 125

Met Ile Ser Arg Thr Pro Glu Val Thr Cys Val Val Val Asp Val Ser
130                 135                 140

His Glu Asp Pro Glu Val Lys Phe Asn Trp Tyr Val Asp Gly Val Glu
145                 150                 155                 160

Val His Asn Ala Lys Thr Lys Pro Arg Glu Glu Gln Tyr Asn Ser Thr
                165                 170                 175

Tyr Arg Val Val Ser Val Leu Thr Val Leu His Gln Asp Trp Leu Asn
            180                 185                 190

Gly Lys Glu Tyr Lys Cys Lys Val Ser Asn Lys Ala Leu Pro Ala Pro
        195                 200                 205

Ile Glu Lys Thr Ile Ser Lys Ala Lys Gly Gln Pro Arg Glu Pro Gln
    210                 215                 220

Val Tyr Thr Leu Pro Pro Ser Arg Glu Glu Met Thr Lys Asn Gln Val
225                 230                 235                 240

Ser Leu Thr Cys Leu Val Lys Gly Phe Tyr Pro Ser Asp Ile Ala Val
                245                 250                 255

Glu Trp Glu Ser Asn Gly Gln Pro Glu Asn Asn Tyr Lys Thr Thr Pro
            260                 265                 270

Pro Val Leu Asp Ser Asp Gly Ser Phe Phe Leu Tyr Ser Lys Leu Thr
        275                 280                 285

Val Asp Lys Ser Arg Trp Gln Gln Gly Asn Val Phe Ser Cys Ser Val
    290                 295                 300

Met His Glu Ala Leu His Asn His Tyr Thr Gln Lys Ser Leu Ser Leu
305                 310                 315                 320

Ser Pro Gly Lys

<210> SEQ ID NO 28
<211> LENGTH: 319
<212> TYPE: PRT
<213> ORGANISM: Artificial Sequence
<220> FEATURE:
<223> OTHER INFORMATION: Mutated human IGF-1 protein

<400> SEQUENCE: 28

Thr Leu Cys Gly Ala Glu Leu Val Asp Ala Leu Gln Phe Val Cys Gly
 1                   5                  10                  15

Asp Arg Gly Phe Tyr Phe Asn Lys Pro Thr Gly Tyr Gly Ser Ser Ser
                 20                  25                  30

Arg Glu Ala Pro Gln Thr Ser Ile Val Asp Glu Cys Cys Phe Arg Ser
             35                  40                  45

Cys Asp Leu Arg Arg Leu Glu Met Tyr Cys Ala Pro Leu Lys Pro Ala
 50                  55                  60

Val Gln Ala Gln Gln His Thr Asp Met Pro Lys Thr Gln Lys Glu Val
 65                  70                  75                  80
```

His Leu Lys Asn Ala Ser Arg Gly Ser Ala Gly Asn Lys Asn Tyr Gln
                85                  90                  95

Met Cys Pro Pro Cys Pro Ala Pro Glu Ala Ala Gly Gly Pro Ser Val
            100                 105                 110

Phe Leu Phe Pro Pro Lys Pro Lys Asp Thr Leu Met Ile Ser Arg Thr
        115                 120                 125

Pro Glu Val Thr Cys Val Val Val Asp Val Ser His Glu Asp Pro Glu
130                 135                 140

Val Lys Phe Asn Trp Tyr Val Asp Gly Val Glu Val His Asn Ala Lys
145                 150                 155                 160

Thr Lys Pro Arg Glu Glu Gln Tyr Asn Ser Thr Tyr Arg Val Val Ser
                165                 170                 175

Val Leu Thr Val Leu His Gln Asp Trp Leu Asn Gly Lys Glu Tyr Lys
            180                 185                 190

Cys Lys Val Ser Asn Lys Ala Leu Pro Ala Pro Ile Glu Lys Thr Ile
        195                 200                 205

Ser Lys Ala Lys Gly Gln Pro Arg Glu Pro Gln Val Tyr Thr Leu Pro
    210                 215                 220

Pro Ser Arg Glu Glu Met Thr Lys Asn Gln Val Ser Leu Thr Cys Leu
225                 230                 235                 240

Val Lys Gly Phe Tyr Pro Ser Asp Ile Ala Val Glu Trp Glu Ser Asn
                245                 250                 255

Gly Gln Pro Glu Asn Asn Tyr Lys Thr Thr Pro Pro Val Leu Asp Ser
            260                 265                 270

Asp Gly Ser Phe Phe Leu Tyr Ser Lys Leu Thr Val Asp Lys Ser Arg
        275                 280                 285

Trp Gln Gln Gly Asn Val Phe Ser Cys Ser Val Met His Glu Ala Leu
    290                 295                 300

His Asn His Tyr Thr Gln Lys Ser Leu Ser Leu Ser Pro Gly Lys
305                 310                 315

<210> SEQ ID NO 29
<211> LENGTH: 314
<212> TYPE: PRT
<213> ORGANISM: Artificial Sequence
<220> FEATURE:
<223> OTHER INFORMATION: Mutated human IGF-1 protein

<400> SEQUENCE: 29

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Arg Glu Ala Pro Gln Thr Ser Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Val Gln Ala Gln Gln His Thr Asp Met Pro Lys Thr Gln Lys Glu Val
65                  70                  75                  80

His Leu Lys Asn Ala Ser Gly Asp Lys Thr His Thr Cys Pro Pro Cys
                85                  90                  95

Pro Ala Pro Glu Ala Ala Gly Gly Pro Ser Val Phe Leu Phe Pro Pro
            100                 105                 110

Lys Pro Lys Asp Thr Leu Met Ile Ser Arg Thr Pro Glu Val Thr Cys
        115                 120                 125

Val Val Val Asp Val Ser His Glu Asp Pro Glu Val Lys Phe Asn Trp
130                 135                 140

Tyr Val Asp Gly Val Glu Val His Asn Ala Lys Thr Lys Pro Arg Glu
145                 150                 155                 160

Glu Gln Tyr Asn Ser Thr Tyr Arg Val Val Ser Val Leu Thr Val Leu
                165                 170                 175

His Gln Asp Trp Leu Asn Gly Lys Glu Tyr Lys Cys Lys Val Ser Asn
            180                 185                 190

Lys Ala Leu Pro Ala Pro Ile Glu Lys Thr Ile Ser Lys Ala Lys Gly
        195                 200                 205

Gln Pro Arg Glu Pro Gln Val Tyr Thr Leu Pro Pro Ser Arg Glu Glu
    210                 215                 220

Met Thr Lys Asn Gln Val Ser Leu Thr Cys Leu Val Lys Gly Phe Tyr
225                 230                 235                 240

Pro Ser Asp Ile Ala Val Glu Trp Glu Ser Asn Gly Gln Pro Glu Asn
                245                 250                 255

Asn Tyr Lys Thr Thr Pro Pro Val Leu Asp Ser Asp Gly Ser Phe Phe
            260                 265                 270

Leu Tyr Ser Lys Leu Thr Val Asp Lys Ser Arg Trp Gln Gln Gly Asn
        275                 280                 285

Val Phe Ser Cys Ser Val Met His Glu Ala Leu His Asn His Tyr Thr
    290                 295                 300

Gln Lys Ser Leu Ser Leu Ser Pro Gly Lys
305                 310

<210> SEQ ID NO 30
<211> LENGTH: 6
<212> TYPE: PRT
<213> ORGANISM: Artificial Sequence
<220> FEATURE:
<223> OTHER INFORMATION: artificial peptide hinge region

<400> SEQUENCE: 30

Cys Pro Pro Cys Pro Ala
1               5

<210> SEQ ID NO 31
<211> LENGTH: 11
<212> TYPE: PRT
<213> ORGANISM: Artificial Sequence
<220> FEATURE:
<223> OTHER INFORMATION: artificial peptide hinge region

<400> SEQUENCE: 31

Asp Lys Thr His Thr Cys Pro Pro Cys Pro Ala
1               5                   10

<210> SEQ ID NO 32
<211> LENGTH: 16
<212> TYPE: PRT
<213> ORGANISM: Artificial Sequence
<220> FEATURE:
<223> OTHER INFORMATION: artificial peptide hinge region

<400> SEQUENCE: 32

Glu Pro Lys Ser Cys Asp Lys Thr His Thr Cys Pro Pro Cys Pro Ala
1               5                   10                  15

<210> SEQ ID NO 33
<211> LENGTH: 25
<212> TYPE: PRT

<213> ORGANISM: Artificial Sequence
<220> FEATURE:
<223> OTHER INFORMATION: Mutated human IGF-1 Ea peptide 1 - SEQ ID 33
      disclosed on page 49

<400> SEQUENCE: 33

Arg Ser Val Arg Ala Gln Arg His Thr Asp Met Pro Lys Thr Gln Lys
1               5                   10                  15

Glu Val His Leu Lys Asn Ala Ser Gly
            20                  25

<210> SEQ ID NO 34
<211> LENGTH: 34
<212> TYPE: PRT
<213> ORGANISM: Artificial Sequence
<220> FEATURE:
<223> OTHER INFORMATION: Mutated human IGF-1 Ea peptide 2 - SEQ ID 34
      disclosed on page 49

<400> SEQUENCE: 34

Arg Ser Val Arg Ala Gln Arg His Thr Asp Met Pro Lys Thr Gln Lys
1               5                   10                  15

Tyr Gln Pro Pro Ala Thr Asn Lys Asn Thr Lys Ser Gln Arg Arg Lys
            20                  25                  30

Gly Ser

<210> SEQ ID NO 35
<211> LENGTH: 102
<212> TYPE: PRT
<213> ORGANISM: Artificial Sequence
<220> FEATURE:
<223> OTHER INFORMATION: Mutated human IGF-1 protein

<400> SEQUENCE: 35

Gly Pro Thr Leu Cys Gly Ala Glu Leu Val Asp Ala Leu Gln Phe Val
1               5                   10                  15

Cys Gly Asp Arg Gly Phe Tyr Phe Asn Lys Pro Thr Gly Tyr Gly Ser
            20                  25                  30

Ser Ser Arg Ala Ala Pro Gln Thr Gly Ile Val Asp Glu Cys Cys Phe
        35                  40                  45

Arg Ser Cys Asp Leu Arg Arg Leu Glu Met Tyr Cys Ala Pro Leu Lys
    50                  55                  60

Pro Ala Lys Ser Ala Val Arg Ala Gln Arg His Thr Asp Met Pro Lys
65                  70                  75                  80

Thr Gln Lys Glu Val His Leu Lys Asn Ala Ser Arg Gly Ser Ala Gly
                85                  90                  95

Asn Lys Asn Tyr Arg Met
            100

<210> SEQ ID NO 36
<211> LENGTH: 4203
<212> TYPE: DNA
<213> ORGANISM: Artificial Sequence
<220> FEATURE:
<223> OTHER INFORMATION: plasmid

<400> SEQUENCE: 36
tcgcgatgta cgggccagat atacgcgttg acattgatta ttgactagtt attaatagta    60
atcaattacg gggtcattag ttcatagccc atatatggag ttccgcgtta cataacttac   120
ggtaaatggc ccgcctggct gaccgcccaa cgacccccgc ccattgacgt caataatgac   180

```
gtatgttccc atagtaacgc caatagggac tttccattga cgtcaatggg tggactattt       240
acggtaaact gcccacttgg cagtacatca agtgtatcat atgccaagta cgccccctat       300
tgacgtcaat gacggtaaat ggcccgcctg gcattatgcc cagtacatga ccttatggga       360
ctttcctact tggcagtaca tctacgtatt agtcatcgct attaccatgg tgatgcggtt       420
ttggcagtac atcaatgggc gtggatagcg gtttgactca cggggatttc caagtctcca       480
ccccattgac gtcaatggga gtttgttttg gcaccaaaat caacgggact ttccaaaatg       540
tcgtaacaac tccgccccat tgacgcaaat gggcggtagg cgtgtacggt gggaggtcta       600
tataagcaga gctctctggc taactagaga acccactgct tactggctta tcgaaattaa       660
tacgactcac tatagggaga cccaagctgg ctagcgttta acttaagct gatccactag        720 tccagtgtgg tggaattcgc catggactac aaagaccatg acggtgatta taaagatcat       780
gacatcgatt acaaggatga cgatgacaag atggccccca agaagaagag gaaggtgggc       840
atccacgggg tacccgccgc tatggctgag aggcccttcc agtgtcgaat ctgcatgcgt       900
aacttcagtc gctccgccca cctgtcccgc cacatccgca cccacaccgg cgagaagcct       960
tttgcctgtg acatttgtgg gaggaaattt gccacctccg gccacctgtc ccgccatacc      1020
aagatacaca cgggcagcca aaagcccttc cagtgtcgaa tctgcatgcg taacttcagt      1080
cagtccggcg acctgacccg ccacatccgc acccacaccg gcgagaagcc ttttgcctgt      1140
gacatttgtg gaggaaattt gcccgctcc tggggcctgc aggtgcatac caagatacac       1200
acgggatctc agaagccctt ccagtgtcga atctgcatgc gtaacttcag tcgctccgac      1260
aacctgtcca cccacatccg cacccacacc ggcgagaagc cttttgcctg tgacatttgt      1320
gggaggaaat ttgcccgctc cgacgcccgc gccaaccata ccaagataca cctgcgggga      1380
tcccagctgg tgaagagcga gctggaggag aagaagtccg agctgcggca caagctgaag      1440
tacgtgcccc acgagtacat cgagctgatc gagatcgcca ggaacagcac ccaggaccgc      1500
atcctggaga tgaaggtgat ggagttcttc atgaaggtgt acggctacag gggaaagcac      1560
ctgggcggaa gcagaaagcc tgacggcgcc atctatacag tgggcagccc catcgattac      1620
ggcgtgatcg tggacacaaa ggcctacagc ggcggctaca atctgcctat cggccaggcc      1680
gacgagatgg agagatacgt ggaggagaac cagacccgga ataagcacct caaccccaac      1740
gagtggtgga aggtgtaccc tagcagcgtg accgagttca gttcctgtt cgtgagcggc       1800 cacttcaagg gcaactacaa ggcccagctg accaggctga ccacatcac caactgcaat      1860 ggcgccgtgc tgagcgtgga ggagctgctg atcggcggcg agatgatcaa agccggcacc      1920
ctgacactgg aggaggtgcg gcgcaagttc aacaacggcg agatcaactt cagatcttga      1980
taactcgagt ctagagggcc cgtttaaacc cgctgatcag cctcgactgt gccttctagt      2040
tgccagccat ctgttgtttg ccctccccc gtgccttcct tgaccctgga aggtgccact       2100
cccactgtcc tttcctaata aaatgaggaa attgcatcgc attgtctgag taggtgtcat      2160
tctattctgg gggtggggt ggggcaggac agcaaggggg aggattggga agacaatagc       2220
aggcatgctg gggatgcggt gggctctatg gcttctactg gcggttttta tggacagcaa      2280
gcgaaccgga attgccagct ggggcgccct ctggtaaggt tgggaagccc tgcaaagtaa      2340
actggatggc tttctcgccg ccaaggatct gatggcgcag gggatcaagc tctgatcaag      2400
agacaggatg aggatcgttt cgcatgattg aacaagatgg attgcacgca ggttctccgg      2460
ccgcttgggt ggagaggcta ttcggctatg actgggcaca acagacaatc ggctgctctg      2520
atgccgccgt gttccggctg tcagcgcagg ggcgcccggt tctttttgtc aagaccgacc      2580
```

```
tgtccggtgc cctgaatgaa ctgcaagacg aggcagcgcg gctatcgtgg ctggccacga    2640
cgggcgttcc ttgcgcagct gtgctcgacg ttgtcactga agcgggaagg gactggctgc    2700
tattgggcga agtgccgggg caggatctcc tgtcatctca ccttgctcct gccgagaaag    2760
tatccatcat ggctgatgca atgcggcggc tgcatacgct tgatccggct acctgcccat    2820
tcgaccacca agcgaaacat cgcatcgagc gagcacgtac tcggatggaa gccggtcttg    2880
tcgatcagga tgatctggac gaagagcatc aggggctcgc gccagccgaa ctgttcgcca    2940
ggctcaaggc gagcatgccc gacggcgagg atctcgtcgt gacccatggc gatgcctgct    3000
tgccgaatat catggtggaa aatggccgct tttctggatt catcgactgt ggccggctgg    3060
gtgtggcgga ccgctatcag gacatagcgt tggctacccg tgatattgct gaagagcttg    3120
gcggcgaatg ggctgaccgc ttcctcgtgc tttacggtat cgccgctccc gattcgcagc    3180
gcatcgcctt ctatcgcctt cttgacgagt tcttctgaat tattaacgct tacaatttcc    3240
tgatgcggta ttttctcctt acgcatctgt gcggtatttc acaccgcata caggtggcac    3300
ttttcgggga atgtgcgcg gaacccctat ttgtttattt ttctaaatac attcaaatat    3360
gtatccgctc atgagacaat aaccctgata aatgcttcaa taatagcacg tgctaaaact    3420
tcatttttaa tttaaaagga tctaggtgaa gatcctttt gataatctca tgaccaaaat    3480
cccttaacgt gagttttcgt tccactgagc gtcagacccc gtagaaaaga tcaaaggatc    3540
ttcttgagat cctttttttc tgcgcgtaat ctgctgcttg caaacaaaaa aaccaccgct    3600
accagcggtg gtttgtttgc cggatcaaga gctaccaact ctttttccga aggtaactgg    3660
cttcagcaga gcgcagatac caaatactgt ccttctagtg tagccgtagt taggccacca    3720
cttcaagaac tctgtagcac cgcctacata cctcgctctg ctaatcctgt taccagtggc    3780
tgctgccagt ggcgataagt cgtgtcttac cgggttggac tcaagacgat agttaccgga    3840
taaggcgcag cggtcgggct gaacggggg ttcgtgcaca cagcccagct tggagcgaac    3900
gacctacacc gaactgagat acctacagcg tgagctatga gaaagcgcca cgcttcccga    3960
agggagaaag gcggacaggt atccggtaag cggcagggtc ggaacaggag agcgcacgag    4020
ggagcttcca gggggaaacg cctggtatct ttatagtcct gtcgggtttc gccacctctg    4080
acttgagcgt cgatttttgt gatgctcgtc aggggcgg agcctatgga aaaacgccag    4140
caacgcggcc ttttacggtt cctgggctt tgctggcct tttgctcaca tgttcttgac    4200
tct                                                                  4203
```

<210> SEQ ID NO 37
<211> LENGTH: 4203
<212> TYPE: DNA
<213> ORGANISM: Artificial Sequence
<220> FEATURE:
<223> OTHER INFORMATION: plasmid

<400> SEQUENCE: 37

```
gactcttcgc gatgtacggg ccagatatac gcgttgacat tgattattga ctagttatta     60
atagtaatca attacggggt cattagttca tagcccatat atggagttcc gcgttacata    120
acttacggta aatggcccgc ctggctgacc gcccaacgac ccccgcccat tgacgtcaat    180
aatgacgtat gttcccatag taacgccaat agggactttc cattgacgtc aatgggtgga    240
ctatttacgg taaactgccc acttggcagt acatcaagtg tatcatatgc caagtacgcc    300
ccctattgac gtcaatgacg gtaaatggcc cgcctggcat tatgcccagt acatgacctt    360
```

```
atgggacttt cctacttggc agtacatcta cgtattagtc atcgctatta ccatggtgat    420
gcggttttgg cagtacatca atgggcgtgg atagcggttt gactcacggg gatttccaag    480
tctccacccc attgacgtca atgggagttt gttttggcac caaaatcaac gggactttcc    540
aaaatgtcgt aacaactccg ccccattgac gcaaatgggc ggtaggcgtg tacggtggga    600
ggtctatata agcagagctc tctggctaac tagagaaccc actgcttact ggcttatcga    660
aattaatacg actcactata gggagaccca agctggctag cgtttaaact taagctgatc    720
cactagtcca gtgtggtgga attcgccatg agatctgact acaaagacca tgacggtgat    780
tataaagatc atgacatcga ttacaaggat gacgatgaca agatggcccc caagaagaag    840
aggaaggtgg gcattcatgg ggtacccgcc gctatggctg agaggcccct tccagtgtcga    900 atctgcatgc gtaacttcag tcgctccgac cacctgtcca cccacatccg cacccacacc    960
ggcgagaagc cttttgcctg tgacatttgt gggaggaaat ttgcccgctc cgacgccctg   1020
gcccgccata ccaagataca cacgggcagc caaaagccct tccagtgtcg aatctgcatg   1080
cgtaacttca gtcagtcctc cgacctgtcc cgccacatcc gcacccacac cggcgagaag   1140
ccttttgcct gtgacatttg tgggaggaaa tttgccgacc gctcccacct ggcccgccat   1200
accaagatac acacgggatc tcagaagccc ttccagtgtc gaatctgcat gcgtaacttc   1260
agtcagtcct ccgacctgtc ccgccacatc cgcacccaca ccggcgagaa gccttttgcc   1320
tgtgacattt gtgggaggaa atttgcccgc tccgaccacc tgacccagca taccaagata   1380
cacctgcggg gatcccagct ggtgaagagc gagctggagg agaagaagtc cgagctgcgg   1440
cacaagctga gtacgtgcc ccacgagtac atcgagctga tcgagatcgc caggaacagc   1500
acccaggacc gcatcctgga gatgaaggtg atggagttct tcatgaaggt gtacggctac   1560
aggggaaagc acctgggcgg aagcagaaag cctgacggcg ccatctatac agtgggcagc   1620
cccatcgatt acggcgtgat cgtggacaca aaggcctaca gcggcggcta caatctgcct   1680 atcgccagg ccgacgagat gcagagatac gtgaaggaga accagacccg gaataagcac   1740
atcaacccca cgagtggtg gaaggtgtac cctagcagcg tgaccgagtt caagttcctg   1800
ttcgtgagcg ccacttcaa gggcaactac aaggcccagc tgaccaggct gaaccacaaa   1860
accaactgca atggcgccgt gctgagcgtg gaggagctgc tgatcggcgg cgagatgatc   1920
aaagccggca ccctgacact ggaggaggtg cggcgcaagt tcaacaacgg cgagatcaac   1980
ttctgataac tcgagtctag agggcccgtt taaacccgct gatcagcctc gactgtgcct   2040
tctagttgcc agccatctgt tgtttgcccc tccccgtgc cttccttgac cctggaaggt   2100
gccactccca ctgtcctttc ctaataaaat gaggaaattg catcgcattg tctgagtagg   2160
tgtcattcta ttctgggggg tggggtgggg caggacagca agggggagga ttgggaagac   2220
aatagcaggc atgctgggga tgcggtgggc tctatggctt ctactgggcg gttttatgga   2280
cagcaagcga accggaattg ccagctgggg cgccctctgg taaggttggg aagccctgca   2340
aagtaaactg gatggctttc tcgccgccaa ggatctgatg gcgcagggga tcaagctctg   2400
atcaagagac aggatgagga tcgtttcgca tgattgaaca agatggattg cacgcaggtt   2460
ctccggccgc ttgggtggag aggctattcg gctatgactg gcacaacag acaatcggct   2520 gctctgatgc cgccgtgttc cggctgtcag cgcaggggcg cccggttctt tttgtcaaga   2580
ccgacctgtc cggtgccctg aatgaactgc aagacgaggc agcgcggcta tcgtggctgg   2640
ccacgacggg cgttccttgc gcagctgtgc tcgacgttgt cactgaagcg ggaagggact   2700
ggctgctatt gggcgaagtg ccggggcagg atctcctgtc atctcacctt gctcctgccg   2760
```

```
agaaagtatc catcatggct gatgcaatgc ggcggctgca tacgcttgat ccggctacct    2820
gcccattcga ccaccaagcg aaacatcgca tcgagcgagc acgtactcgg atggaagccg    2880
gtcttgtcga tcaggatgat ctggacgaag agcatcaggg gctcgcgcca gccgaactgt    2940
tcgccaggct caaggcgagc atgcccgacg gcgaggatct cgtcgtgacc catggcgatg    3000
cctgcttgcc gaatatcatg gtggaaaatg gccgcttttc tggattcatc gactgtggcc    3060
ggctgggtgt ggcggaccgc tatcaggaca tagcgttggc tacccgtgat attgctgaag    3120
agcttggcgg cgaatgggct gaccgcttcc tcgtgcttta cggtatcgcc gctcccgatt    3180
cgcagcgcat cgccttctat cgccttcttg acgagttctt ctgaattatt aacgcttaca    3240
atttcctgat gcggtatttt ctccttacgc atctgtgcgg tatttcacac cgcatacagg    3300
tggcactttt cggggaaatg tgcgcggaac ccctatttgt ttattttttct aaatacattc    3360 aaatatgtat ccgctcatga gacaataacc ctgataaatg cttcaataat agcacgtgct    3420
aaaacttcat ttttaattta aaaggatcta ggtgaagatc cttttttgata atctcatgac    3480 caaaatccct aacgtgagt tttcgttcca ctgagcgtca gaccccgtag aaaagatcaa    3540
aggatcttct tgagatcctt ttttttctgcg cgtaatctgc tgcttgcaaa caaaaaaacc    3600
accgctacca gcggtggttt gtttgccgga tcaagagcta ccaactcttt ttccgaaggt    3660
aactggcttc agcagagcgc agataccaaa tactgtcctt ctagtgtagc cgtagttagg    3720
ccaccacttc aagaactctg tagcaccgcc tacatacctc gctctgctaa tcctgttacc    3780
agtggctgct gccagtggcg ataagtcgtg tcttaccggg ttggactcaa gacgatagtt    3840
accggataag gcgcagcggt cgggctgaac ggggggttcg tgcacacagc ccagcttgga    3900
gcgaacgacc tacaccgaac tgagatacct acagcgtgag ctatgagaaa gcgccacgct    3960
tcccgaaggg agaaaggcgg acaggtatcc ggtaagcggc agggtcggaa caggagagcg    4020
cacgagggag cttccagggg gaaacgcctg gtatctttat agtcctgtcg ggtttcgcca    4080
cctctgactt gagcgtcgat ttttgtgatg ctcgtcaggg gggcggagcc tatggaaaaa    4140
cgccagcaac gcggcctttt tacggttcct gggcttttgc tggccttttg ctcacatgtt    4200
ctt                                                                  4203
```

<210> SEQ ID NO 38
<211> LENGTH: 368
<212> TYPE: DNA
<213> ORGANISM: Artificial Sequence
<220> FEATURE:
<223> OTHER INFORMATION: mutated chinese hamster IGF1-Receptor gene
      fragment

<400> SEQUENCE: 38

```
agcgtgcacc gagaacaacg aatgctgcca cccagagtgc ctaggcagct gccatacacc     60
tgacgacaac acaacctgtg tggcctgccg acactactac tacaaaggcg tgtgtgtgcc    120
tgcctgccca cctggcacct acgttcgagg gctggcgctg tgtggaccgc gatttctgcg    180
ccaacatccc caacgctgag agcagtgact cagatggctt tgtcatccac gatggcgagt    240
gcatgcaaga atgtccctca ggcttcatcc gcaacagcac ccagaggtca gtggctcttg    300
ttccccatcc aggaggtgaa tcttgttcat attccatgat tgtaggaacc acccagaggt    360
tcatccag                                                            368
```

<210> SEQ ID NO 39
<211> LENGTH: 365

```
<212> TYPE: DNA
<213> ORGANISM: Artificial Sequence
<220> FEATURE:
<223> OTHER INFORMATION: mutated chinese hamster IGF1-Receptor gene
      fragment

<400> SEQUENCE: 39
agcgtgcacc gagaacaacg aatgctgcca cccagagtgc ctaggcagct gccatacacc      60
tgacgacaac acaacctgtg tggcctgccg acactactac tacaaaggcg tgtgtgtgcc     120
tgcctgccca cctggcacct acagagggct ggcgctgtgt ggaccgcgat ttctgcgcca     180
acatccccaa cgctgagagc agtgactcag atggctttgt catccacgat ggcgagtgca     240
tgcaagaatg tccctcaggc ttcatccgca acagcaccca gaggtcagtg gctcttgttc     300
cccatccagg aggtgaatct tgttcatatt ccatgattgt aggaaccacc cagaggttca     360
tccag                                                                  365

<210> SEQ ID NO 40
<211> LENGTH: 368
<212> TYPE: DNA
<213> ORGANISM: Artificial Sequence
<220> FEATURE:
<223> OTHER INFORMATION: mutated chinese hamster IGF1-Receptor gene
      fragment

<400> SEQUENCE: 40
agcgtgcacc gagaacaacg aatgctgcca cccagagtgc ctaggcagct gccatacacc      60
tgacgacaac acaacctgtg tggcctgccg acactactac tacaaaggcg tgtgtgtgcc     120
tgcctgccca cctggcacct acgttcgagg gctggcgctg tgtggaccgc gatttctgcg     180
ccaacatccc caacgctgag agcagtgact cagatggctt tgtcatccac gatggcgagt     240
gcatgcaaga atgtccctca ggcttcatcc gcaacagcac ccagaggtca gtggctcttg     300
ttccccatcc aggaggtgaa tcttgttcat attccatgat gtaggaacc acccagaggt      360 tcatccag                                                               368

<210> SEQ ID NO 41
<211> LENGTH: 348
<212> TYPE: DNA
<213> ORGANISM: Artificial Sequence
<220> FEATURE:
<223> OTHER INFORMATION: mutated chinese hamster IGF1-Receptor gene
      fragment

<400> SEQUENCE: 41
agcgtgcacc gagaacaacg aatgctgcca cccagagtgc ctaggcagct gccatacacc      60
tgacgacaac acaacctgtg tggcctgccg acactactac tacaaaggcg tgtgtgtgcc     120
tgcctgccca cctggcgctg tgtggaccgc gatttctgcg ccaacatccc caacgctgag     180
agcagtgact cagatggctt tgtcatccac gatggcgagt gcatgcaaga atgtccctca     240
ggcttcatcc gcaacagcac ccagaggtca gtggctcttg ttccccatcc aggaggtgaa     300
tcttgttcat attccatgat gtaggaacc acccagaggt tcatccag                    348

<210> SEQ ID NO 42
<211> LENGTH: 388
<212> TYPE: DNA
<213> ORGANISM: Artificial Sequence
<220> FEATURE:
<223> OTHER INFORMATION: mutated chinese hamster IGF1-Receptor gene
      fragment
```

```
<400> SEQUENCE: 42
agcgtgcacc gagaacaacg aatgctgcca cccagagtgc ctaggcagct gccatacacc      60
tgacgacaac acaacctgtg tggcctgccg acactactac tacaaaggcg tgtgtgtgcc     120
tgcctgccca cctggtgagg tataggacag tattatagag gtggggcagg gctggcgctg     180
tgtggaccgc gatttctgcg ccaacatccc caacgctgag agcagtgact cagatggctt     240
tgtcatccac gatggcgagt gcatgcaaga atgtccctca ggcttcatcc gcaacagcac     300
ccagaggtca gtggctcttg ttccccatcc aggaggtgaa tcttgttcat attccatgat     360
tgtaggaacc acccagaggt tcatccag                                         388

<210> SEQ ID NO 43
<211> LENGTH: 256
<212> TYPE: DNA
<213> ORGANISM: Artificial Sequence
<220> FEATURE:
<223> OTHER INFORMATION: mutated chinese hamster IGF1-Receptor gene
      fragment

<400> SEQUENCE: 43
agcgtgcacc gagaacaacg aatgctgcca cccagagtgc tggcgctgtg tggaccgcga      60
tttctgcgcc aacatcccca cgctgagag cagtgactca gatggctttg tcatccacga     120
tggcgagtgc atgcaagaat gtccctcagg cttcatccgc aacagcaccc agaggtcagt     180
ggctcttgtt ccccatccag gaggtgaatc ttgttcatat tccatgattg taggaaccac     240
ccagaggttc atccag                                                      256

<210> SEQ ID NO 44
<211> LENGTH: 348
<212> TYPE: DNA
<213> ORGANISM: Artificial Sequence
<220> FEATURE:
<223> OTHER INFORMATION: mutated chinese hamster IGF1-Receptor gene
      fragment

<400> SEQUENCE: 44
agcgtgcacc gagaacaacg aatgctgcca cccagagtgc ctaggcagct gccatacacc      60
tgacgacaac acaacctgtg tggcctgccg acactactac tacaaaggcg tgtgtgtgcc     120
tgcctgccca cctggcgctg tgtggaccgc gatttctgcg ccaacatccc caacgctgag     180
agcagtgact cagatggctt tgtcatccac gatggcgagt gcatgcaaga atgtccctca     240
ggcttcatcc gcaacagcac ccagaggtca gtggctcttg ttccccatcc aggaggtgaa     300
tcttgttcat attccatgat tgtaggaacc acccagaggt tcatccag                   348

<210> SEQ ID NO 45
<211> LENGTH: 363
<212> TYPE: DNA
<213> ORGANISM: Artificial Sequence
<220> FEATURE:
<223> OTHER INFORMATION: mutated chinese hamster IGF1-Receptor gene
      fragment

<400> SEQUENCE: 45
agcgtgcacc gagaacaacg aatgctgcca cccagagtgc ctaggcagct gccatacacc      60
tgacgacaac acaacctgtg tggcctgccg acactactac tacaaaggcg tgtgtgtgcc     120
tgcctgccca cctggcacct acagggctgg cgctgtgtgg accgcgattt ctgcgccaac     180
atccccaacg ctgagagcag tgactcagat ggctttgtca tccacgatgg cgagtgcatg     240
```

```
caagaatgtc cctcaggctt catccgcaac agcacccaga ggtcagtggc tcttgttccc    300
catccaggag gtgaatcttg ttcatattcc atgattgtag gaaccaccca gaggttcatc    360
cag                                                                  363

<210> SEQ ID NO 46
<211> LENGTH: 18
<212> TYPE: DNA
<213> ORGANISM: Artificial Sequence
<220> FEATURE:
<223> OTHER INFORMATION: PCR primer

<400> SEQUENCE: 46
aggcgattaa gttgggta                                                   18

<210> SEQ ID NO 47
<211> LENGTH: 20
<212> TYPE: DNA
<213> ORGANISM: Artificial Sequence
<220> FEATURE:
<223> OTHER INFORMATION: PCR primer

<400> SEQUENCE: 47
taatacgact cactataggg                                                 20

<210> SEQ ID NO 48
<211> LENGTH: 23
<212> TYPE: PRT
<213> ORGANISM: artificial sequence
<220> FEATURE:
<223> OTHER INFORMATION: mutated human IGF1 Ea peptide SEQ ID 33
      disclosed on page 41

<400> SEQUENCE: 48

Val Gln Ala Gln Gln His Thr Asp Met Pro Lys Thr Gln Lys Glu Val
1               5                   10                  15

His Leu Lys Asn Ala Ser Gly
            20

<210> SEQ ID NO 49
<211> LENGTH: 32
<212> TYPE: PRT
<213> ORGANISM: artificial sequence
<220> FEATURE:
<223> OTHER INFORMATION: mutated human IGF1 Ea peptide SEQ ID 34
      disclosed on page 42

<400> SEQUENCE: 49

Val Gln Ala Gln Gln His Thr Asp Met Pro Lys Thr Gln Lys Tyr Gln
1               5                   10                  15

Pro Pro Ala Thr Asn Lys Asn Thr Lys Ser Gln Arg Arg Lys Gly Ser
            20                  25                  30
```